United States Patent
Xu et al.

(10) Patent No.: US 7,468,255 B2
(45) Date of Patent: Dec. 23, 2008

(54) METHOD FOR ASSAYING FOR NATURAL KILLER, CYTOTOXIC T-LYMPHOCYTE AND NEUTROPHIL-MEDIATED KILLING OF TARGET CELLS USING REAL-TIME MICROELECTRONIC CELL SENSING TECHNOLOGY

(75) Inventors: Xiao Xu, San Diego, CA (US); Yama Abassi, San Diego, CA (US); Xiaobo Wang, San Diego, CA (US)

(73) Assignee: ACEA Biosciences, San Diego, CA (US)

( * ) Notice: Subject to any disclaimer, the term of this patent is extended or adjusted under 35 U.S.C. 154(b) by 315 days.

(21) Appl. No.: 11/197,994

(22) Filed: Aug. 4, 2005

(65) Prior Publication Data

US 2006/0023559 A1     Feb. 2, 2006

Related U.S. Application Data

(63) Continuation-in-part of application No. 11/055,639, filed on Feb. 9, 2005, which is a continuation-in-part of application No. 10/987,732, filed on Nov. 12, 2004, now Pat. No. 7,192,752, and a continuation-in-part of application No. 10/705,447, filed on Nov. 10, 2003, said application No. 10/987,732 is a continuation-in-part of application No. 10/705,615, filed on Nov. 10, 2003, application No. 11/197,994, which is a continuation-in-part of application No. PCT/US2005/004481, filed on Feb. 9, 2005, and a continuation-in-part of application No. PCT/US2004/037696, filed on Nov. 12, 2004.

(60) Provisional application No. 60/519,567, filed on Nov. 12, 2003, provisional application No. 60/435,400, filed on Dec. 20, 2002, provisional application No. 60/469,572, filed on May 9, 2003, provisional application No. 60/542,927, filed on Feb. 9, 2004, provisional application No. 60/548,713, filed on Feb. 27, 2004, provisional application No. 60/614,601, filed on Sep. 29, 2004, provisional application No. 60/598,608, filed on Aug. 4, 2004, provisional application No. 60/630,071, filed on Nov. 22, 2004, provisional application No. 60/689,422, filed on Jun. 10, 2005, provisional application No. 60/598,609, filed on Aug. 4, 2004, provisional application No. 60/613,872, filed on Sep. 27, 2004, provisional application No. 60/647,189, filed on Jan. 26, 2005, provisional application No. 60/647,075, filed on Jan. 26, 2005, provisional application No. 60/660,829, filed on Mar. 10, 2005, provisional application No. 60/660,898, filed on Mar. 10, 2005.

(51) Int. Cl.
G01N 33/574     (2006.01)

(52) U.S. Cl. .................. 435/7.23; 435/7.24; 435/29

(58) Field of Classification Search ....................... None
See application file for complete search history.

(56) References Cited

U.S. PATENT DOCUMENTS

| | | | |
|---|---|---|---|
| 2,656,508 A | 10/1953 | Coulter |
| 3,259,842 A | 7/1966 | Coulter et al. |
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah et al. |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,766,934 A | 6/1998 | Guiseppi-Elie |

(Continued)

FOREIGN PATENT DOCUMENTS

EP          1 138 758 A1     4/2001

(Continued)

OTHER PUBLICATIONS

Wegner et al. Electric Cell-Substrate Impedance Sensing (ECIS) as a Noninvasive Means to Monitor the Kinetics of Cell Spreading to Artificial Surfaces. Experimental Cell Research 259, 158-166 (2000).

(Continued)

*Primary Examiner*—James S Ketter
(74) *Attorney, Agent, or Firm*—David R. Preston & Associates APC

(57) ABSTRACT

The present invention includes a method of measuring cytolytic activity including providing a device capable of monitoring cell-substrate impedance operably connected to an impedance analyzer, adding target cells to at least one well of the device, adding effector cells to the at least one well, monitoring impedance of the at least one well and optionally determining a cell index from the impedance, wherein monitoring impedance includes measuring impedance during at least one time point before and at least one time point after adding effector cells, and determining viability of said target cells after adding effector cells by comparing the impedance or optionally the cell index at the at least one time point after adding effector cells to the impedance or optionally the cell index at the at least one time point before adding effector cells.

39 Claims, 48 Drawing Sheets

U.S. PATENT DOCUMENTS

| | | | |
|---|---|---|---|
| 5,801,055 | A | 9/1998 | Henderson |
| 5,810,725 | A | 9/1998 | Sugihara et al. |
| 5,851,489 | A | 12/1998 | Wolf et al. |
| 5,981,268 | A | 11/1999 | Kovacs et al. |
| 6,051,422 | A | 4/2000 | Kovacs et al. |
| 6,132,683 | A | 10/2000 | Sugihara et al. |
| 6,169,394 | B1 | 1/2001 | Frazier et al. |
| 6,232,062 | B1 | 5/2001 | Kayyem et al. |
| 6,235,520 | B1 | 5/2001 | Malin et al. |
| 6,280,586 | B1 | 8/2001 | Wolf et al. |
| 6,288,527 | B1 | 9/2001 | Sugihara et al. |
| 6,368,795 | B1 | 4/2002 | Hefti |
| 6,368,851 | B1 | 4/2002 | Baumann et al. |
| 6,376,233 | B1 | 4/2002 | Wolf et al. |
| 6,440,662 | B1 | 8/2002 | Gerwen et al. |
| 6,448,030 | B1 | 9/2002 | Rust et al. |
| 6,448,794 | B1 | 9/2002 | Cheng et al. |
| 6,461,808 | B1 | 10/2002 | Bodner et al. |
| 6,472,144 | B2 | 10/2002 | Malin et al. |
| 6,485,905 | B2 | 11/2002 | Hefti |
| RE37,977 | E | 2/2003 | Sugihara et al. |
| 6,566,079 | B2 | 5/2003 | Hefti |
| 6,573,063 | B2 | 6/2003 | Hochman |
| 6,596,499 | B2 | 7/2003 | Jalink |
| 6,626,902 | B1 | 9/2003 | Kucharczyk et al. |
| 6,627,461 | B2 | 9/2003 | Chapman et al. |
| 6,630,359 | B1 | 10/2003 | Caillat |
| 6,637,257 | B2 | 10/2003 | Sparks et al. |
| RE38,323 | E | 11/2003 | Sugihara et al. |
| 6,686,193 | B2 | 2/2004 | Maher et al. |
| 6,716,620 | B2 | 4/2004 | Bashir et al. |
| 6,723,523 | B2 | 4/2004 | Lynes et al. |
| 7,192,752 | B2 | 3/2007 | Xu et al. |
| 2002/0032531 | A1 | 3/2002 | Mansky et al. |
| 2002/0076690 | A1 | 6/2002 | Miles et al. |
| 2002/0086280 | A1 | 7/2002 | Lynes et al. |
| 2002/0090649 | A1 | 7/2002 | Chan et al. |
| 2002/0110847 | A1 | 8/2002 | Baumann et al. |
| 2002/0150886 | A1 | 10/2002 | Miles et al. |
| 2003/0032000 | A1 | 2/2003 | Liu et al. |
| 2003/0072549 | A1 | 4/2003 | Facer et al. |
| 2003/0116447 | A1 | 6/2003 | Surridge et al. |
| 2003/0143625 | A1 | 7/2003 | Martin et al. |
| 2003/0157587 | A1 | 8/2003 | Gomez et al. |
| 2003/0166015 | A1 | 9/2003 | Zarowitz et al. |
| 2004/0091397 | A1 | 5/2004 | Picard |
| 2004/0146849 | A1 | 7/2004 | Huang et al. |
| 2005/0014130 | A1 | 1/2005 | Liu et al. |

FOREIGN PATENT DOCUMENTS

| | | |
|---|---|---|
| EP | 1195432 B1 | 9/2004 |
| WO | 96/01836 | 1/1996 |
| WO | 99/66329 | 12/1999 |
| WO | 00/71669 | 11/2000 |
| WO | 01/25769 | 4/2001 |
| WO | 01/038873 | 5/2001 |
| WO | 02/04943 | 1/2002 |
| WO | 02/42766 | 5/2002 |
| WO | 03/016887 | 2/2003 |
| WO | 2005/005979 | 1/2005 |

OTHER PUBLICATIONS

Cady et al., Electrical Impedance Measurements: Rapid Method for Detecting and Monitoring Microorganisms, J Clin Microb.7:265-72 (1978).
Mohr et al., Performance of a thin film microelectrode array for monitoring electrogenic cells in vitro, Sensors and Actuators B34:265-269. 1996.
Aravanis et al. Biosensors & Bioelectronics 16:571-577 (2001).
Baumann et al. Sensors & Accuators B55:77-89 (1999).
Becker et al, Cell Biology. 92:960-964 (1995).
Berens et al, Clin. Exp. Metastasis 12:405-415 (1994).
Bergveld, Biosensors & Bioelectronics. 6:55-72 (1991).
Bieberich and Guiseppi-Elie, Biosensors and Bioelectronics, 19:923-931 (2004).
Burnett et al., J. Biomo. Screening, 8(6):660-667 (2003).
Burns et al, Journal of Immunology 2893-2903 (1997).
Ciambrone et al., J. Biomo. Screening, 9(6):467-480 (2004).
Connolly et al, Biosensors & Bioelectronics 5: 223-234 (1990).
Duan et al, Anal. Chem. 66:1369-1377 (1994).
Ehret et al, Biosensors and Bioelectronics 12(1):29-41 (1997).
Ehret et al, Medical & Biological Engineering and Computing 36:365-370 (1998).
Falk et al, J. Immunol. Meth. 33:239-247 (1980).
Fuhr et al, Sensors and Materials 7(2):131-146 (1995).
Gaiever et al, Proc. Natl. Acad. Sci 84:3761-3764 (1984).
Giaever et al, Proc. Natl. Acad. USA 88: 7896-7900 (1991).
Gutmann et al, Pharmaceutical Research, 16(3):402-407 (1999).
Hadjout et al., BioTechniques 31: 1130-1138 (2001).
Henning et al, Anti-Cancer Drugs 12:21-32 (2001).
Hidalgo et al, Gastroenterology 96:736-749 (1989).
Huang et al, Anal. Chem. 74:3362-3371 (2002).
Hug, Assay and Drug Dev. Tech., 1(3):479-488 (2003).
Keese et al, Biotechniques 33:842-850 (2002).
Kleinmann et al, Biochemistry. 26:312-318 (1986).
Kowolenko et al, Journal of Immunological Methods 127: 71-77 (1990).
Larsen et al, Micro Total Analysis Systems 103-106 (2000).
Lin and Huang, J. Micromech. Microeng., 11:542-547 (2001).
Lin et al., Min. For Chem., Bio., & Bioeng., 4:104-108 (2004).
Lo et al, Experimental Cell Research 204:102-109 (1993).
Lo et al, Experimental Cell Research 213: 391-397 (1994).
Lo et al, Biophysical Journal 69: 2800-2807 (1995).
Loffert et al., QUIAGENNews, 4:15-18 (1997).
Luong, et al, Analytical Chemistry 73: 1844-1848 (2001).
Mitra et al, Biotechniques 11(4):504-510 (1991).
Miyata et al, Jpn. J. Ophthalmol. 34:257-266 (1990).
Nerurkar et al, Pharmaceutical Research 13(4):528-534 (1996).
Ong et al, Sensors 2:219-222 (2002).
Pancrazio et al, Sensors and Actuators B 53:179-185 (1998).
Patolsky et al, Nature Biotechnology 19:253-257 (2001).
Pethig et al, Appl. Phys. 24:881-888 (1992).
Richards et al, Immunological Communications 13(1):49-62 (1984).
Rishpon et al, Biosensors & Bioelectronics, 12(3):195-204 (1997).
Simpson et al., Trends in Biotechnology 19: 317-323 (2001).
Sohn et al, Proc. Nat. Acad. Sci. 97(20)10687-10690 (2000).
Stenger et al, Trends in Biotechnology 19: 304-309 (2001).
Svetlicic et al, Bioelectrochemistry 53: 79-86 (2000).
Tiruppathi et al, Proc Natl Acad Sci USA 89:7919-7923 (1992).
Wang et al, Appl. Phys. 1649-1660 (1996).
Wang et al, Appl. Phys. 26:1278-1285 (1993).
Wang et al, Anal. Chem. 72:832-839 (2000).
Wang et al, Biophysical Journal 72:1887-1899 (1997).
Wang et al, Biophysical Journal 74:2689-2701 (1998).
Wang et al., In Biochip Technology (eds.) Harwood Academic Publishers, PA U.S.A. 135-159 (2001).
Warburg, Ann. Phy. 6:125-135 (1901).
Wegener et al., Eur. J. Physiol., 437:925-934 (1999).
Wolf et al, Biosensors & Bioelectronics 13:501-509 (1998).
Xiao and Luong, Biotechnol. Prog., 19:1000-1005 (2003).
xiao et al., Anal. Chem., 74:5748-5753 (2002).
Xiao et al, Anal. Chem 74:1333-1339 (2002).
Yamauchi et al., Nuc. Acids Res., 32(22):1-8 (2004).
Yang et al, Anal. Chem. 71:911-918 (1999).
New Products page. Science 298:2409 (2002).
Abstract: Real-Time Impedance Assay to Follow the Invasive Activities of Metastatic Cells in Culture. Biotechniques 33: 842 (2002).

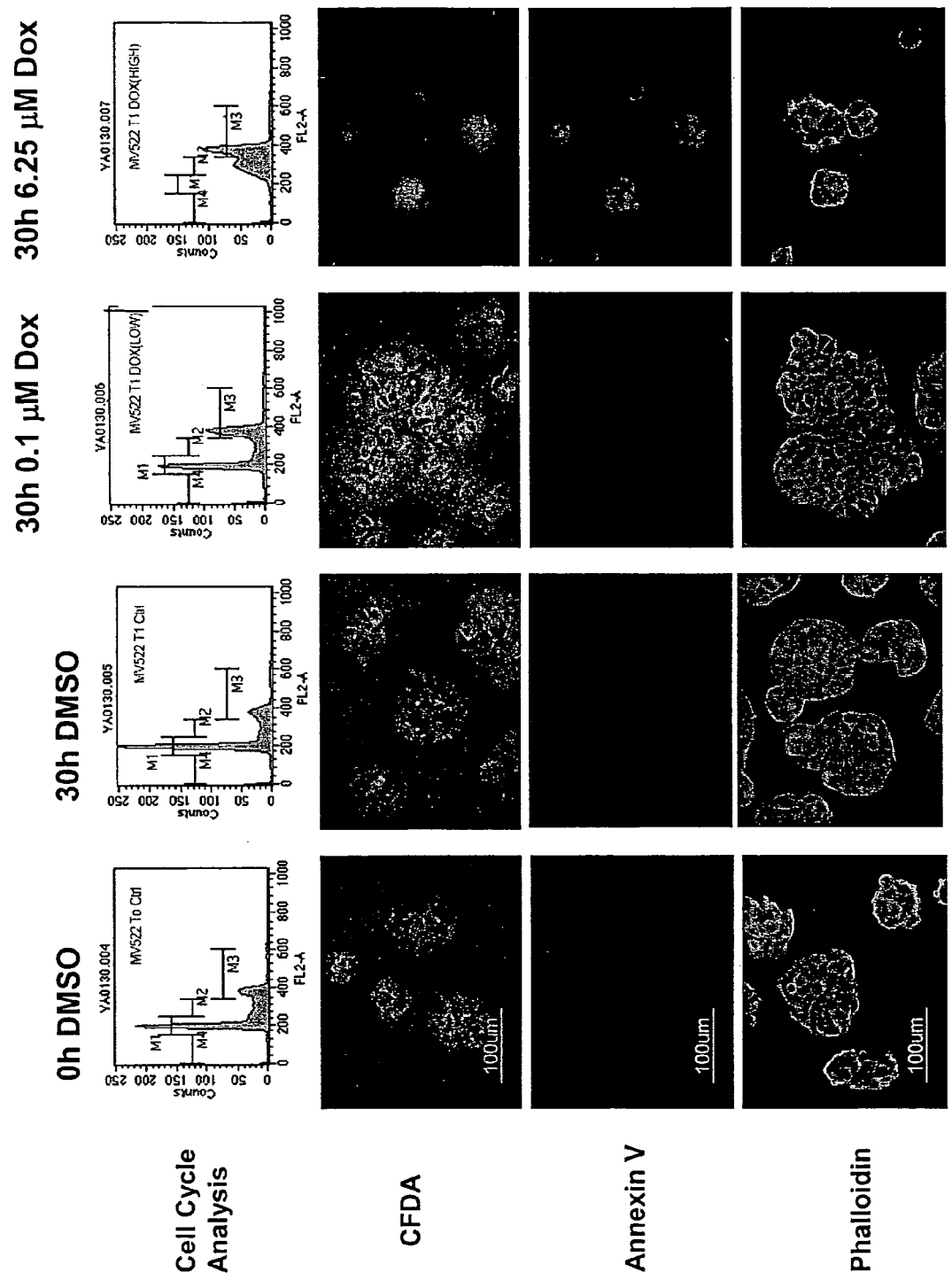
Figure 12.B

Shade-coding Scheme

▨ CCI >> 0.7/DT:

▦ CCI ~ 0.7/DT:

▒ 0< CCI < 0.7/DT:

||||  CCI ~ 0:

▨ CCI < 0:

≡ CCI << 0:

Figure 16C

NIH3T3+ YAC Cells (E/T= 15:1)   NIH3T3+ mNK Cells (E/T= 15:1)

METHOD FOR ASSAYING FOR NATURAL KILLER, CYTOTOXIC T-LYMPHOCYTE AND NEUTROPHIL-MEDIATED KILLING OF TARGET CELLS USING REAL-TIME MICROELECTRONIC CELL SENSING TECHNOLOGY

CROSS REFERENCE TO RELATED APPLICATIONS

This application is a continuation-in-part of U.S. patent application Ser. No. 11/055,639, entitled "Real time-electronic cell sensing system and applications for cytotoxicity profiling and compound assays" filed on Feb. 9, 2005 which is a continuation-in-part of U.S. patent application Ser. No. 10/987,732, entitled "Real time electronic cell sensing system and application for cell based assays" filed on Nov. 12, 2004 now U.S. Pat. No. 7,192,752, which claims priority from U.S. Provisional Application 60/519,567, filed on Nov. 12, 2003. Parent U.S. patent application Ser. No. 10/987,732 is itself a continuation-in-part of U.S. patent application Ser. No. 10/705,447 filed on Nov. 10, 2003, entitled "Impedance Based Devices and Methods for Use in Assays" which claims priority to U.S. Provisional Application 60/397,749, filed on Jul. 20, 2002; U.S. Provisional Application 60/435,400, filed on Dec. 20, 2002; U.S. Provisional Application 60/469,572, filed on May 9, 2003; and PCT application PCT/US03/22557, filed on Jul. 18, 2003. All of the applications referred to in this paragraph are incorporated by reference in their entireties herein.

Parent U.S. patent application Ser. No. 10/987,732 is also a continuation-in-part of U.S. patent application Ser. No. 10/705,615, entitled "Impedance Based Apparatuses and Methods for Analyzing Cells and Particles", filed on Nov. 10, 2003, which claims priority to U.S. Provisional Application 60/397,749 filed on Jul. 20, 2002; U.S. Provisional Application 60/435,400, filed on Dec. 20, 2002; U.S. Provisional Application 60/469,572, filed on May 9, 2003; and PCT application PCT/US03/22537, filed on Jul. 18, 2003. All of the applications referred to in this paragraph are incorporated by reference in their entireties herein.

Parent U.S. patent application Ser. No. 11/055,639 also claims priority to U.S. Provisional Patent Application No. 60/542,927 filed on Feb. 9, 2004; U.S. Provisional Application 60/548,713, filed on Feb. 27, 2004, and U.S. Provisional Application No. 60/614,601, filed on Sep. 29, 2004. All of the applications referred to in this paragraph are incorporated by reference in their entireties herein.

This application is also a continuation-in-part of PCT Patent Application No. PCT/US05/04481, filed on Feb. 9, 2005, and this application is a continuation-in-part of PCT Patent Application No. PCT/US04/37696, filed on Nov. 12, 2004. All of the applications referred to in this paragraph are incorporated by reference in their entireties herein.

This application also claims benefit of priority to, U.S. Provisional Patent Application No. 60/598,608, filed on Aug. 4, 2004, U.S. Provisional Patent Application No. 60/630,071, filed on Nov. 22, 2004, U.S. Provisional Patent Application No. 60/689,422, filed on Jun. 10, 2005, U.S. Provisional Patent Application No. 60/598,609, filed on Aug. 4, 2004, U.S. Provisional Patent Application No. 60/613,872, filed on Sep. 27, 2004, U.S. Provisional Patent Application No. 60/647,189, filed on Jan. 26, 2005, U.S. Provisional Patent Application No. 60/647,075 filed on Jan. 26, 2005, U.S. Provisional Patent Application No. 60/660,829 filed on Mar. 10, 2005, and U.S. Provisional Patent Application No. 60/660,898 file on Mar. 10, 2005. All of the applications referred to in this paragraph are incorporated by reference in their entireties herein.

This application also incorporates by reference in their entireties U.S. patent application Ser. No. 11/198,831, filed on Aug. 4, 2005, entitled, "Dynamic Monitoring of Activation of G-Protein Coupled Receptor (GPCR) and Receptor Tyrosine Kinase (RTK) in Living Cells Using Microelectronic Cell Sensing Technology", and PCT Patent Application Number (PCT/US05/27943), filed on Aug. 4, 2005 entitled, "Dynamic Monitoring of Activation of G-Protein Coupled Receptor (GPCR) and Receptor Tyrosine Kinase (RTK) in Living Cells Using Microelectronic Cell Sensing Technology".

TECHNICAL FIELD

This invention relates to the field of cell-based assays. In particular, the invention provides impedance-based devices, apparatuses, systems and methods for analyzing cells and for conducting cell-based assays.

BACKGROUND OF THE INVENTION

A. Electronic Analysis of Cells

Bioelectronics is a progressing interdisciplinary research field that involves the integration of biomatereials with electronic devices. Bioelectronic methods have been used for analyzing cells and assaying biological molecules and cells. In one type of application, cells are cultured on microelectrodes and cell-electrode impedance is measured and determined to monitor cellular changes.

In PCT Application No. PCT/US03/22557, entitled "IMPEDANCE BASED DEVICES AND METHODS FOR USE IN ASSAYS", filed on Jul. 18, 2003, a device for detecting cells and/or molecules on an electrode surface is disclosed. The device detects cells and/or molecules through measurement of impedance changes resulting from the attachment or binding of cells and/or molecules to the electrode surfaces. A number of embodiments of the device is disclosed, together with the apparatuses, system for using such devices to perform certain cell based assays.

In PCT Application No. PCT/US04/037696, entitled "REAL TIME ELECTRONIC CELL SENSING SYSTEM AND APPLICATION FOR CELL-BASED ASSAYS", filed on Nov. 12, 2004, devices, systems and methods for assaying cells using cell-substrate impedance monitoring are disclosed. In one aspect, the disclosed cell-substrate monitoring devices comprise electrode arrays on a nonconducting substrate, in which each of the arrays has an approximately uniform electrode resistance across the entire array. In another aspect, the disclosed cell-substrate monitoring systems comporse one or more cell-substrate devices comprising multiple wells each having an electrode array, an impedance analyzer, a device station that connects arrays of individual wells to the impedance analyzer, and software for controlling the device station and impedance analyzer. In another aspect, the disclosed cellular assays use impedance monitoring to detect changes in cell behavior or state.

In PCT Application No. PCT/US05/004481, entitled "REAL TIME ELECTRONIC CELL SENSING SYSTEM AND APPLICATIONS FOR CYTOTOXICITY PROFILING AND COMPOUND ASSAYS", filed on Feb. 9, 2005, devices, systems and methods for assaying cells using cell-substarte impedance monitoring are disclosed. In one aspect, the disclosed cellular assays use impedance monitoring to detect changes in cell behavior or state. The methods can be used to test the effects of compounds on cells, such as in cytotoxicity assays. Methods of cytotoxicity profiling of compounds were also provided.

B. Natural Killer Cell-Mediated Cytotoxicity Assays

Natural killer (NK) cells are an integral part of the innate immune response. NK cells have been endowed with the ability to recognize and annihilate cells with extreme stress load such as virus infected cells as well as tumor cells (Lanier, 2005). The death mediated by NK cells is rapid and multifaceted. In addition to their important role in innate immune response, NK cells also serve as key mediators for activation of the adaptive immune response, by secreting factors which serve to activate and propagate B and T lymphocytes (Djeu et al., 2002; Lanier, 2005; Smyth et al., 2005). By responding immediately to infected cells, NK cells keep pathogen infection at bay while giving the adaptive arm of the immune response time to mobilize and respond to pathogen challenge in a more specific manner.

NK cells express specific receptors on its surface that can recognize pathogen infected and tumor cells by their lack of expression or low expression of the major histocompatability complex (MHC) at the membrane (Cerwenka and Lanier, 2001; Lanier, 2005). These receptors can be both inhibitory and stimulatory and the combined action of these receptors determines the extent of the dual nature of NK cell response to target cells; namely cytotoxicity and/or cytokine production (Lanier, 2005). When NK inhibitory receptors bind to MHC class I molecules, their effector functions are blocked and therefore normal healthy cells which express adequate levels of these receptors are spared from the NK cell attack. On the other hand activating receptors such as NKG2D is engaged by ligands that are MHC-like and expressed by pathogen infected and transformed cells as well other stressed cells (Cerwenka and Lanier, 2001). The immediate effector function of NK cells results in the release of secretory granules mainly containing special proteins and enzymes of the perforin family and granzyme family (Smyth et al., 2005). The perforins bind to the cell membrane and disrupt the integrity of the plasma membrane whereas granzymes are a special class of serine proteases with various substrate specificities, including caspases (Trapani and Smyth, 2002). The combined interplay of these proteins and enzymes ultimately result in target cell cytotoxicity and destruction. In addition to granzyme and perforin-mediated cytotoxicity, NK cells also express Trail and FasL, both of which can contribute to NK-mediated cytotoxicity towards target cells (Smyth et al., 2002).

A number of techniques have been devised for monitoring NK-mediated cytotoxicity towards target cells. The most popular method relies on chromium 51 labeling of target cells and measuring the release of chromium upon cytolysis (Brunner et al., 1968). Other label-based methods such as annexin-V staining of target cells and using fax analysis to analyze apoptotic cells have also been described (Goldberg et al., 1999). Enzymatic assays which measure the activity of certain enzymes such as lactate dehydrogenase (LDH) or Granzymes have also been described in the literature as a means to assess NK-mediated cytotoxicity (Korzeniewski and Callewaert, 1983; Ewen et al., 2003; Shafer-Weaver et al., 2003). While all of the above mentioned assays, especially chromium 51 release assay have proved informative and are in routine use, they all have certain drawbacks which limit their utility. For example, chromium labeling involves the usage of a radioactive label which can be hazardous and difficult to dispose of. Furthermore, chromium 51 assay window is limited to four hours beyond which the natural tendency of chromium to diffuse out of the cell contributes to high background. In addition, all the mentioned assays are end-point assays which provide a "snapshot" of the NK-mediated cytotoxicity activity and with respect to chromium 51 release assay, it would be difficult to measure NK-mediated target cell killing after the 4 hour time window. Thus, technologies or methods that do not the use of radioactive labels and can provide kinetic information about NK-mediated cytotoxicity process are needed.

The present invention further expands the inventions disclosed in PCT Application No. PCT/US03/22557, entitled "IMPEDANCE BASED DEVICES AND METHODS FOR USE IN ASSAYS", filed on Jul. 18, 2003, and disclosed in U.S. patent application Ser. No. 10/705,447, entitled "IMPEDANCE BASED DEVICES AND METHODS FOR USE IN ASSAYS," filed on Nov. 10, 2003, and disclosed in PCT Application No. PCT/US05/004481, entitled "REAL TIME ELECTRONIC CELL SENSING SYSTEM AND APPLICATIONS FOR CYTOTOXICITY PROFILING AND COMPOUND ASSAYS", filed on Feb. 9, 2005, and disclosed in U.S. patent application Ser. No. 11/055,639, entitled "REAL TIME ELECTRONIC CELL SENSING SYSTEM AND APPLICATIONS FOR CYTOTOXICITY PROFILING AND COMPOUND ASSAYS" filed on Feb. 9, 2005, and disclosed in PCT Application No. PCT/US04/037696, entitled "REAL TIME ELECTRONIC CELL SENSING SYSTEM AND APPLICATION FOR CELL-BASED ASSAYS", filed on Nov. 12, 2004, and disclosed in U.S. patent application Ser. No. 10/987,732, entitled "REAL TIME ELECTRONIC CELL SENSING SYSTEM AND APPLICATION FOR CELL-BASED ASSAYS" filed on Nov. 12, 2004. The present invention provides a real time cell electronic sensing system for conducting cell-based assays based on measurement of cell-substrate impedance and provides the method for using such a system for assaying for natural killer, cytotoxic T-lymphocyte and neutrophil-mediated killing of target cells using real-time microelectronic cell sensing technology.

SUMMARY OF THE INVENTION

In one aspect, the present invention is directed to a device for monitoring cell-substrate impedance, which device comprises: a) a nonconducting substrate; b) two or more electrode arrays fabricated on the substrate, where each of the two or more electrode arrays comprises two electrode structures; and c) at least two connection pads, each of which is located on an edge of the substrate. Each electrode array of the device has an approximately uniform electrode resistance distribution across the entire array. The substrate of the device has a surface suitable for cell attachment or growth; where cell attachment or growth on said substrate can result in a detectable change in impedance between or among the electrode structures within each electrode array. In preferred embodiments, each electrode array on the substrate of a device of the present invention is associated with a fluid-impermeable container.

In another aspect, the present invention is directed to a cell-substrate impedance measurement system comprising: a) at least one multiple-well device monitoring cell-substrate impedance, in which at least two of the multiple wells each comprise an electrode array at the bottom of the well; b) an impedance analyzer; c) a device station capable of engaging the one or more multiple-well devices and capable of selecting and electrically connecting electrode arrays within any of the multiple wells in to the impedance analyzer; and d) a software program to control the device station and perform data acquisition and data analysis on impedance values measured by the impedance analyzer. In preferred embodiments of this aspect of the present invention, each electrode array of the multiple-well device is individually addressed.

In yet another aspect, the present invention provides a method for monitoring cell-substrate impedance using a device of the present invention. The method includes: providing a multiple array device of the present invention; connecting said multiple array device to an impedance analyzer; depositing cells on at least one of the two or more arrays of the device; and monitoring cell-substrate impedance on one or more arrays of the device.

In yet another aspect, the present invention provides methods for calculating a Cell Change Index for quantifying and comparing cell-substrate impedance.

In yet another aspect, the present invention provides methods for calculating resistance of electrical traces connecting an array of a cell-substrate monitoring device with a connection pad. Such calculations of electrical trace resistance can be used for calculating Cell Index.

In yet another aspect, the present invention provides a method for monitoring cell-substrate impedance using a cell-substrate impedance measurement system of the present invention. The method includes: providing a cell-substrate impedance measurement system of the present invention, adding cells to at least one well of the multiple-well device that comprises an electrode array, and monitoring cell-substrate impedance from one or more of the wells that comprise cells. Impedance can be monitored at regular or irregular time intervals. In preferred embodiments, cell-substrate impedance is monitored in at least two wells of a multiple-well device.

In yet another aspect, the present invention provides a method for performing real-time cell-based assays investigating the effects of one or more compound on cells, comprising: providing an above described cell-substrate impedance measurement system; introducing cells into at least one well of the system that comprises an electrode array; adding one or more compounds to one or more of the wells containing cells; and monitoring cell-substrate impedance over the electrode array of the one or more wells before and after adding the one or more compounds. Preferably, cell-substrate impedance is monitored at regular or irregular time intervals after adding one or more compounds to the one or more of the wells containing cells. The time dependent impedance change can provide information about time dependent cell status before addition of the compound and about time dependent cell status under the interaction of the compound. This information can be used to determine the effect of a compound on the cells.

In yet another aspect, the present invention provides a method for performing real-time cytotoxicity assays of at least one compound, comprising: providing an above described cell-substrate impedance measurement system; introducing cells into one or more wells of the system that comprise an electrode array; adding one or more compounds to the one or more wells containing cells; and monitoring cell-substrate impedance of the one or more wells before and after adding the one or more compounds, wherein the time dependent impedance change provides information about time dependent cytotoxicity of the compound or compounds. Preferably, cell-substrate impedance is monitored at regular or irregular time intervals after adding one or more compounds to the one or more of the wells containing cells. The time dependent impedance change can provide information about any potential cytotoxic effects of the compound.

In one embodiment of the above methods, multiple wells with same cell types are used, wherein different concentrations of a compound are added to different wells that comprise cells. The method can monitor and quantitate time-dependent and concentration-dependent cellular responses.

In yet another aspect, the present invention provides a method for analyzing and comparing time-dependent effects of a first compound and a second compound on a cell type, comprising: a) performing a real-time assay on a cell type with the first compound using the method described above; b) performing a real-time assay on said cell type with the second compound using the method described above; and c) comparing the time-dependent responses of the first compound and the second compound.

In one embodiment of this method, time-dependent cellular responses are determined for a first compound at multiple dose concentrations. In another embodiment, time-dependent responses are determined for a second compound at multiple dose concentrations. In yet another embodiment, time-dependent cellular responses are determined for both a first compound and a second compound at multiple dose concentrations.

In yet another aspect, the present invention provides methods for cytotoxicity profiling for a compound on multiple cell types, comprising: a) performing real-time cytotoxicity assays on different cell types with the compound using the method described above, and b) analyzing real-time cytotoxic responses of different cell types to the compound to provide a cytotoxicity profile of the compound. In yet another embodiment, the above methods are applied to perform cytotoxicity profiling of multiple compounds on multiple cell types.

In yet another aspect, the present invention provides a method of measuring cytolytic activity comprising: a) providing a device capable of monitoring cell-substrate impedance operably connected to an impedance analyzer, wherein the device comprises at least one well for receiving cells, b) adding target cells to the at least one well, c) adding effector cells to the at least one well, d) monitoring impedance of the at least one well and optionally determining a cell index from the impedance, wherein the monitoring impedance comprises measuring impedance during at least on time point before and at least one time point after adding effector cells, and e) determining viability of the target cells after adding effector cells by comparing the impedance or optionally the cell index at the at least one time point after adding effector cells to the impedance or optionally the cell index at the at least one time point before adding effector cells.

In yet another aspect, the present invention provides a method of measuring cytolytic activity comprising: a) providing a device capable of monitoring cell-substrate impedance operably connected to an impedance analyzer, wherein the device comprises two or more wells for receiving cells, b) adding target cells to at least two wells, wherein at least one well is a control well and at least one well is a test well, c) adding effector cells to the test well, d) monitoring impedance of the control and the test wells before and after adding the effector cells and optionally determining a cell index from the impedance, wherein the monitoring impedance comprises measuring the impedance during at least two time points, and e) determining viability of the target cells in the test well at a given time point after adding effector cells by comparing the impedance or optionally the cell index of the test well to the control well at the given time point.

In yet another aspect, the present invention provides a method of screening for antibody-dependent cellular toxicity (ADCC) comprising: a) providing a device capable of monitoring cell-substrate impedance operably connected to an impedance analyzer, wherein the device comprises two or more wells for receiving cells; b) adding target cells to at least two wells, wherein at least one well is a control well and at least one well is a test well; c) adding antibody capable of interacting with the target cells to the test well and an isotype control or non-specific antibody to the control well; d) adding effector cells to the test well and the control well; e) monitoring impedance of the test well and the control well before and after adding effector cells and optionally determining a cell index from the impedance, wherein the monitoring impedance comprises measuring impedance during at least one time point before and at least one time point after adding effector cells; and f) determining viability of the target cells in the test well at the at least one time point after adding the effector cells by comparing the impedance or optionally the cell index of the test well to the control well.

In yet another aspect, the present invention provides a method of assaying for complement-mediated cellular cytotoxicity comprising: a) providing a device capable of monitoring cell-substrate impedance operably connected to an impedance analyzer, wherein the device comprises two or more wells for receiving cells, b) adding target cells to at least two wells, wherein at least one well is a control well and at least one well is a test well, c) adding a complement and antibody capable of interacting with the target cells to the test well and the complement without the antibody or with an isotype control antibody to the control well, d) monitoring impedance of the test well and the control well before and after adding the complement and optionally determining a cell index from the impedance, wherein the monitoring impedance comprises measuring the impedance during at least two time points, and e) determining viability of the target cells in the test well at a given time point after adding the complement and antibody by comparing the impedance or optionally the cell index of the test well to the control well.

In yet another aspect, the present invention provides a method of assaying for complement-dependent effector cell-mediated cellular cytotoxicity comprising: a) providing a device capable of monitoring cell-substrate impedance operably connected to an impedance analyzer, wherein the device comprises two or more wells for receiving cells; b) adding target cells to at least two wells, wherein at least one well is a control well and at least one well is a test well; c) adding effector cells, a complement and antibody capable of interacting with the target cells to the test well, and effector cells and the complement without the antibody or with an isotype control antibody to the control well; d) monitoring impedance of the test well and the control well before and after adding the complement and optionally determining a cell index from the impedance, wherein the monitoring impedance comprises measuring the impedance during at least two time points; and e) determining viability of the target cells in the test well at a given time point after adding the complement and antibody by comparing the impedance or optionally the cell index of the test well to the control well.

In one embodiment of the above methods for measuring cytolytic activity, for screening for antibody-dependent cellular toxicity (ADCC), for assaying for complement-mediated cellular cytotoxicity and for assaying for complement-dependent effector cell-mediated cellular cytotoxicity, the device capable of monitoring cell-substrate impedance may comprise, a) a nonconducting substrate; b) two or more electrode arrays fabricated on the substrate, wherein each of the two or more electrode arrays comprises two electrode structures; c) the two or more wells on the substrate, wherein each of the two or more arrays is associated with one of the two or more wells; and d) at least two connection pads, each of which is located on an edge of the substrate; wherein for each of the two or more electrode arrays, each of the two electrode structures comprises multiple electrode elements and the first of the two electrode structures of each of the at least two electrode arrays is connected to one of the at least two connection pads, and the second of the two electrode structures of each of the at least two electrode arrays is connected to another of the at least two connection pads; further wherein at least two of the two or more electrode arrays share one common connection pad; further wherein each electrode array has an approximately uniform electrode resistance distribution across the entire array; and further wherein the substrate has a surface suitable for cell attachment or growth; wherein the cell attachment or growth on the substrate can result in a detectable change in impedance between or among the electrode structures within each electrode array.

In some embodiments of the above methods of the present invention for measuring cytolytic activity, for screening for antibody-dependent cellular toxicity (ADCC), for assaying for complement-mediated cellular cytotoxicity and for assaying for complement-dependent effector cell-mediated cellular cytotoxicity, the target cells may be selected from the group consisting of cancer cells, cells isolated from cancerous tissue, primary cells, endothelial ells and cells from a cell line derived from a living organism.

In another aspect, in some embodiments of the above methods of the present invention, the effector cells may be selected from the group consisting of Natural Killer (NK) cells, Cytotoxic T-Lymphocytes (CTLs), neutrophils, easonophils, macrophages, Natural Killer T (NKT) cells, B-cells, T-cells, and a cell type comprising cytolytic activity. In still other embodiments of the above methods, the effector cells are added at a predetermined ratio to said target cells, or are added at a series of predetermined ratio to target cells.

In some embodiments of the above methods of the present invention, the impedance is monitored at least at one time point before adding effector cells and at least at two time points after adding effector cells. In some other embodiments of the above methods, the impedance is monitored at regular or irregular time intervals during an assay period.

In one embodiments of the above methods, the cell index is determined by calculating, for each measurement frequency, the relative-change in resistance of a well when target cells are present in the well with respect to that of the well when no cell is present, and then finding the maximum relative-change in resistance for all frequencies measured. In yet another embodiment of the above methods, the cell index is a normalized cell index and normalization is at a time point immediately preceding said adding effector cells. In yet another embodiment of the above methods, a time point immediately preceding said adding effector cells may refer a time point of less than 2 hours, less than 1 hour, less than 40 minutes, less than 20 minutes, less than 10 minutes, less than 5 minutes, less than 2 minutes, or less than 1 minute prior to adding effector cells In one embodiment of the above methods of the present invention, the viability of the target cells decreases if said impedance or cell index decreases after said adding effector cells. In another embodiment of the above methods, the percent cytolysis at a given time point after adding effector cells is calculated by the formula of (1−cell index of test well/cell index of control well). In the formula to calculate the percent cytolysis, the cell index may be a normalized cell index and normalization is at a time point immediately preceding said adding effector cells.

In some embodiment of the above methods of the present invention, the methods may further comprise adding a compound or a factor suspected of stimulating said effector cells. The compound may be from any sources, for example, may be selected from a compound library. The factor may be any molecules, for example, may be selected from a group consisting of a monoclonal antibody, a polyclonal antibody, a peptide, a protein, a lipid, and a biomolecule. In another example, the factor may be selected from a group consisting of IgG, IgM, IgE and IgA.

In some embodiments of the above methods of the present invention, the methods may further comprise determining the quantity of said target cells based on a pre-derived formula that correlates cell number with said cell index at a time point prior to or after said adding effector cells.

In other embodiments of the above methods of present invention, the methods may comprise adding accessory cells or accessory compounds.

In one embodiment of the above methods of the present invention, the methods may be automated.

In one embodiment of the above method for screening for antibody-dependent cellular cytotoxicity, the impedance may be monitored at least at one time point prior to adding the antibody, at least at one time point after adding the antibody and before adding the effector cells, and at least at three time points after adding the effector cells.

In one embodiment of the above methods of the present invention, the antibody may be selected from a library of antibodies. The antibody may be of any type, and for example, the antibody may be selected from a group of a mouse antibody, a rat antibody, a humanized mouse antibody, and a humanized rat antibody.

BRIEF DESCRIPTION OF THE DRAWINGS

FIG. 12B shows the characterization of the cell biological effect of doxorubicin treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.

FIG. 16C shows the color-coding scheme used for representing the CCI curves. If the DT is the doubling time for the cells undergoing exponential growth in the cell culture media used, then CCI having different values relative to 0.7/DT indicates the different cell change status. If CCI >>0.7/DT, cell index increases faster than that expected for an exponential growth (or log growth) of the cells (such region n the CCI curve is represented as ▓Rectangle). If CCI is about 0.7/DT, cell index increases in the same rate as that expected for an exponential growth of the cells (such region in the CCI curve is represented as ▓Rectangle). If CCI is more than zero but somewhat smaller than 0.7/DT, then cell index increases in the rate slowed than that expected for an exponential growth (such region of the CCI curve is represented as ▓Rectangle). If CCI is about zero, then cell index shows a near constant value (such region of the CCI curve is represented as ≡Rectangle). If CCI is negative, then the cell index is decreasing with time, showing the cells losing attachment to the electrode surface or changing their morphology (such region of the curve is shown as ▓Rectangle). If CCI is very negative, then the cell index decreases rapidly with time, showing that either cells lose attachment to the electrode surfaces quickly or cells change their morphology very quickly (such region of the CCI curve is represented as ▓Rectangle). The transient, quick noise in the CCI values are removed so that the whole CCI curve is represented after compound addition by one, two or three black/white-shaded rectangles.

DETAILED DESCRIPTION OF THE INVENTION

A. Definitions

Figure 1A:
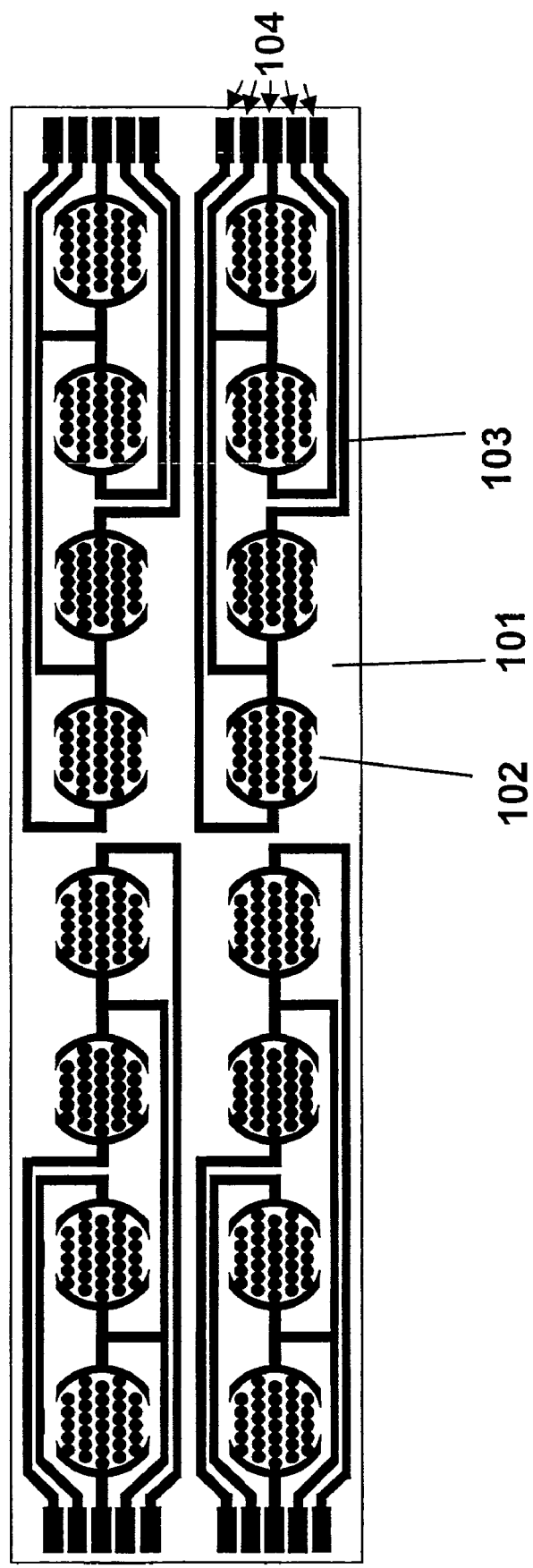
FIG. 1 shows schematic drawings of one design of a cell-substrate impedance measurement device of the present invention. A) depicts the substrate having 16 electrode arrays (or 16 electrode structure units) that are arranged in a 2-row by 8-column configuration on a substrate. B) depicts a single electrode array of a device. C) shows a schematic drawing of an electrode array, illustrating the requirement of approximately uniform distribution of electrode resistance across the array.

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occuring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes [or electrode structures] have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the does concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown. In one application of the present invention, a compound is capable of, or is suspected of, inducing cytotoxicity. In another application of present invention, a compound is capable of, or is suspected of, stimulating effector cells. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the 1$^{st}$ order derive of the Cell Index with respect to time, divided by the Cell Index at the time point. In other words, CCI is calculated as $$CCI(t) = \frac{dCI(t)}{CI(t) \cdot dt}.$$

As used herein, "cytolytic activity" refers to the ability of effector cells to lyse or kill target cells. For a given ratio of effector cell number to target cell number and for a specific time period after addition of effector cells to target cells, if effector cells of a first type kills more target cells than effector cells of a second type, then the effector cells of the first type have higher cytolytic activity. There are various parameters that can be determined and be used to indicate or quantify cytolytic activity of effector cells. For example, viability of target cells at a time point after effector cells are added to target cells in a well can be used to indicate the cytolytic activity of the effector cells. A low viability of target cells indicates that many target cells have been killed by the effector cells and shows that the effector cells have high cytolytic activity. In another example, percent cytolysis (or percentage of cytolysis) of target cells at a time point after effector cells are added to target cells can also be used to indicate the cytolytic activity. A low percent cytolysis indicates that few target cells have been killed by the effector cells and show that the effector cells have low cytolytic activity.

As used herein, "target cell" or "target cells" refers to any cell that can be lysed or killed by the effector cells. Non-limiting examples of target cells include cancer cells, cells isolated from cancerous tissues, primary cells, endothelial cells or any cells from a cell line derived from a living organism. In the assay for measuring cytolytic activity of effector cells, one is interested in how many target cells or what percentage of target cells have been killed by the effector cells. Thus, the quantity of target cells, or the viability of the target cells may be determined at any time point during an assay.

As used herein, "effector cell" or "effector cells" refer to any cells that are capable of killing or lysing target cells, such as Natural Killer (NK) cells, Cytotoxic T-Lymphocytes (CTLs), neutrophils, easonophils, macrophages, Natural Killer T (NKT) cells, B-cells, T-cells, a cell type having cytolytic activity and the like.

As used herein, "viability" refers to quantity of, or percentage of viable cells that are alive and have not undergone cytolysis. In the assay for measuring cytolytic activity of effector cells, one may need to determine viability of target cells at some time point(s) after effector cells have been added to target cells in order to determine how many target cells or what percentage of target cells are killed or lysed by the effector cells. In one embodiment of a method of the present invention, target cells are introduced in wells comprising electrode arrays, which are used to measure cell-substrate impedance for quantifying the number of target cells. Impedance of a well containing target cells is measured prior to and after addition of effector cells to the wells. In one approach, viability of target cells at a time point after addition of effector cells may be determined by comparing the impedance of the well prior to and after addition of effectors. Viability of target cells may be calculated as the ratio of the impedance of the well at the time point of interest to the impedance of the well immediately prior to addition of effector cells. Such a calculation has an implicit assumption that the impedance of the well may be approximately proportional to the number of the viable cells in the well. Here for the time period from the time point of addition of effector cells to the time point of interest, it is assumed that there is little or no proliferation of target cells. Thus, the ratio of impedance of the well at the time point of interest to the impedance of the well immediately prior to addition of effcetor cells reflects the percentage of the initial cells (the viable cells immediately prior to addition of effector cells) which are still viable at the time point of interest. In another approach, viability of target cells at a time point after addition of effector cells may be determined by comparing the cell index of the well prior to and after addition of effector cells. Viability of target cells may be calculated as the ratio of the cell index of the well at the time point of interest to the cell index of the well immediately prior to addition of effector cells. Such a calculation has an implicit assumption that the cell index of the well may be approximately proportional to the number of the viable cells in the well. For such a calculation of viability of target cells, cell index may be normalized cell index. In still another approach, viability of target cells in a test well at a time point after addition of effector cells may be determined by comparing the impedance (or cell index) of the well at the time point of interest to the impedance (or cell index) of a control well to which same number of target cells and no effector cells are added. Viability of target cells at a time point after adding effector cells may be calculated as the ratio of the impedance (or cell index) of the test well at the time point of interest to the impedance (or cell index) of the control well at the same time point. Such a calculation of viability of target cells in a test well has an implicit assumption that if there is no killing or lysis of target cells by effector cells, the impedance or cell index of the test well would be the same as that of the control well. For such calculation of viability of target cells, cell index may be normalized cell index.

As used herein, "primary cell" or "primary cells" refers to any non-immortalized cell that has been derived from various tissues and organs of a patient or an animal.

As used herein, "cell or cells having cytolytic activity" refers to any cell that is capable of killing or lysing target cells. Cell or cells having cytolytic activity are effector cells.

As used herein, "antibody-dependent cellular cytotoxicity (ADCC)" refers to the killing of target cells (or cytotoxicity of target cells) by effector cells, where target cells have been marked by an antibody.

B. Devices and Systems for Monitoring Cell-substrate Impedance

Devices for Measuring Cell-Substrate Impedance

The present invention includes devices for measuring cell-substrate impedance that comprise a nonconducting substrate; two or more electrode arrays fabricated on the substrate, where each of the two or more electrode arrays comprises two electrode structures; and at least two connection pads, each of which is located on an edge of the substrate. Each electrode array of the device has approximately uniform electrode resistance across the entire array. The substrate of the device has a surface suitable for cell attachment or growth; where cell attachment or growth on said substrate can result in a detectable change in impedance between or among the electrode structures within each electrode array.

An electrode array is two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure. (For example, an electrode structure can comprise two or more electrode elements that are electrically connected together.) In devices of the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that is located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device of the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

Descriptions of electrode arrays used for impedance measurement that apply to the devices of the present invention are described in parent U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in parent U.S. patent application Ser. No. 10/705,447, and also in parent application U.S. patent application Ser. No. 10/987,732, both herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Methods of Use

The present invention also includes methods of using a device of the present invention that comprises fluid containers situated over electrode arrays to measure cell-substrate impedance. Such methods include: providing a device of the present invention that comprises fluid containers situated over electrode arrays, attaching an impedance analyzer to a device of the present invention, adding cells to one or more fluid containers of the device, and measuring impedance over one or more arrays of the device. Methods of performing cell assays using impedance measurement devices can be found in parent U.S. patent application Ser. No. 10/987,732 and U.S. patent application Ser. No. 10/705,447, both herein incorporated by reference for all disclosure of methods of using impedance measurement devices, as well as in Sections D and E of the present application.

Cell-Substrate Impedance Measurement Systems

In another aspect, the present invention is directed to a cell-substrate impedance measurement system comprising a) at least one multiple-well cell-substrate impedance measuring device, in which at least two of the multiple wells comprise an electrode array at the bottom of the well; b) an impedance analyzer electronically connected to the multiple-well cell-substrate impedance measuring device; c) a device station capable of engaging the one or more multiple-well devices and comprising electronic circuitry capable of selecting and connecting electrode arrays within any of the multiple wells to the impedance analyzer; and d) a software program connected to the device station and impedance analyzer to control the device station and perform data acquisition and data analysis from the impedance analyzer.

In a cell-substrate impedance measurement system of the present invention, the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 0.1 ohm and $10^3$ ohm in frequency range of 100 Hz to 100 kHz.

A cell-substrate measurement system can be used to efficiently and simultaneously perform multiple assays by using circuitry of the device station to digitally switch from recording from measuring impedance over an array in one well to measuring impedance over an array in another well. In one embodiment of the above system, the system under software control is capable of completing an impedance measurement for an individual well at a single frequency within less than ten seconds. In another embodiment, the averaged time used by the system to complete an impedance measurement for an individual well at a single frequency is less than one second.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. In one embodiment of the above system, the multiwell device takes the form of a specialized microtiter plate which has microelectronic sensor arrays integrated into the bottom of the wells.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes.

Preferred devices that can be part of a cell-substrate impedance monitoring system can be those described in parent U.S. patent application Ser. No. 10/705,447, and in U.S. patent application Ser. No. 10/987,732, both herein incorporated by reference for disclosure of cell-substrate impedance monitoring devices that comprise electrode arrays, including disclosure of their design, composition, and manufacture. Preferred devices that can be part of a cell-substrate impedance monitoring system can also be those described in the present application.

Preferably a multi-well device of a system of the present invention comprises between 4 and 1,536 wells, some or all of which can comprise electrode arrays. In some embodiments of the present invention, a device station can comprise one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station comprises electronic circuitry that can connect to an impedance monitoring device and an impedance analyzer and electronic switches that can switch on and off connections to each of the two or more electrode arrays of the multiwell devices used in the system. The switches of the device station are controlled by a software program. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored at at least three time points. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of cell growth or behavior based on impedance values and impedance value curves. The software of the impedance monitoring system can also store and display analyses of the data, such as calculated impedance values and kinetic parameters derived therefrom, Data can be displayed on a screen, as printed data, or both.

C. Methods for Calculating Cell Index (CI) and Cell Change Index (CCI)

Cell Index

Based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing cell behavior in the impedance-based assays of the present invention. In some applications of the present invention, "cell index" in the present application is the same as "cell number index" in PCT Application No. PCT/US03/22557, entitled "IMPEDANCE BASED DEVICES AND METHODS FOR USE IN ASSAYS", filed on Jul. 18, 2003 and in U.S. patent application Ser. No. 10/705,447, entitled "IMPEDANCE BASED DEVICES AND METHODS FOR USE IN ASSAYS," filed on Nov. 10, 2003, U.S. patent application Ser. No. 10/987,732, filed Nov. 12, 2004, U.S. patent application Ser. No. 10/705,447 and PCT Application No. PCT/US03/22557 are hereby incorporated by reference for the discussions and disclosures of cell index and cell number index they contain.

Various methods for calculating such a cell number index can be used, some of which are novel methods disclosed herein.

The present invention provides several methods of calculating cell index numbers for cells attached to two or more essentially identical arrays of a cell-substrate impedance device, where the cells are monitored for impedance changes. In preferred embodiments of the present invention, the methods calculate cell index number with better accuracy than previous methods of calculating cell index for cells on two or more arrays of a cell-substrate monitoring device. In some preferred methods of the present invention, methods of calculating a cell index rely on novel methods for calculating the resistances of electrical traces leading to two or more essentially identical arrays. The present invention therefore also includes methods of calculating resistances of electrical traces leading to two or more essentially identical arrays on a substrate.

By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-on-line or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

The following discussion provides novel methods of calculating cell index of cells adhered to arrays of a cell-substrate impedance monitoring device and novel methods for the calculation of the resistances of the electrical connection traces leading to two or more electrode arrays of a cell-substrate impedance monitoring device.

Impedance (Z) has two components, namely the resistance Rs and reactance Xs. Mathematically, the impedance Z is expressed as follows, $$Z=Rs+j\,Xs, \quad (2)$$

where $j=\sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z=Rp*(j\,Xp)/(Rp+j\,Xp), \quad (3)$$

where $j=\sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both of which are herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example (A), the cell index or cell number index can be calculated by:
(A1) at each measured frequency, calculating the resistance ratio by dividing the resistance of the electrode arrays when cells are present and/or attached to the electrodes by the baseline resistance,
(A2) finding or determining the maximum value in the resistance ratio over the frequency spectrum,
(A3) and subtracting one from the maximum value in the resistance ratio.

Using a mathematically formula, Cell Index is derived as $$\text{Cell Index} = \max_{i=1,2,\ldots N} \left( \frac{R_{cell}(f_i)}{R_b(f_i)} - 1 \right) \quad (4)$$

Where N is the number of the frequency points at which the impedance is measured. For example, if the frequencies used for the measurements are at 10 kHz, 25 kHz and 50 kHz, then N=3, $f_1$=10 kHz, $f_2$=25 kHz, $f_3$=50 kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

The cell index obtained for a given well reflects: 1) how many cells are attached to the electrode surfaces in this well, 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes, $R_{cell}(f_i)$ is about the same as $R_b(f_i)$, leading to Cell Index=0. A higher value of "cell number index" indicates that, for same type of the cells and cells under similar physiological conditions, more cells are attached to the electrode surfaces. In other words, under same physiological conditions, more cells attached on the electrodes, the larger the values $R_{cell}(f_i)$ is, leading to a large value for Cell Index. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces. Thus, for same number of the cells present in the well, change in a cell status will lead to a change in cell index. For example, an increase in cell adhesion or a cell spread leading to large cell/electrode contact area will result in an increase in $R_{cell}(f)$ and a larger Cell Index. On the other hand, a cell death or toxicity induced cell detachment, cell rounding up, will lead to smaller $R_{cell}(f)$ and thus smaller Cell Index.

In another example (B), the cell number index can be calculated by:
(B1) at each measured frequency, calculating the reactance ratio by dividing the reactance of the electrode arrays when cells are present on and/or attached to the electrodes by the baseline reactance,
(B2) finding or determining the maximum value in the reactance ratio over the frequency spectrum,
(B3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example (C), the cell index can be calculated by:
(C1) at each measured frequency, subtracting the baseline resistance from the resistance of the electrode arrays when cells are present or attached to the electrodes to determine the change in the resistance with the cells present relative to the baseline resistance;
(C2) then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example (D), the cell index can be calculated by:
(D1) at each measured frequency, calculating the magnitude of the impedance (equaling to $\sqrt{R_s^2 + X_s^2}$, where $R_s$ and $X_s$ are the serial resistance and reactance, respectively).
(D2) subtracting the magnitude of the baseline impedance from the magnitude of the impedance of the electrode arrays when cells are present or attached to the electrodes to determine the change in the magnitude of the impedance with the cells present relative to the baseline impedance;

(D3) then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example (E), the index can be calculated by:
(E1) at each measured frequency, calculating the resistance ratio by dividing the resistance of electrode arrays when cells are present or attached to the electrodes by the baseline resistance,
(E2) then calculating the relative change in resistance in each measured frequency by subtracting one from the resistance ratio,
(E3) then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example (F), the cell index can be calculated by:
(F1) at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i) = R_{s\text{-}cell}(f_i) - R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively);
(F3) analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example (G), the cell index can be calculated by:
(G1) at each measured frequency, calculating the magnitude of the impedance (equaling to $\sqrt{R_s^2 + X_s^2}$, where $R_s$ and $X_s$ are the serial resistance and reactance, respectively).
(G2) subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i) = |Z_{cell}(f_i)| - |Z_{baseline}(f_i)|$ for the frequency $f_i$, $|Z_{cell}(f_i)| = \sqrt{R_{s\text{-}cell}(f_i)^2 + X_{s\text{-}cell}(f_i)^2}$, $R_{s\text{-}cell}$ and $X_{s\text{-}cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array);
(G3) analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. patent application Ser. No. 10/705, 447, entitled "Impedance based devices and methods for use in assays", filed on Nov. 10, 2003 and PCT application number PCT/US03/22557, entitled "Impedance based devices and methods for use in assays", filed on Jul. 18, 2003, and U.S. patent application Ser. No. 10/987,732, all herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use measured impedance (e.g., at a single fixed frequency; or at a maximum relative-change frequency, or at multiple frequencies) as an indicator of cell conditions. If measured impedance values are directly used for monitoring cell conditions, then resistance, or reactance or both resistance and reactance can be used.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode-array} = Z_{total} - Z_{trace} - Z_{switch} \quad (5)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (+/−10%) with the on reactance being negligible (for example, less than 0.2 ohm in the frequency range of interest). Thus, if the trace impedance is determined or calculated, then formula (5) can be used to calculate the impedance of the electrode arrays with or without cells present.

Figure 1B:
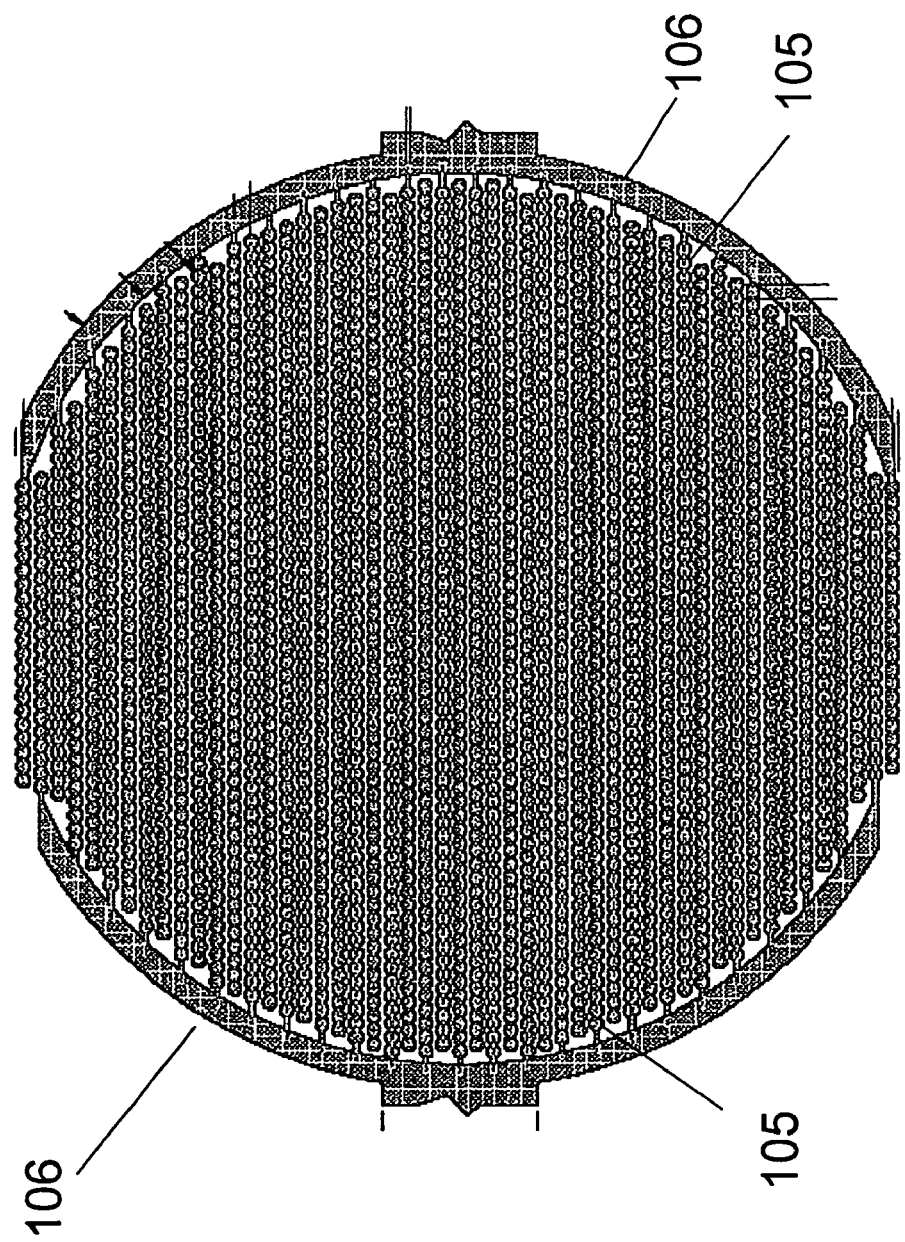
Figure 1C:
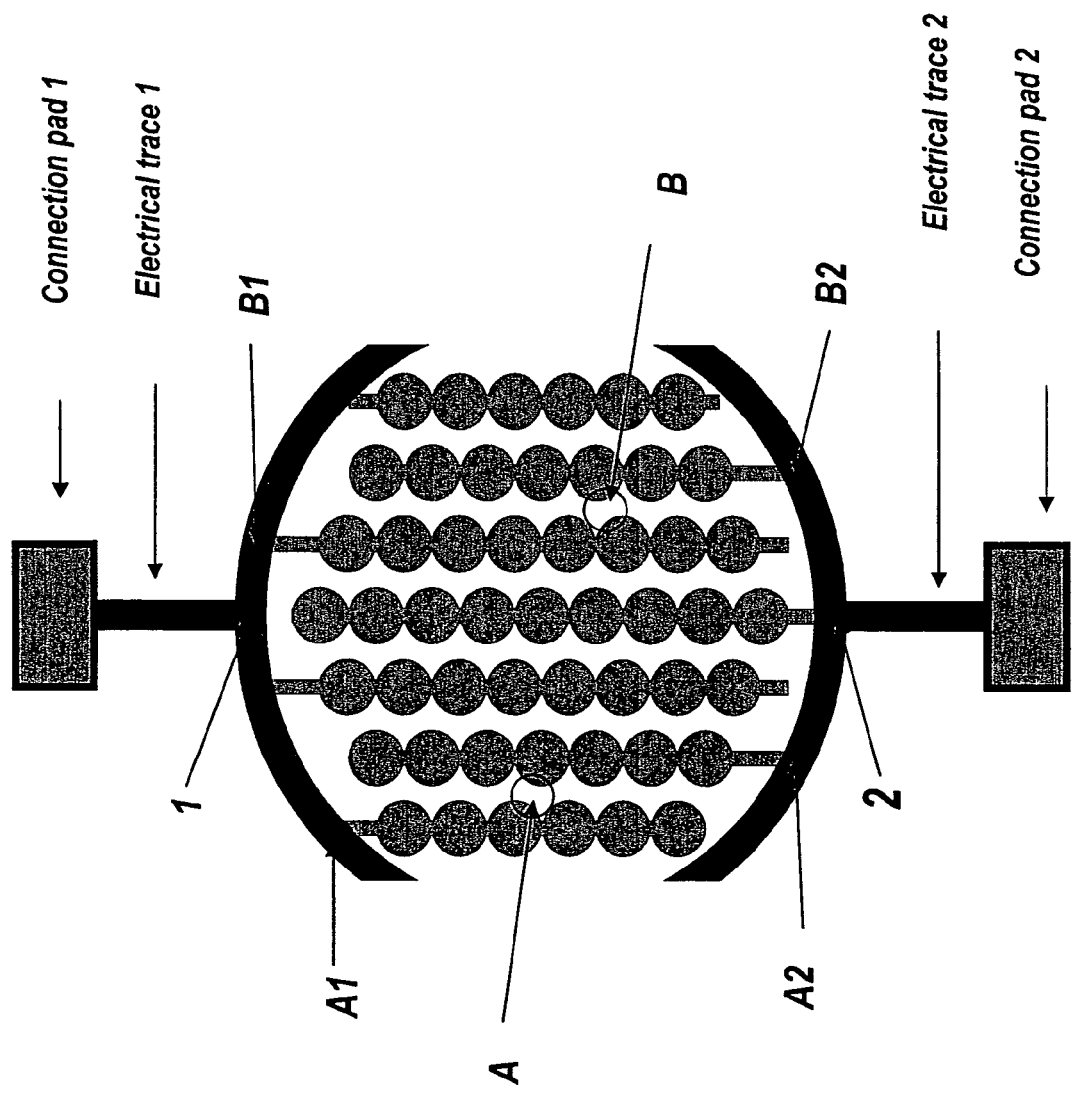

A method is invented in the present application to determine the impedance of electrical conductive (electrical connection) traces (mainly trace resistance, trace reactance is very small for the thin conductive film trace) based on the relationships among two or more essentially identical arrays on a cell-substrate impedance monitoring device. In the following, the four electrode arrays A, B, C and D as indicated in FIG. 1, are used to illustrate this method. The electrical reactance (serial reactance) of the electronic switches and the electrical reactance (serial reactance) of the electrical connection traces are small as compared with the corresponding electrical resistances (serial resistances). Thus, we focus on the analysis of the resistance of the electrical connection traces. The impedance determined from the impedance analyzer does contain both resistance (serial resistance, $R_{total}$) and reactance (serial reactance). For the electrode arrays A-D, the measured total resistance $R_{total}$, the resistance ($R_{trace}$) of electrical conductive (connection) trace, the switch resistance ($R_{switch}$) and the resistance ($R_{e-array}$) of the electrode array satisfy the following equations:

$$R_{e-array-A} = R_{total-A} - R_{trace-A} R_{switch-A} \quad (6A)$$

$$R_{e-array-B} = R_{total-B} - R_{trace-B} R_{switch-B} \quad (6B)$$

$$R_{e-array-C} = R_{total-C} - R_{trace-C} R_{switch-C} \quad (6C)$$

$$R_{e-array-D} = R_{total-D} - R_{trace-D} R_{switch-D} \quad (6D)$$

With chosen electronic switches having consistent switch-on resistance, $R_{switch-A}$, $R_{switch-B}$, $R_{switch-C}$ and $R_{switch-D}$ have very similar values and can be assumed to be the same, $R_{switch}$. Thus, in above equations, the known parameters are $R_{total-A}$, $R_{total-B}$, $R_{total-C}$, and $R_{total-D}$, and $R_{switch-A}$, $R_{switch-B}$, $R_{switch-C}$ and $R_{switch-D}$, and there are eight unknown parameters $R_{e-array-A}$, $R_{e-array-B}$, $R_{e-array-C}$, and $R_{e-array-D}$, and $R_{trace-A}$, $R_{trace-B}$, $R_{trace-C}$ and $R_{trace-D}$. It is impossible to solve these equations for the eight unknown variables from these four equations directly. Additional relationships between these variables are needed to solve for them. Each trace resistance ($R_{trace-A}$, $R_{trace-B}$, $R_{trace-C}$ and $R_{trace-D}$) depends on the metal film type used, and the geometry of the trace such as the how many rectangular segments the trace has, the film thickness(es) of the segments, the width(s) of the segments, the length(s) of the segment(s). For example, $$R_{trace-A} = \sum_{i=1}^{N} \rho \frac{L_{A-i}}{t_{A-i} * d_{A-i}} \quad (7)$$

where N is the number of the segments of the trace-A, $t_{A-i}$, $d_{A-i}$ and $L_{A-i}$ is the thickness, width and length of the i-th segment of the traces for the electrode array A, and $\rho$ is the resistivity of the thin film. The equation here applies to the film comprising a single type of metal. The equation can be readily modified to be applicable to the film comprising two or more metal types (e.g. gold film over chromium adhesion layer).

If the film thickness is reasonably uniform (for example, less than 10% in thickness variation) across the substrate, then the relationship among the trace resistances is simply determined by the pre-determined geometrical shapes (e.g. the length, width of the segments). For example, it would be straightforward to calculate the ratio $\alpha_{A-D}$ between the resistance of the electrically conductive traces for the electrode array A to the resistance of the electrically conductive traces for the electrode array D as below, where the film thickness is assumed to be the same everywhere on these traces and the resistivity is also the same everywhere on these traces, $$\alpha_{A-D} = \frac{R_{trace\_A}}{R_{trace\_D}} = \frac{\sum_{i=1}^{N} \rho \frac{L_{A-i}}{t_{A-i} * d_{A-i}}}{\sum_{i=1}^{M} \rho \frac{L_{D-i}}{t_{D-i} * d_{D-i}}} = \frac{\sum_{i=1}^{N} \frac{L_{A-i}}{d_{A-i}}}{\sum_{i=1}^{M} \frac{L_{D-i}}{d_{D-i}}}. \quad (8)$$

Similarly, one can determine the ratio $\alpha_{B-D}$ and $\alpha_{C-D}$ based on the pre-determined geometrical relationships for the traces of the electrode arrays B, C and D. Note that above equations can be similarly derived for the cases where the thin film in these traces comprises more than one metal type. Thus, based on the equalities $$R_{switch-A} = R_{switch-B} = R_{switch-C} = R_{switch-D} = R_{switch}, \quad (9A)$$

$$R_{trace-A} = \alpha_{A-D} \cdot R_{trace-D}, \quad (9B)$$

$$R_{trace-B} = \alpha_{B-D} \cdot R_{trace-D}, \quad (9C)$$

$$\text{and } R_{trace-C} = \alpha_{C-D} \cdot R_{trace-D} \quad (9D)$$

equations (6A)-(6D) can be re-written in the following format:

$$R_{e-array-A} = R_{total-A} - \alpha_{A-D} \cdot R_{trace-D} - R_{switch} \quad (10A)$$

$$R_{e-array-B} = R_{total-B} - \alpha_{B-D} \cdot R_{trace-D} - R_{switch} \quad (10B)$$

$$R_{e\text{-}array\text{-}C} = R_{total\text{-}C} - \alpha_{C\text{-}D} \cdot R_{trace\text{-}D} - R_{switch} \quad (10C)$$

$$R_{e\text{-}array\text{-}D} = R_{total\text{-}D} - \alpha_{D\text{-}D} \cdot R_{trace\text{-}D} - R_{switch} \quad (10D)$$

For equations (10A) through (10D), there are five unknown variables, $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$. Mathematically, these unknown variables cannot be determined from these equations. Additional information is needed to solve for these variables $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$.

One approach is invented and described in the present invention. In this approach, same biological or chemical solutions or suspensions are applied to the electrode-arrays A through D. Because the electrode arrays A through D have essentially identical electrode structures, the electrode array resistances $R_{e\text{-}array\text{-}A}$, $R_{e\text{-}array\text{-}B}$, $R_{e\text{-}array\text{-}C}$ and $R_{e\text{-}array\text{-}D}$ should be of same, or very similar value for such a condition when all the electrode arrays are exposed to the same biological or chemical solutions or suspensions, i.e.: $R_{e\text{-}array\text{-}A} \approx R_{e\text{-}array\text{-}B} \approx R_{e\text{-}array\text{-}C} \approx R_{e\text{-}array\text{-}D}$. If we assume the averaged electrode array resistance is $R_{e\text{-}array}$, then these approximate relationship exists $R_{e\text{-}array\text{-}A} \approx R_{e\text{-}array\text{-}B} \approx R_{e\text{-}array\text{-}C} \approx R_{e\text{-}array\text{-}D} \approx R_{e\text{-}array}$. Thus, equations (10A-10D) can be changed to the following:

$$R_{e\text{-}array} \approx R_{total\text{-}A} - \alpha_{A\text{-}D} \cdot R_{trace\text{-}D} - R_{switch} \quad (11A)$$

$$R_{e\text{-}array} \approx R_{total\text{-}B} - \alpha_{B\text{-}D} \cdot R_{trace\text{-}D} - R_{switch} \quad (11B)$$

$$R_{e\text{-}array} \approx R_{total\text{-}C} - \alpha_{C\text{-}D} \cdot R_{trace\text{-}D} - R_{switch} \quad (11C)$$

$$R_{e\text{-}array} \approx R_{total\text{-}D} - R_{trace\text{-}D} - R_{switch} \quad (11D)$$

Thus, we would need to find $R_{trace\text{-}D}$ and $R_{e\text{-}array}$ that satisfy the above approximate equality as close as possible. One mathematical approach is to find $R_{trace\text{-}D}$ and $R^{e\text{-}array}$ that would result in the minimum value for the following expression—an expression that quantifies the differences between the two sides of the approximate equality in (11A, 11B, 11C and 11D), $$F(R_{trace\text{-}D}, R_{e\text{-}array}) = [R_{e\text{-}array} - (R_{total\text{-}A} - \alpha_{A\text{-}D} R_{trace\text{-}D} - R_{switch})]^2 + [R_{e\text{-}array} - (R_{total\text{-}B} - \alpha_{B\text{-}D} R_{trace\text{-}D} - R_{switch})]^2 + [R_{e\text{-}array} - (R_{total\text{-}C} - \alpha_{C\text{-}D} R_{trace\text{-}D} - R_{switch})]^2 + [R_{e\text{-}array} - (R_{total\text{-}D} - R_{trace\text{-}D} - R_{switch})]^2 \quad (12)$$

The expression $F(R_{trace\text{-}D}, R_{e\text{-}array})$ is the sum of the squared-differences between the two-sides of the approximate equality in (11A, 11B, 11C and 11D). The smaller $F(R_{trace\text{-}D}, R_{e\text{-}array})$, the closer the two sides of the approximate equality (11A, 11B, 11C and 11D). Thus, values of $R_{trace\text{-}D}$ and $R_{e\text{-}array}$ that result in the minimum value of $F(R_{trace\text{-}D}, R_{e\text{-}array})$ should be determined. Mathematical approach involves in the calculation of the first order derivative of $F(R_{trace\text{-}D}, R_{e\text{-}array})$ to $R_{trace\text{-}D}$ and to $R_{e\text{-}array}$ and let such first order derivatives equal to zero. The values of $R_{trace\text{-}D}$ and $R_{e\text{-}array}$ that result in zero for these first-order-derivatives are those that result in the minimum value of $F(R_{trace\text{-}D}, R_{e\text{-}array})$. The first order derivatives are as follows:

$$\frac{\partial [F(R_{trace\text{-}D}, R_{e\text{-}array})]}{\partial R_{trace\text{-}D}} = 2 \cdot \alpha_{A\text{-}D} \cdot [R_{e\text{-}array} - (R_{total\text{-}A} - \alpha_{A\text{-}D} R_{trace\text{-}D} - R_{switch})] + 2 \cdot \alpha_{B\text{-}D} \cdot [R_{e\text{-}array} - (R_{total\text{-}B} - \alpha_{B\text{-}D} R_{trace\text{-}D} - R_{switch})] + 2 \cdot \alpha_{C\text{-}D} \cdot [R_{e\text{-}array} - (R_{total\text{-}C} - \alpha_{C\text{-}D} R_{trace\text{-}D} - R_{switch})] + 2 \cdot [R_{e\text{-}array} - (R_{total\text{-}D} - R_{trace\text{-}D} - R_{switch})] = 0; \quad (13A)$$

$$\frac{\partial [F(R_{trace\text{-}D}, R_{e\text{-}array})]}{\partial R_{e\text{-}array}} = 2 \cdot [R_{e\text{-}array} - (R_{total\text{-}A} - \alpha_{A\text{-}D} R_{trace\text{-}D} - R_{switch})] + 2 \cdot [R_{e\text{-}array} - (R_{total\text{-}B} - \alpha_{B\text{-}D} R_{trace\text{-}D} - R_{switch})] + 2 \cdot [R_{e\text{-}array} - (R_{total\text{-}C} - \alpha_{C\text{-}D} R_{trace\text{-}D} - R_{switch})] + 2 \cdot [R_{e\text{-}array} - (R_{total\text{-}D} - R_{trace\text{-}D} - R_{switch})] = 0. \quad (13B)$$

Equations (13A) and (13B) can be re-written as $$R_{e\text{-}array} \cdot [\alpha_{A\text{-}D} + \alpha_{B\text{-}D} + \alpha_{C\text{-}D} + 1] + R_{trace\text{-}D} \cdot [\alpha_{A\text{-}D}^2 + \alpha_{B\text{-}D}^2 + \alpha_{C\text{-}D}^2 + 1] = \alpha_{A\text{-}D} \cdot [R_{total\text{-}A} - R_{switch}] + \alpha_{B\text{-}D} \cdot [R_{total\text{-}B} - R_{switch}] + \alpha_{C\text{-}D} \cdot [R_{total\text{-}C} - R_{switch}] + [R_{total\text{-}D} - R_{switch}] \quad (14A)$$

$$4 \cdot R_{e\text{-}array} + R_{trace\text{-}D} \cdot [\alpha_{A\text{-}D} + \alpha_{B\text{-}D} + \alpha_{C\text{-}D} + 1] = [R_{total\text{-}A} - R_{switch}] + [R_{total\text{-}B} - R_{switch}] + [R_{total\text{-}C} - R_{switch}] + [R_{total\text{-}D} - R_{switch}] \quad (14B)$$

Thus, we can solve for $R_{trace\text{-}D}$ as follows:

$$R_{trace\text{-}D} = \frac{4 \cdot S_1 - A_{11} \cdot S_2}{4 \cdot A_{12} - A_{11} \cdot B_{12}} \quad (15)$$

where $A_{11} = [\alpha_{A\text{-}D} + \alpha_{B\text{-}D} + \alpha_{C\text{-}D} + 1]$;

$A_{12} = [\alpha_{A\text{-}D}^2 + \alpha_{B\text{-}D}^2 + \alpha_{C\text{-}D}^2 + 1]$;

$S_1 = \alpha_{A\text{-}D} \cdot [R_{total\text{-}A} - R_{switch}] + \alpha_{B\text{-}D} \cdot [R_{total\text{-}B} - R_{switch}] + \alpha_{C\text{-}D} \cdot [R_{total\text{-}C} - R_{switch}] + [R_{total\text{-}D} - R_{switch}]$;

$B_{12} = [\alpha_{A\text{-}D} + \alpha_{B\text{-}D} + \alpha_{C\text{-}D} + 1]$;

$S_2 = [R_{total\text{-}A} - R_{switch}] + [R_{total\text{-}B} - R_{switch}] + [R_{total\text{-}C} - R_{switch}] + [R_{total\text{-}D} - R_{switch}]$.

Thus, with the determined $R_{trace\text{-}D}$, the trace resistances of $R_{trace\text{-}A}$, $R_{trace\text{-}B}$, and $R_{trace\text{-}C}$ can be calculated using equations (9B), (9C) and (9D). Furthermore, the electrode array resistance $R_{e\text{-}array\text{-}A}$, $R_{e\text{-}array\text{-}B}$, $R_{e\text{-}array\text{-}C}$ and $R_{e\text{-}array\text{-}D}$ can be calculated from the measured resistance $R_{total\text{-}A}$, $R_{total\text{-}B}$, $R_{total\text{-}C}$ and $R_{total\text{-}D}$ respectively using equations (10A), (10B), (10C) and (10D).

Thus, one aspect of the present invention is directed to a method of calculation of the resistances of the electrical connection traces s from the measured, total resistances for two or more essentially identical electrode arrays (such as, for example arrays A-D in FIG. 1), comprising the following steps:

(1) exposing the electrode arrays to the solutions having same or similar solutions or suspensions;
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1), and the resistance of the electrode array with the solutions or suspensions present;
(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$.

Another aspect of the present invention is directed to a method of calculating the resistance of the electrode arrays from the measured, total electrode resistances for two ro more essentially identical electrode arrays (such as, for example arrays A-D in FIG. 1) if the same or similar solutions or suspensions are added to be in contact with the electrode assays, comprising the following steps:
(1) exposing the electrode arrays to the solutions having same or similar solutions or suspensions;
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the solutions or suspensions present;
(3) solving for the resistances of electrical connection traces using equation (15) and equations (9B), (9C) and (9D), noting in the calculation with equation (15), the geometrical relationships between the electrode arrays are used to determine the factor $\alpha_{A-D}$, $\alpha_{B-D}$ and $\alpha_{C-D}$;
(4) calculating the resistances of the electrode arrays using equations (10A, 10B, 10C and 10D)).

In many applications, the solutions or suspensions (for example, cell suspension) applied to each electrode array may have different compositions. For example, cell suspensions of different cell numbers may be used so that the suspensions applied to each electrode array are quite different. Under such cases, the determination of the resistance of the electrode arrays with the cells present would require the determination of the resistance of the electrical connection traces by performing a "reference run" or "calibration run" in which the electrode arrays are exposed to a same, reference solution. From the "reference run", the resistances of the electrical connection traces can be determined. In a separate test, the electrode arrays are exposed to the solutions or cell suspensions of interest and the resistances for the electrode arrays under such conditions are measured with an impedance analyzer or impedance measuring circuit. The resistance of the electrode arrays with such cell suspensions present can be determined (or continuously determined) from the measured resistance by subtracting the sum of the resistance of the electronic switches and the resistance of the electrical connection traces for corresponding electrode arrays from the measured resistances.

Thus, another aspect of the present invention is directed to a method of calculating the resistance of the electrode arrays from the total electrical resistances measured at an impedance analyzer for essentially identical electrode arrays (such as electrode arrays A-D in FIG. 1 used as an example) if different solutions or suspensions of interest are applied to the electrode assays, comprising the following steps:
(1) exposing the electrode arrays to the solutions having same or similar solutions or suspensions (reference solutions);
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the reference solutions present;
(3) solving for the resistances of electrical connection traces using equation (15) and equations (9B), (9C) and (9D), noting in the calculation with equation (15), the geometrical relationships between the electrode arrays of FIG. 1 are used to determine the factor $\alpha_{A-D}$, $\alpha_{B-D}$ and $\alpha_{C-D}$;
(4) applying the solutions or suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the solutions or suspensions of the interest present,
(5) Calculating the resistance of the electrode arrays using equations (10A), (10B), (10C) and (10D) by subtracting the electronic switch resistances and the resistances of electrical connection traces from the measured resistances in the step (4).

Note that in above method, the steps of exposing the electrode arrays to reference solutions for the determination of the resistances of electrically conductive traces (step (1), (2) and (3)) may be performed before or after the steps of applying the solutions or suspensions of interest to the electrode arrays and measuring the total electrical resistance (step (4)). For example, step (4) may be performed first. After that, the solutions or suspensions of the interest may be removed from the electrode array. The reference solutions can then be added to the electrode arrays (step (1)). Step (2) and step (3) can be then performed to determine the resistances of electrical connection traces. Finally, Step (5) can be done.

In another approach, step (1) and (2) can be performed ahead of step (4).

Another aspect of the present invention is directed to a method of determining the resistance of the electrode arrays with the cells present for a cell-based assay based on the total electrical resistance measured at an impedance analyzer for essentially identical electrode arrays. In this method, the electrode arrays are exposed to a same, reference solution (for example, a same cell culture medium that does not contain any cells) and electrical measurement is conducted to determine the resistance of electrical connection traces. With the resistances of the electrical connection traces determined, electrical resistances of the electrode arrays with cell suspensions added to electrode arrays can be calculated from the total electrical resistances measured at an impedance analyzer. Such total electrical resistance would include the resistance of the electrode arrays with cells present, the resistance of electronic switches and the resistance of electrical connection traces. The method comprises following steps (1) exposing the electrode arrays to the solutions having same or similar solutions or suspensions (reference solutions);

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIG. 1) and the resistance of the electrode arrays with the reference solutions present;

(3) solving for the resistances of electrical connection traces using equation (15) and equations (9B), (9C) and (9D), noting in the calculation with equation (15), the geometrical relationships between the electrode arrays in FIG. 1 are used to determine the factor $\alpha_{A-D}$, $\alpha_{B-D}$ and $\alpha_{C-D}$;

(4) applying the cell suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the cell suspensions of the interest present, (5) Calculating the resistance of the electrode arrays using equations (10A), (10B), (10C) and (10D) by subtracting the electronic switch resistances and the resistances of electrical connection traces from the measured resistances in step (4).

Note that in above method, the steps of exposing the electrode arrays to reference solution for the determination of the electrical resistance of electrically conductive traces (step (1), (2) and (3)) may be performed before or after the steps of applying the solutions of interest or cell suspensions of interest to the electrode arrays and measuring the total electrical resistance (step (4)). For example, step (4) may be performed first, followed by steps (1) and (2). In one approach, after step (4), the cell suspensions of the interest may be removed from the electrode array. Then reference solutions can be added to the electrode arrays. In another approach, after step (4), the cells are all lysed with some cell lysis solutions so that the electrodes are exposed to the same, reference solutions for the measurement and calculation of step (2) and (3). And then, step (5) is performed to determine the electrical resistance of electrode arrays with the cell suspensions of interest present.

The determination of the resistances of the electrical conductive traces for the electrode arrays that essentially identical electrode arrays may be, or may not be, part of the monitoring of cell-substrate impedance for cell-based assays. It depends on how the impedance data (measured at a single frequency or multiple frequencies, measured at multiple time points) of the electrode arrays is analyzed.

In some assays, one is interested in the relative change in the resistance or impedance of the electrode arrays with the cells present relative to the baseline resistance or impedance. For such cases, it is preferred to determine the resistance (or impedance) of the electrode arrays from the total, measures resistance (or impedance) by subtracting the resistance of the electrical conductive traces and the resistance of electronic switches. Thus, determination of the resistances or impedance of the electrically conductive traces may be required.

In some other assays, one is interested in the absolute changes in the resistance (or impedance) of the electrode arrays with cells present relative to the baseline resistance (or impedance). In these cases, one can directly subtract the measured resistance or impedance for the baseline condition from the measured resistance or impedance for the condition that the cells are present on the electrode arrays. The contribution of the resistance (or impedance) of the electronic switches and the resistance (or impedance) of the electrically conductive traces to the total measured resistance (or impedance) values is cancelled out in such subtractions. Thus, there is no need for determining the resistances of the electrically conductive traces.

In some assays, one is interested in calculating the Cell Index or Cell Number Index based on the monitored impedance values. Depending on which method is used for calculating the Cell Index, it may, or may not, be necessary to determine the resistances of the electrically conductive traces. For example, for the Cell Index calculation method (A) described above, the resistances of the electrically conductive traces are needed, in order to remove the effect of the resistance of the electrically conductive traces on the analysis of the relative change of the resistance or impedance. In another example, for the Cell Index calculation method (F) described above, there is no need to determine the resistances of the electrically conductive traces since the effect of the resistance of the electrically conductive traces is canceled out in the calculations.

The monitoring of the cell-substrate impedance may be or may not be based on the change with respect to the baseline impedance (or resistance). For example, a cell-based assay is performed to assess the effect of a test compound on the cells. One method in performing such an assay is by monitoring of the cell-substrate impedance and determining the change in the cell-substrate impedance before and after the addition of the test compound to the cells. The monitoring of cell-substrate impedance can be performed at a single frequency point or multiple frequency points, at a single time point or multiple time points after drug addition. For example, the impedance is first measured at a single frequency or multiple frequencies for the electrode arrays with the cells present just before addition of test compound. The test compound is then added to the cells. The impedance is then measured again at the same single frequency or multiple frequencies for the electrode arrays with the cells after the addition of test compound. Such post-compound addition measurement may be performed for many time points continuously in a regular or irregular time intervals. The change in the cell-substrate impedances can be determined or quantified by subtracting the impedance(s) (resistance and/or reactance) measured before addition of the test compound from the impedance(s) (resistance and/or reactance) measured after addition of the test compound. If the measurement is done at multiple frequencies, a single parameter or multiple parameters may be further derived for each time point after compound addition based on the calculated change in the cell-substrate impedances. Such parameters are used to quantify the cell changes after compound addition. Such approaches can be used further to analyze the responses of the cells to a test compound at multiple concentrations to derive dose-dependent response curves.

Normalized Cell Index, Delta Cell Index

A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

Cell Change Index

The time-dependent cellular response (including cytotoxicity response) may be analyzed by deriving parameters that directly reflect the changes in cell status. For example, time dependent celluler response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cytotoxicresposnes) responses may be analyzed for their higher order derivatives with respect to time. Such high order derivatives may provide additional information as for how cells responding to different compounds and as for the mechanisms of compound action.

As an example, we describe how one can to derive a parameter, called Cell Change Index, based on the real time, quantitative information (i.e., cell index, CI) about biological status of cells in the wells provided from RT-CES system. This new parameter, Cell Change Index (CCI), can effectively link time dependent cell index I with cell status, is calculated as, $$CCI(t) = \frac{dCI(t)}{CI(t) \cdot dt}. \quad (5)$$

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time. Thus, the cell index (CI) increase with time following an exponential function, such that $$CI(t) = CI(0) * 2^{\frac{t}{DT}} \quad (6)$$

where DT is the cell doubling time. For such exponential growth culture, CCI(t) is a constant, giving $$CCI(t) = \frac{0.693}{DT} \approx \frac{0.7}{DT}. \quad (7)$$

Thus, several types of CCI(t) can be classified as:
(1) If CCI is about 0.7/DT, cell index increases in the same rate as that expected for an exponential growth of the cells.
(2) If CCI>>0.7/DT, cell index increases faster than that expected for an exponential growth (or log growth) of the cells. This indicates that cells may grow faster than regular exponential growth, or cells may exhibit some morphology change (e.g. cell spreading out or adhering better to the electrode surfaces), leading to large impedance signal, or both of above effects, or there may be other cell behaviors occurring particular to the assay or culture conditions.
(3) If CCI is more than zero but somewhat smaller than 0.7/DT, then cell index increases in the rate slowed than that expected for an exponential growth. This indicates that cell growth rate may be slowed down relative to exponential growth, or cell growth may be somewhat inhibited by chemical compounds added to the culture media or by other cell culture parameters, or that certain populations of cells are dying off and detaching from the electrode surfaces, or there may be other cell behaviors occurring particular to the assay or culture conditions.
(4) If CCI is about zero, then cell index shows a near constant value. This may indicate that the cell growth is nearly-completely inhibited. For example, all the cells are arrested at certain points of cell cycle and are not progressing further. Or, this may indicate that the number of cells dying off in the culture is nearly as the number of newly-divided cells. Alternatively this may indicate that cells reach stationary phase of cell culture. Alternatively this may indicate that number of cells are above the detection upper limit of the cell-substrate impedance monitoring system. There is also the possibility of other cell behaviors occurring particular to the assay or culture conditions.
(5) If CCI is negative, then the cell index is decreasing with time, showing the cells losing attachment to the electrode surface or changing their morphology.
(6) If CCI is very negative, then the cell index decreases rapidly with time, showing that either cells lose attachment to the electrode surfaces quickly or cells change their morphology very quickly.

D. Methods for Performing Real-time Cell-based Assays

The present invention provide cell-based assays that can be performed in real time to assess cell proliferation, cell growth, cell death, cell morphology, cell membrane properties (for example, size, morphology, or composition of the cell membrane) cell adhesion, and cell motility. Thus the assays can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesivity, assays of cell-cell interactions, analysis of microbial, viral, or environmental toxins, etc.

The assays are real-time assays in the sense that cell behavior or cell status being assayed can be assessed continuously at regular or irregular intervals. Cell behaviors, cell responses, or cell status can be assayed and the results recorded or displayed within seconds to minutes of their occurrence. The cell response during an assay can be monitored essentially continuously over a selected time period. For example, a culture can be monitored every five to fifteen minutes for several hours to several days after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

Descriptions of cell-substrate monitoring and associated devices, systems and methods of use have been provided in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, entitled "Impedance based devices and methods for use in assays", filed on Jul. 18, 2003; PCT application number PCT/US03/22537, entitled "Impedance based apparatuses and methods for analyzing cells and particles", filed on Jul. 18, 2003; U.S. patent application Ser. No. 10/705,447, entitled "Impedance based devices and methods for use in assays", filed on Nov. 10, 2003; U.S. patent application Ser. No. 10/987,732 U.S. patent application Ser. No. 10/705,615, entitled "Impedance based apparatuses and methods for analyzing cells and particles", filed on Nov. 10, 2003, all incorporated herein by reference for their disclosure of cell-substrate impedance devices, systems, and methods of use. Additional details of cell-substrate impedance monitoring technology is further disclosed in the present invention.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid containers (such as wells) having electrodes fabricated on their bottom surfaces facing into the fluid containers. Cells are introduced into the fluid containers of the devices, and make contact with and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals can be measured automatically and in real time, and can be converted to digital signals for processing and for analysis.

Preferably, cell-substrate impedance assays are performed using a system of the present invention that comprises a device of the present invention, an impedance monitor, a device station that comprises electronic circuitry and engages the device and the impedance analyzer, and a software program that controls the device station and records and analyzes impedance data.

Using a system of the present invention, a cell index can optionally be automatically derived and provided based on measured electrode impedance values. The cell index obtained for a given well reflects: 1) how many cells are attached to the electrode surfaces in this well, and 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In one aspect of the present invention, a method is provided for performing cell-based assays, comprising: a) providing a cell-substrate impedance monitoring device of the present invention that comprises two or more electrode arrays, each of which is associated with a fluid container of the device; b) attaching the device to an impedance monitor; c) introducing cells into one or more fluid containers of the device; and d) monitoring cell-substrate impedance of at least one of the fluid containers that comprises an electrode array and cells. Preferably, impedance is monitored from the at least one fluid container to obtain impedance measurements at at least three time points. Preferably, impedance measurements or impedance values derived from impedance measurements from at least three time points are plotted versus time to generate one or more impedance curves for the one or more fluid containers.

In a related aspect of the present invention, a method is provided for performing cell-based assays in an impedance-monitoring system, comprising: a) providing a cell-substrate impedance monitoring system of the present invention that comprises a device having two or more electrode arrays, each of which is associated with a well of the device; b) introducing cells into one or more wells of the device; and c) monitoring cell-substrate impedance of at least one of the wells that comprises an electrode array and cells. Preferably, impedance is monitored from the one or more wells of the device to obtain impedance measurements at at least three time points. Preferably, impedance measurements or impedance values derived from impedance measurements from at least three time points are plotted versus time to generate one or more impedance curves for the one or more wells.

The method can be used to assay cell status, where cell status includes, but is not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. The cell-based assays that be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, and cell-based assays for screening and measuring ligand-receptor binding.

In preferred embodiments of this aspect of the present invention, cells are added to at least two fluid containers of a device, each of which comprises an electrode array, and impedance is monitored from at least two wells that comprise cells and an electrode array.

The cells used in the assay can be primary cells isolated from any species or cells of cell lines. Primary cells can be from blood or tissue. The cells can be engineered cells into which nucleic acids or proteins have been introduced. In some embodiments, different cell types are added to different wells and the behavior of the cell types is compared.

An impedance monitoring assay can be from minutes to days or even weeks in duration. Preferably, impedance is monitored at three or more time points, although this is not a requirement of the present invention. Impedance can be monitored at regular or irregular time intervals, or a combination of irreguliar and regular time intervals. In one embodiment of a cell-based impedance assay, the cell-substrate impedance is monitored at regular time intervals. In some embodiments of the present invention, impedance is monitored at irregular intervals and then at regular intervals during a particular time window of the assay. Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In yet another aspect, the present invention provides a method for performing real-time cell-based assay investigating the effect of a compound on cells, comprising: a) providing an above described system; b) seeding the cells to the wells of multiple-well devices; c) adding the compound to the wells containing cells; d) monitoring cell-substrate impedance before and after adding the compound at a regular or irregular time interval; wherein the time dependent impedance change provides information about time dependent cell status before addition of the compound and about time dependent cell status under the interaction of the compound. Information about cell status includes, not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

In one embodiment of the above cell-based assay, the cell-substrate impedance is monitored at regular time intervals. In exemplary embodiments, the impedance is measured at a regular 2 hour, 1 hour, 30 min or 15 min time interval before and after adding the compound. In the present application, a real-time assay means that one can perform the measurement on cell-substrate impedance with various time resolutions, for example, measurement taking place at a longer time interval such as every hour or every two hours, or at a shorter time interval every minute or a few minutes. Real-time assay does not mean that the measurements are provided in a continuous, uninterrupted fashion. In another word, real-time assay does not mean that the measurements are performed at every single moment.

Figure 2:
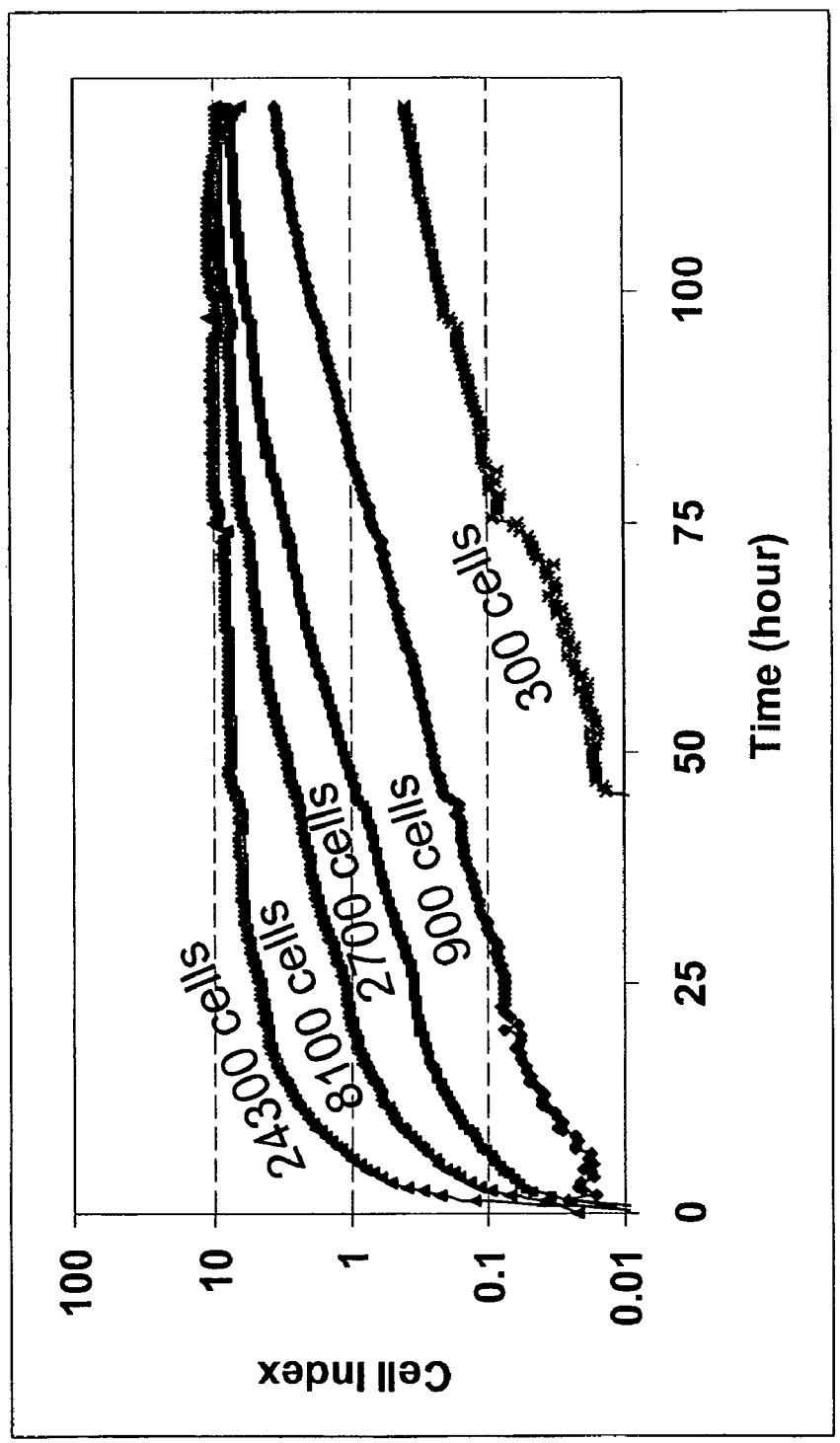
FIG. 2 shows real-time monitoring of proliferation of H460 cells seeded at different initial cell seeding numbers on a cell substrate impedance monitoring system of the presnet invention. The cell proliferation was continuously recorded every 15 minutes for over 125 hours. The cell growth curves in the log scale show exponential cell growth or cells in the stationary phase.

FIG. 2 depicts results of the use of methods of the present invention to monitor cell proliferation. In this experiment, H460 cells were introduced into wells of a 16 well device (16× E-Plate) of a cell-substrate impedance monitoring system of the present invention, with different wells receiving different initial cell seeding numbers. The device was engaged with a device station of the system that was in a tissue culture incubator that kept a temperature of 37 degrees C. and an atmosphere of 5% $CO_2$. Cell-substrate impedance was monitored at 15 minute intervals for 125 hours. The cell index was calculated by the system for each time point and displayed as a function of time to give cell growth (proliferation) curves for each cell seeding number. The cell growth curves were plotted on a log scale showing exponential growth phases and stationary phases.

Figure 3:
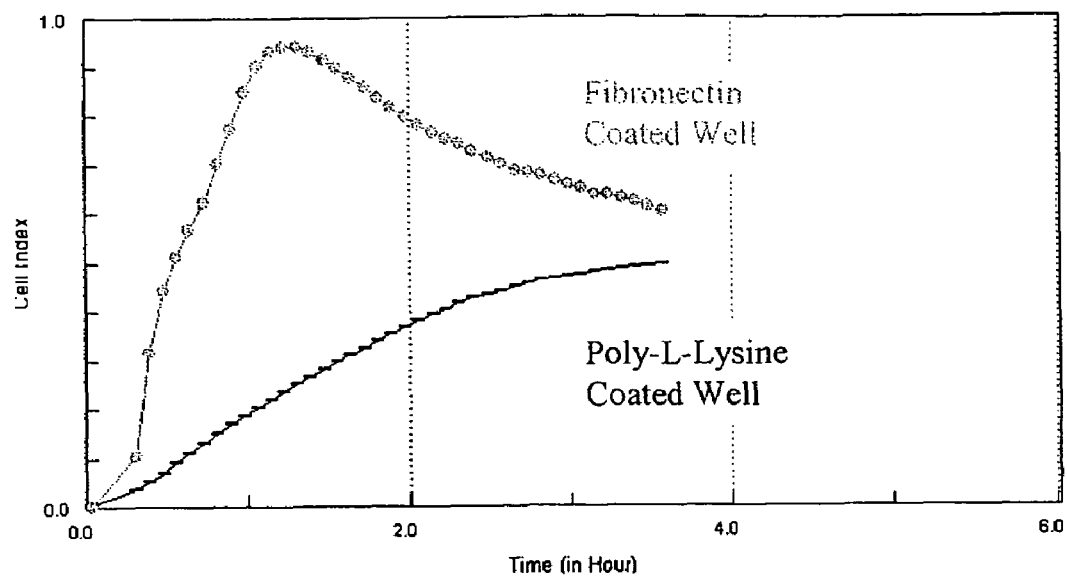
FIG. 3 shows real time monitoring of cell attachment and spreading of NIH3T3 cells using a cell-substrate imepdnace monitoring system of the presnet invention. The cells were seeded onto devices coated with either poly-L-lysine or fibronectin. The cell attachment and cell spreading processes on the different coating surfaces were monitored every 3 minutes for over 3 hours in real time.

FIG. 3 depicts results of real-time monitoring of cell attachment and spreading of NIH3T3 cells. The cells were seeded onto cell-substrate impedance monitoring devices of the present invention that were coated with either poly-L-lysine or fibronectin. The device was connected to a device station that was in a tissue culture incubator that kept a temperature of 37 degrees C. and an atmosphere of 5% $CO_2$. Cell attachment and cell spreading on the difference coating surfaces were monitored by measuring impedance on the cell-substrate monitoring system. Impedance was monitored in real time every 3 minutes for 3 hours. The cell index for each time point was calculated by the impedance monitoring system and plotted as a function of time.

Figure 4:
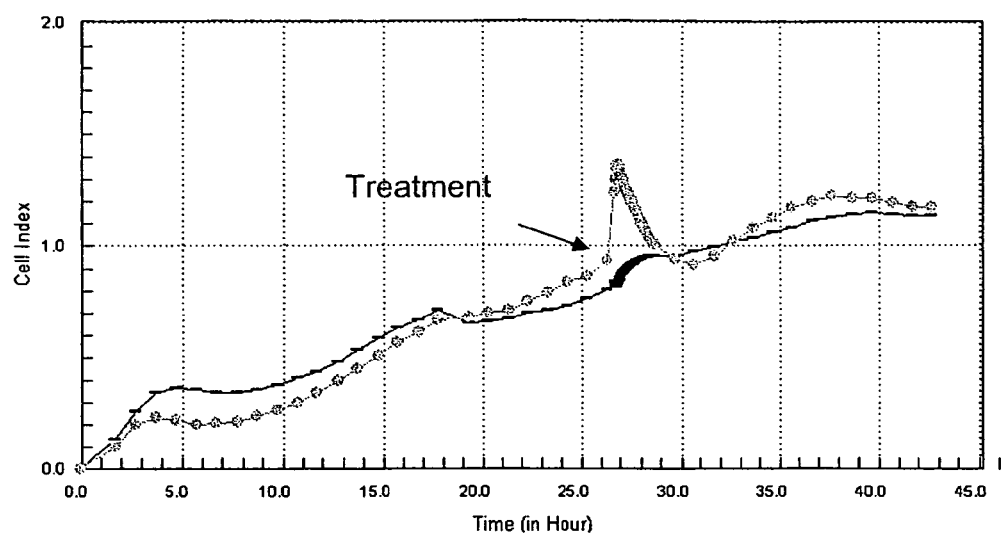
FIG. 4 shows real-time monitoring of morphological changes in Cos-7 cells uisng a cell-substrate impedance monitoring system of the presnet invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation.

FIG. 4 shows the results of an experiment monitoring morphological changes in Cos-7 cells in response to stimulation with epidermal growth factor (EGF). Cells were seeded in wells of a 16 well monitoring device (16× E-Plate) of the present invention that engaged a device station of a cell-substate monitoring system. The device station was positioned in an incubator held at 37 degrees C. and 5% $CO_2$. The cells were serum starved for 8 hours and then stimulated with 50 nanograms/mL of EGF. Control cells did not receive EGF. Impedance was monitored at 3 minute intervals for 2 hours and then at 1 hour intervals for 14 hours. The cell index was calculated by the system and plotted as a function of time. An initial jump in cell index is seen in EGF-treated cells due to membrane ruffling and actin dynamics in response to EGF. The arrow indicates the point of EGF addition.

D.1. Cell Proliferation Assays

The present invention provides methods for performing cell proliferation assays. In these assays, an increase in monitored impedance is indicative of an increases cell number. The impedance measurements or impedance values derived from impedance measurements can be plotted versus time to obtain growth curves for cells growing in a fluid container of a cell-substrate monitoring device of the present invention.

The present invention provides a method of generating at least one cell growth curve, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at three or more time points after adding the cells to the one or fluid containers; and plotting the impedance measurements or values for the three or more time points versus time to generate at least one growth curve for the cells in the one or more fluid containers.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells to one or more wells of the system; monitoring impedance from the one or more wells to obtain impedance measurements at three or more time points after adding cells to the one or more wells; and plotting impedance measurements or impedance values for the three or more time points versus time to generate a growth curve for the cells in the one or more wells.

Preferably, using a device or system of the present invention, impedance is monitored at four or more time points, in which at least one of the four or more time points is measured from a fluid container prior to adding cells to the fluid container. Preferably, impedance is monitored at regular or irregular time intervals for an assay period of from minutes to days. In many cases, proliferation assays can be performed by monitoring impedance for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

A growth curve can be generated by plotting impedance measurements versus time, or by plotting cell index values that are calculated from impedance measurements, such as normalized cell index values or delta cell index values versus time. The impedance measurement or cell index axis (typically the y-axis) can optionally use a log scale.

An impedance value can be any indices of impedance derived from impedance measurement, including, as nonlimiting examples, a cell index, a normalized cell index or a delta cell index. In certain embodiment, impedance value can also be a "raw" measured or monitored impedance value. Cell index (including normalized and delta cell index) can be a useful value for plotting growth curves, as it relates impedance measurements to cell number. For cell growth curves, a delta cell index for a given time point can be derived by subtracting the cell index at a baseline point, such as a time point after cell attachment and just before log phase growth, from the cell index measurement at the given time point. Preferably, determinations of impedance values and generating growth curves based on impedance measurements or values can be performed by software, and preferably by software that interfaces directly with the impedance analyzer. For example, where the growth assays are performed by a system of the present invention, impedance values (where used) can be measured or derived or calculated and growth curves generated by a software program that controls and receives data from the impedance analyzer.

A growth curve generated from impedance measurements or cell index values (including normalized cell index values and delta cell index values) can optionally be used to calculate one or more kinetic parameters of cell growth or behavior. For example, a growth curve can be used to calculate the length of a lag phase, cell attachment time, cell attachment rate, or a cell doubling time.

FIG. 2 shows real-time monitoring of proliferation of H460 cells seeded at different initial cell seeding numbers on a cell substrate impedance monitoring system of the presnet invention. The cell proliferation was continuously recorded every 15 minutes for over 125 hours. The cell growth curves in the log scale show exponential cell growth or cells in the stationary phase. The cell index curve shown here can be used to calculate cell doubling time (DT). For example, taking the cell index for initial seeding density of 900 cells. It took appoximately 57 hrs (from about 55 hr to about 112 hr) for cell index to increase from 0.3 to 3.0. Thus, the cell index doubling time is about 17.2 hrs (=log(2)*57). Assuming that there is a linear correlation between cell number and cell index in this range, then cell doubling time is the same as the cell index doubling time. Thus, the cell doubling time (DT) is about 17.2 hrs. Another simple method to calculate the cell index doubling time is just to figure out how long t takes cell index to double. For example, for the cell index curve with initial seeding density of 900 cells. It took about 17 hrs for cell index to change from 1.0 (at about 82 hrs) to 2.0 (at about 99 hrs). Thus the clel index doublimng time is 17 hrs.

FIG. 3 shows real time monitoring of cell attachment and spreading of NIH3T3 cells using a cell-substrate imepdnace monitoring system of the presnet invention. The cells were seeded onto devices coated with either poly-L-lysine or fibronectin. The cell attachment and cell spreading processes on the different coating surfaces were monitored every 3 minutes for over 3 hours in real time. Using the cell index curve showing in FIG. 3, we can calculate the cell attachment time and cell attachment rate. Initial cell index increase immediately following cell addition to the ells (at time=0 in FIG. 3) reflects the cell spreading and attachment process. The time it takes for cell index to increase from zero to a maximum value or a some-what constant value (assuming that there is no cell division or growth in this initial time period following cell seeding) is the cell attachment time. For NIH3T3 cells, cell attachment time in a fibronectin coated well is about 1.2 hrs, as compared with the attachment time of about 3.5 hrs for the same cells in a poly-L-lysine coated well. Cell attachment rate is defined as 1 over the cell attachment time. Thus, cell attachment rate is about 0.83 $hr^{-1}$ and about 0.29 $hr^{-1}$, respectively, for NIH3T3 cells attaching to a fibronectin-coated well and a poly-L-lysine coated well.

FIG. 4 shows real-time monitoring of morphological changes in Cos-7 cells uisng a cell-substrate impedance monitoring system of the presnet invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation. Using the cell index curve showing in FIG. 4, we can calculate the cell attachment time and cell attachment rate. Initial cell index increase immediately following cell addition to the ells (at time=0 in FIG. 4) reflects the cell spreading and attachment process. The time it takes for cell index to increase from zero to a maximum value or a some-what constant value (assuming that there is no cell division or growth in this initial time period following cell seeding) is the cell attachment time. For Cos-7 cells shown here, the cell attachment time is about 4 hrs. Cell attachment rate, as defined: 1 over the cell attachment time, is about 0.25 $hr^{-1}$ for Cos-7 cells. Furthermore, we can also calculate the length of lag phase. The lag phase corresponds to the time it takes for cells to enter the growth phase after the completion of cell attachment process. Based on the cell index curve in Figure, cell attachment was complete at about 4 hrs. The cells showed significant increase in cell index—indicating cell growth, at around 9 hrs. Thus, the length of lag phase is about 5 hrs (=9 hr-4 hr).

Comparing Growth Curves of Two of More Cell Types

Two or more cell types can be seeded to separate wells in a proliferation assay using the methods of the present invention to generate growth curves of the two or more cell types. The growth curves or kinetic parameters derived from the growth curves of the cell types can be compared.

In this aspect, the invention includes a method of generating growth curves for at least two cell types, comprising: providing a device of the present invention having two or more electrode arrays, each of which is associated with a fluid container of the device; attaching the device to an impedance analyzer; adding cells of two or more cell types to two or more fluid containers of the device, in which at least one of the two or more fluid containers receives one cell type and at least one other of the two or more fluid containers receives a different cell type, to provide two or more fluid containers comprising two or more different cell types; monitoring impedance from the two or more fluid containers comprising different cell types at three or more time points after adding the two or more cell types to the two or more fluid containers; and plotting impedance measurements or impedance values for the three or more time points versus time to generate a growth curve for the two or more cell types.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells of two or more cell types to two or more wells of the device, in which at least one of the two or more wells receives one cell type and at least one other of the two or more wells receives a different cell type, to provide two or more wells comprising two or more different cell types; monitoring impedance from the two or more wells comprising different cell types at three or more time points after adding the two or more cell types to the two or more wells; and plotting impedance measurements or impedance values for the three or more time points versus time to generate a growth curve for the two or more cell types.

As, described above for proliferation assays, impedance is preferably monitored using an impedance monitoring device or system at four or more time points, in which at least one of the four or more time points is measured from fluid containers prior to adding cells to the fluid containers. Preferably, impedance is monitored at regular or irregular time intervals for an assay period of from minutes to days, for example, for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

Growth curves for different cell types can be generated as described above. Impedance or impedance values, such as cell index, normalized cell index, or delta cell index can be plotted versus time. The impedance measurement or cell index axis (typically the y-axis) can optionally use a log scale.

A growth curve generated from impedance measurements or cell index values (including normalized cell index values and delta cell index values) can optionally be used to calculate one or more kinetic parameters of cell growth or behavior. For example, a growth curve can be used to calculate the duration of a lag phase, cell attachment time, cell attachment rate, or a cell doubling time.

Preferably, the growth curves of the two or more different cell types, or kinetic parameters derived from the growth curves of the two or more different cell types, are compared to determine differences among the cell types in proliferation patterns or rates, or in kinetic parameters that can be derived from growth curves. The different cell types used can be any cell types, including primary cells isolated from blood or tissue of an animal or human, or cells from cell lines. For example, proliferation rates of two types of primary cancer cell can be compared, or of primary cancer cells of the same type but different grades. In another example, primary cells of individuals of different genotypes can be compared. In another example, proliferation rates of primary or cell line stem cells can be compared. In yet another example, growth curves or parameters of control and genetically modified cells of a cell line can be compared. In yet another example, growth curves or parameters of cells infected with virus and control cells can be compared.

D.2. Quantifying Cells Using Cell-Substrate Impedance Devices

The present invention also includes a method of quantifying cells, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at one or more time points after adding the cells to the one or more fluid containers; deriving a cell index for the one or more time points; and using the cell index to determine the number of cells in the one or more fluid containers at at least one of the one or more time points. The cell index is used to determine the number of cells using a formula that relates cell index to cell number, in which the formula is obtained by: providing a device for cell-substrate monitoring, attaching the device to an impedance monitor; adding cells to one or more fluid containers of the device; measuring impedance of the one or more fluid containers comprising cells; calculating a cell index from the impedance measurements; determining the number of cells of said at least one fluid container at the time of impedance monitoring by a means other than impedance monitoring; and deriving a formula that relates the number of cells of the one or more fluid containers at the two or more time points with the impedance measurements at the two or more time points.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, or Coulter counting.

The method can also be practiced using an impedance monitoring system of the present invention, where the system includes a multi-well cell-substrate impedance monitoring device, an impedance analyzer, a device station, and a software program. The method includes; providing a multi-well cell-substrate impedance measuring system; adding cells one or more wells of the system; monitoring impedance from the one or more wells comprising cells at one or more time points after adding the cells to the one or more wells; deriving a cell index for the one or more time points; and using the cell index to determine the number of cells in said at least well at at least one of said one or more time points.

The cell index is used to determine the number of cells using a formula that relates cell index to cell number, in which the formula is obtained by: providing a system for cell-substrate monitoring, where the system comprises at least one multi-well cell-substrate impedance monitoring device, adding cells to one or more wells of a device of the system; measuring impedance of the one or more wells comprising cells at two or more time points; calculating a cell index from the impedance measurement at the two or more time points; determining the number of cells of the one or more wells at the two or more time points by a means other than impedance monitoring; and deriving a formula that relates the number of cells of the one or more wells at the two or more time points with the impedance measurements at the two or more time points.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemacytometer counting, flow cytometry, or Coulter counting.

Formulas relating cell index (including normalized cell index and delta cell index, which can also be used) to cell number for a given cell type can be used to quantitate cells of that type in assays using a cell-substrate impedance monitoring device, such as a device described herein. Generally, for a give cell type and for cells under similar physiological conditions, the derived formulas relating cell index to cell number can be used in subsequent assays. There is no need to obtain the formula each time when an assay is performed. However, it is worthwhile to point that the formula can only be valid as long as the cells are under same physiological conditions in the assays where the formula was derived and where the formula is used. If the cell condition is different, for example, the composition of culture media is changed, or the cell attachment surface is altered, then the formula will not hold. In another example, if cells are in log-growth phase in one assay and are in stationary phase in another assay, then the formula may not hold. Another point worth mentioning here is that relates the fact the derived cell index or impedance also depends on cell attachment quality on the surface as well as cell morphology. If cell morphology or cell attachment changes during an assay, then one need to distinguish between the changes caused by change in cell number or in cell morphology or in cell attachment.

Figure 8:
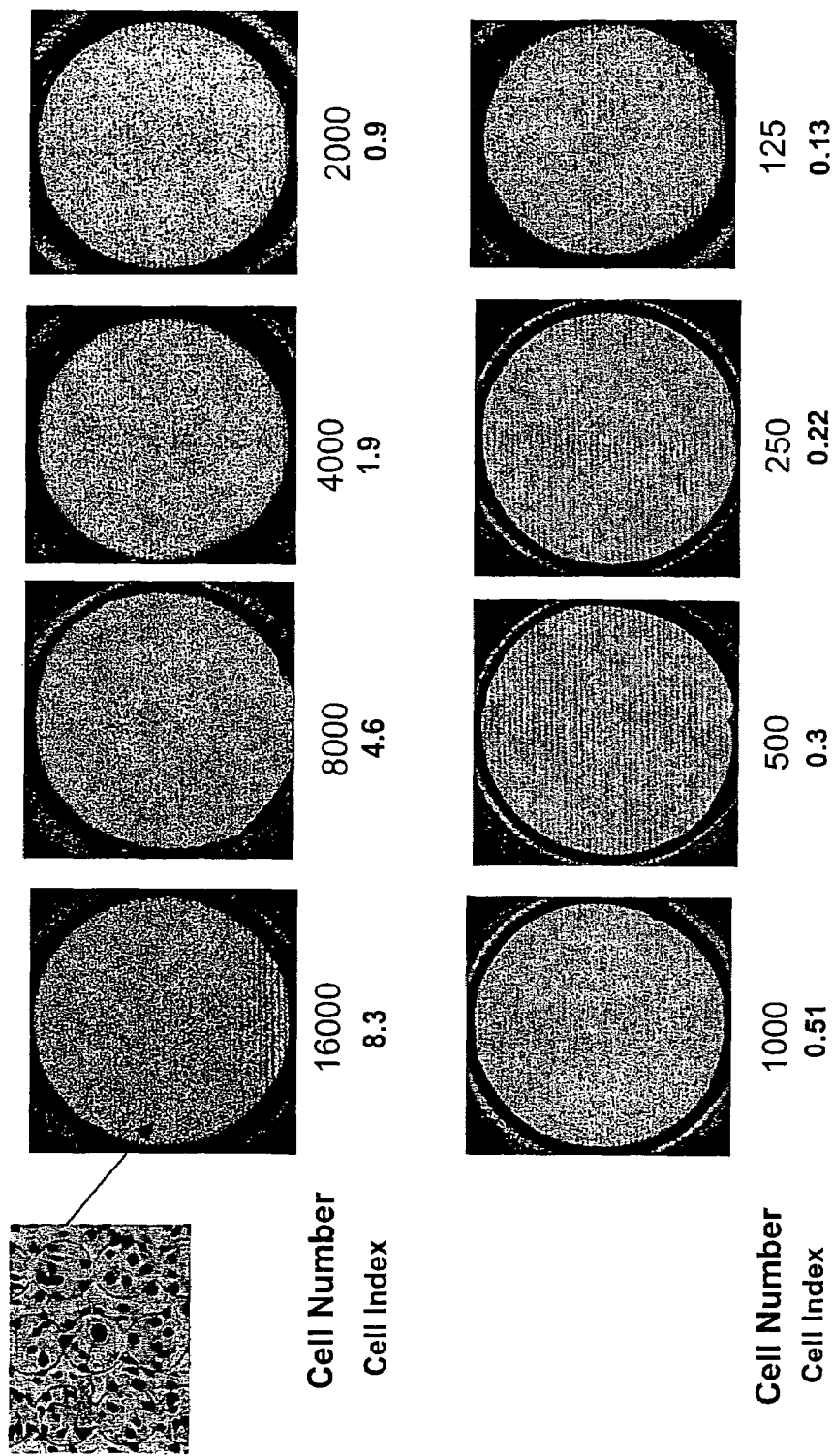
FIG. 8 shows titration of NIH3T3 cells on the devices of the present invention. The indicated cell number of cells were seeded into microtiter devices fabricated with electronic sensor arrays shown in FIG. 1B. The electronic sensor arrays were-precoated with fibronectin. Two hours after seeding, the cell index number was determined using a cell-substrate imepdnace monitoring system of the present invention.

As an example, we can derive the correlation formula between cell index and cell number for NIH3T3 cells under the experimental conditions. The formula for converting cell index to cell number for this particular case is: Cell number=2000*Cell index−145. To test this formula, we found the error in estimating cell number based on the cell index data shown in FIG. 8 as compared to the seeded cell number is less than 20%.

D.3. Cell-based Assays to Test the Effects of Compounds on Cells

In yet another aspect, the present invention provides a method for performing a cell-based assay investigating the effect of one or more test compounds on cells, comprising: providing a device of the present invention having two or more electrode arrays, each of which is associated with a fluid container of the device; attaching the device to an impedance analyzer; introducing cells into two or more fluid containers of the device that comprise an electrode array; adding at least one test compound to at least one of the one or more of the fluid containers comprising cells and an electrode array to provide at least one test compound fluid container; providing at least one control fluid container to which cells are added that does not receive test compound; and monitoring cell-substrate impedance of the one or more test compound fluid containers and the one or more control fluid containers at at least three time points after adding the one or more test compounds, and analyzing impedance measurements from the one or more test compound fluid containers and the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes; providing a multi-well cell-substrate impedance measuring system; introducing cells into two or more wells of the device; adding at least one test compound to at least one of the one or more of the wells comprising cells to provide at least one test compound well; providing at least one control well to which cells are added that does not receive test compound; monitoring cell-substrate impedance of the one or more test compound wells and the one or more control wells at at least three time points after adding the one or more test compounds; and analyzing impedance measurements from the one or more test compound wells and the one or more control wells at at least three time points after adding the one or more test compounds, in which changes in impedance can provide information about cell responses to the one or more test compounds.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown.

Information about cell responses to the one or more test compounds includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance.

The cells used in the assay can be primary cells isolated from any species or can be cells of cell lines. The cells can be genetically engineered cells (For example, cells from a genetically modified organism, such as for example from a "gene knockout" organism, or cells that have been engineered to over-express an endogenous gene or a transgene, or cells whose normal gene expression has been manipulated by use of antisense molecules or silencing RNA.) In some embodiments, different cell types are added to different wells and the behavior of the different cell types in response to one or more compounds is compared.

The cell-based assays that be performed with above methods include, but are not limited to, cell adhesion, apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral, bacterial, or environmental toxin mediated cell pathologic changes or cell death, detection or quantification of neutralizing antibodies, specific T-cell mediated cytotoxic effect, and cell-based assay for screening or measuring ligand-receptor binding.

In the methods of the present invention that investigate test compound effects on cells, impedance is preferably monitored from at least one test compound well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

It is preferable to perform replicate test compound assays in which more than one fluid container of cells receives the same compound at the same concentration. In this case, impedance measurements or values can be averaged for the assayed time points for replicate wells. Preferably, a standard deviation for the averaged values is also calculated.

In the methods of the present invention, analyzing impedance can comprise plotting cell impedance versus time to obtain at least one test compound impedance curve and at least one control impedance curve. Preferably, at least one test compound impedance curve and said at least one control impedance curve are compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Preferably, data from impedance monitoring of a well that comprises cells and a test compound is compared with data from impedance monitoring of a well that comprises cells in the absence of a test compound, however, this is not a requirement of the present invention. For example, it is also possible to compare impedance measurements from one or more time points prior to the addition of compound to compare impedance measurements from one or more time points after the addition of compound. Such comparisons can be used directly to assess the cells' response to a compound. It is also possible to calculate a cell index (or cell number index) using the impedance values obtained.

Methods of calculating a cell index (cell number index) are disclosed herein as well as in parent application U.S. patent application Ser. No. 10/705,447, U.S. patent application Ser. No. 10/987,732, both herein incorporated by reference for disclosures relating to cell number index and its calculation. The cell index calculated from impedance measurements of wells receiving compound can be compared with the cell index calculated from impedance measurements of control wells to assess the effect of a compound on cells. Alternatively, cell index calculated from impedance measurements of wells from one or more time points after the addition of a compound can be compared with the cell index calculated from impedance measurements of wells from one or more time points prior to the addition of a compound to assess the effect of a compound on cells. In some preferred embodiments, the cell index can be used as an indicator of cytotoxicity.

The derivation of cell index from impedance measurements is provided in Section C of the present application. Cell index values (including normalized cell index values and delta cell index values) from at least three time points from at least one test compound well and at least one control well can be plotted versus time to obtain one or more test compound cell index curve and one or more control cell index curves. The one or more test compound cell index curves and the one or more control cell index curves can be compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Cell index values at three or more assay time points for one or more test compound wells and one or more control wells can be used to derive cell change index (CCI) values or a second order derivatives of cell index at three or more assay time points. The calculation of cell change index is provided in Section C of the present application. The value of CCI at a give time point can be determined to be either approximately equal to 0.7, much greater than 0.7, greater than zero and less than 0.7, approximately equal to zero, less than zero, or much less than zero. These values can indicate cell behavior at an assay time point, as CCI approximately equal to 0.7 indicates log rate growth, a CCI much greater than 0.7 indicates faster than log rate growth, a CCI greater than zero and less than 0.7 indicates slower than log rate growth, a CCI approximately equal to zero indicates no growth (a constant cell index), a CCI less than zero indicates cells are detaching from the substrate, and a CCI much less than zero indicates cell are detaching rapidly from the substrate.

For a given assay time point, differences in CCI value between control and compound treated wells can indicate a time at which the compound has an effect on cells, as well as providing information on the type of effect the compound has.

The CCI can further be used to obtain information on the effect of a test compound by plotting CCI versus time for at least three assay time points to obtain a cell change index curve (CCI curve) for at least one control container or well and at at least one test compound container or well. One or more test compound CCI curves can be compared with one or more control CCI curves to obtain information on cell status or behavior in response to said at least one test compound, wherein said cellular status or behavior is at least one of: cell attachment or adhesion status; cell growth or proliferation status; the number of viable cells or dead cells; cytoskeleton change or re-organization; or the number of cells going through apoptosis or necrosis.

Cell-based Assays with More than One Cell Type

The present invention also provides methods of comparing the effects of a compound on two or more cell types. In one aspect, the method comprises: providing a device of the present invention having two or more electrode arrays, each of which is associated with a fluid container of the device; attaching the device to an impedance analyzer; introducing cells into two or more fluid containers of the device that comprise an electrode array, wherein at least one of the two or more fluid containers receives one cell type and at least one other of the two or more fluid containers receives a different cell type; adding a test compound to the one or more fluid containers receiving one cell type and adding the test compound to the one or more fluid containers receiving a different cell type to provide at least two test compound fluid containers that comprise cells of different types; providing at least two control fluid containers that do not receive test compound, in which at least one of the control fluid containers receives cells of the one type and at least one of the control fluid containers receives cells of the different type; monitoring cell-substrate impedance of the two or more test compound fluid containers that comprise different cell types and the one or more control fluid containers at at least three time points after adding the one or more test compounds; and analyzing impedance measurements from the two or more test compound fluid containers comprising different cell types and from the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells using a cell-substrate impedance monitoring system of the present invention, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes: providing a multi-well cell-substrate impedance measuring system; introducing cells into two or more wells of the device that comprise an electrode array, wherein at least one of the two or more wells receives one cell type and at least one other of the two or more wells receives a different cell type; adding a test compound to the one or more wells receiving one cell type and adding the test compound to the one or more wells receiving a different cell type to provide at least two test compound wells that comprise cells of different types; providing at least two control wells that do not receive test compound, in which at least one of the wells receives cells of the one type and at least one of the control wells receives cells of the different type; monitoring cell-substrate impedance of the two or more test compound wells that comprise different cell types and the one or more control wells at at least three time points after adding the one or more test compounds; and analyzing impedance measurements from the two or more test compound wells comprising different cell types and from the one or more control wells at at least three time points after adding the one or more test compounds, in which changes in impedance can provide information about cell responses to the one or more test compounds.

In the methods of the present invention that investigate test compound effects on cells, impedance is preferably monitored from at least two test compound wells comprising different cell types at at least one time point before adding test compound to the at least one two compound wells. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

As disclosed in an earlier section on compound assays, a test compound can be any compound whose effect on cells can be investigated. A test compound used in assays comparing cell responses can be a compound whose effect on one or more of the cell types to be assayed is known, or can be a compound whose effects on any of the cell types to be assayed are unknown. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells.

As disclosed in a previous section for compound assays, the cell types used in the assay can be primary cells isolated from any species or can be cells of cell lines. In some preferred embodiments, the different cell types are the same type of cell from different individuals, and thus have different genotypes. One or more of the cell types can be genetically engineered (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In these cases, genetically modified cells can be compared with control cells. In another example the cells can be, for example, stem cells from different stages of differentiation or of different genotypes whose response to growth factors is being compared. In other examples the cells can be cancer cells where the test compound is tested for its cytotoxic effects. The cells can be primary cancer cells of the same type isolated from different individuals, for example, or different cancer cell lines, or cancer cells of the same type but of different grades. In some embodiments, three or more different cell types are added to different wells and the behavior of the three or more different cell types in response to one or more compounds is compared. In preferred embodiments of the present invention, for each cell type tested there is a control performed in which the control does not receive test compound.

A variety of assays can be employed, where the effect of a test compound on the behavior of two or more cell types in the assay is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Preferably, time-dependent responses of the first and second types of cells are compared to see how similar or different the responses from the two types of cells are. In one method of the present invention, impedance from a first cell type well is plotted versus time to give a first cell type impedance curve and impedance from a second cell type well is plotted versus time to give a second cell type impedance curve. Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of a cells response to a compound are similar or different. Preferably, impedance curves or cell index curves generated from control wells comprising each cell type in the absence of compound are compared with the test compound curves to assess the compound-specific effects on each cell type. The effects of the compounds on one or more of the two or more cell types can be effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect of a compound on at least one of the cell types used in the assay may be known. The mechanism of action of a compound on at least one of the cell types used in the assay may be known. In such cases, comparison of the compound response of one or more different cell types with the compound response of a cell type whose response to the compound is characterized can give information as to the similarity or difference in response of a different cell type to the compound.

In one preferred embodiment of this method, time-dependent cytotoxic responses of particular cell types to a compound are compared. Cytotoxicity assays can provide information on the sensitivity of one or more cell type to a compound.

Figure 9A:
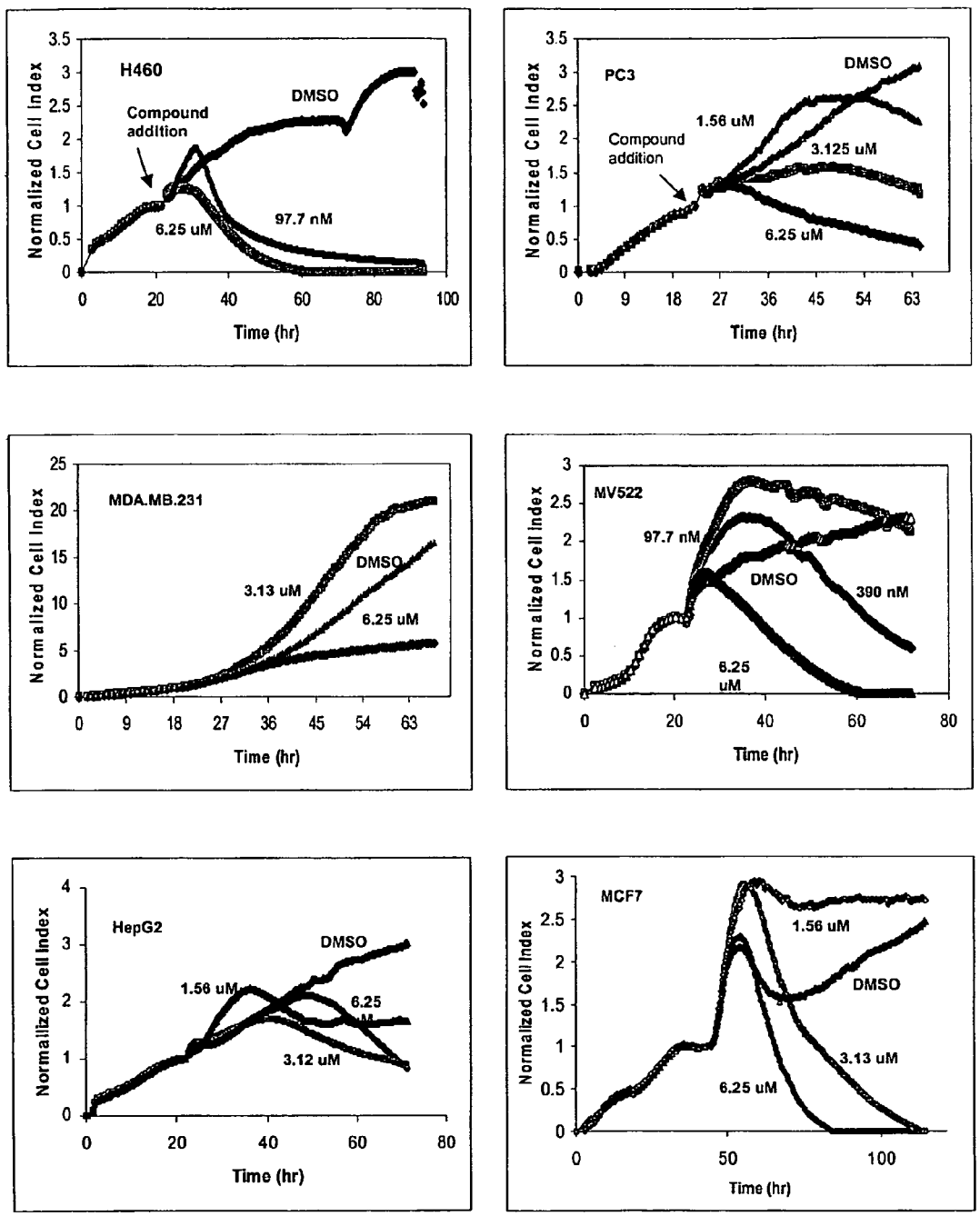
FIGS. 9A and B shows the responses of various cell types (listed in Table 1) to doxorubicin treatment as monitored using a cell-substrate imepdnace monitoring system of the presnet invention. The indicated cell lines were seeded onto microtiter devices fabricated with electronic sensor arrays shown in FIG. 1B. The cellular responses were continuously monitored at 15 or 30 or 60 minutes time interval before and after treatment with doxorubicin.
Figure 9B:
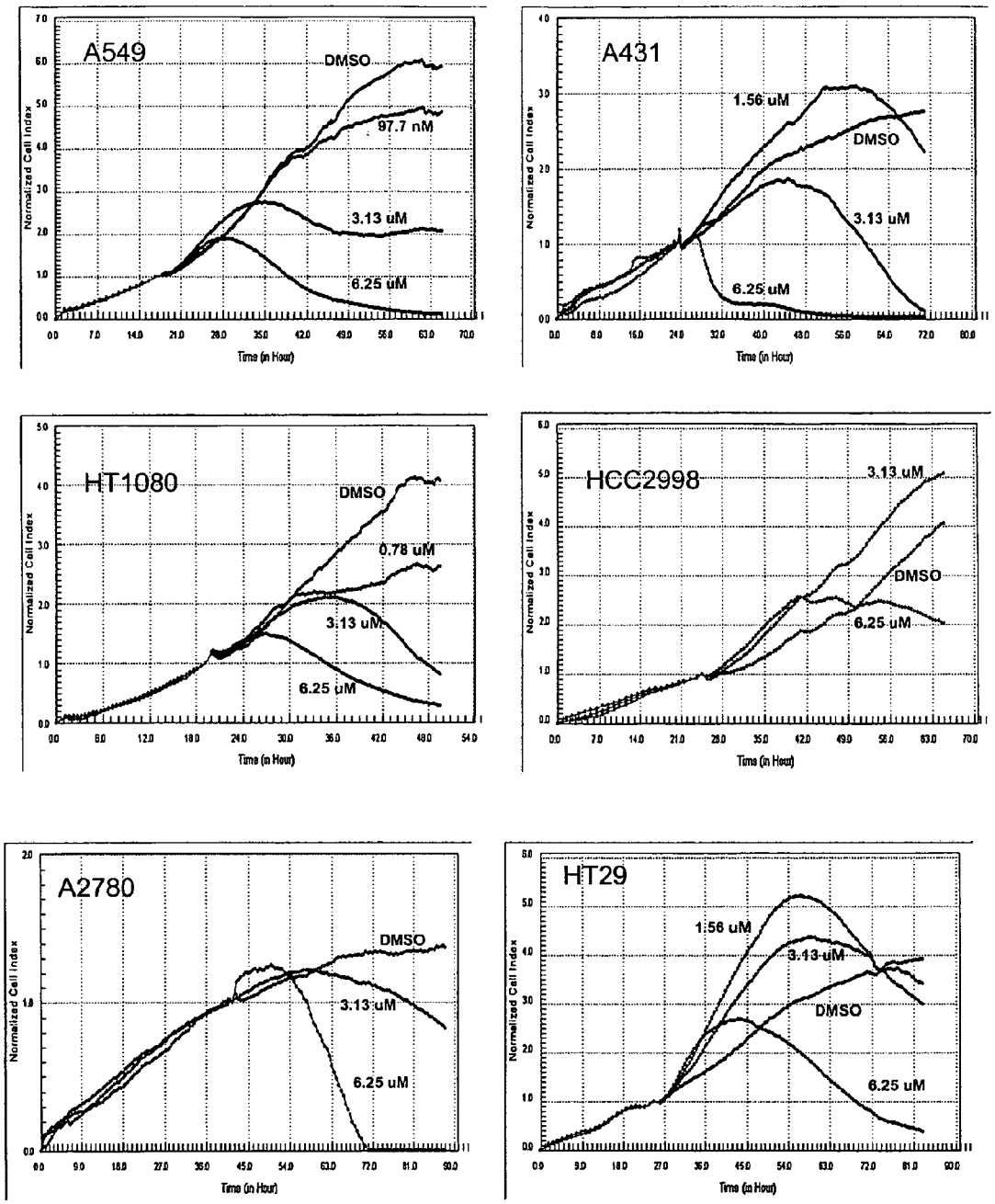
Figure 10A:
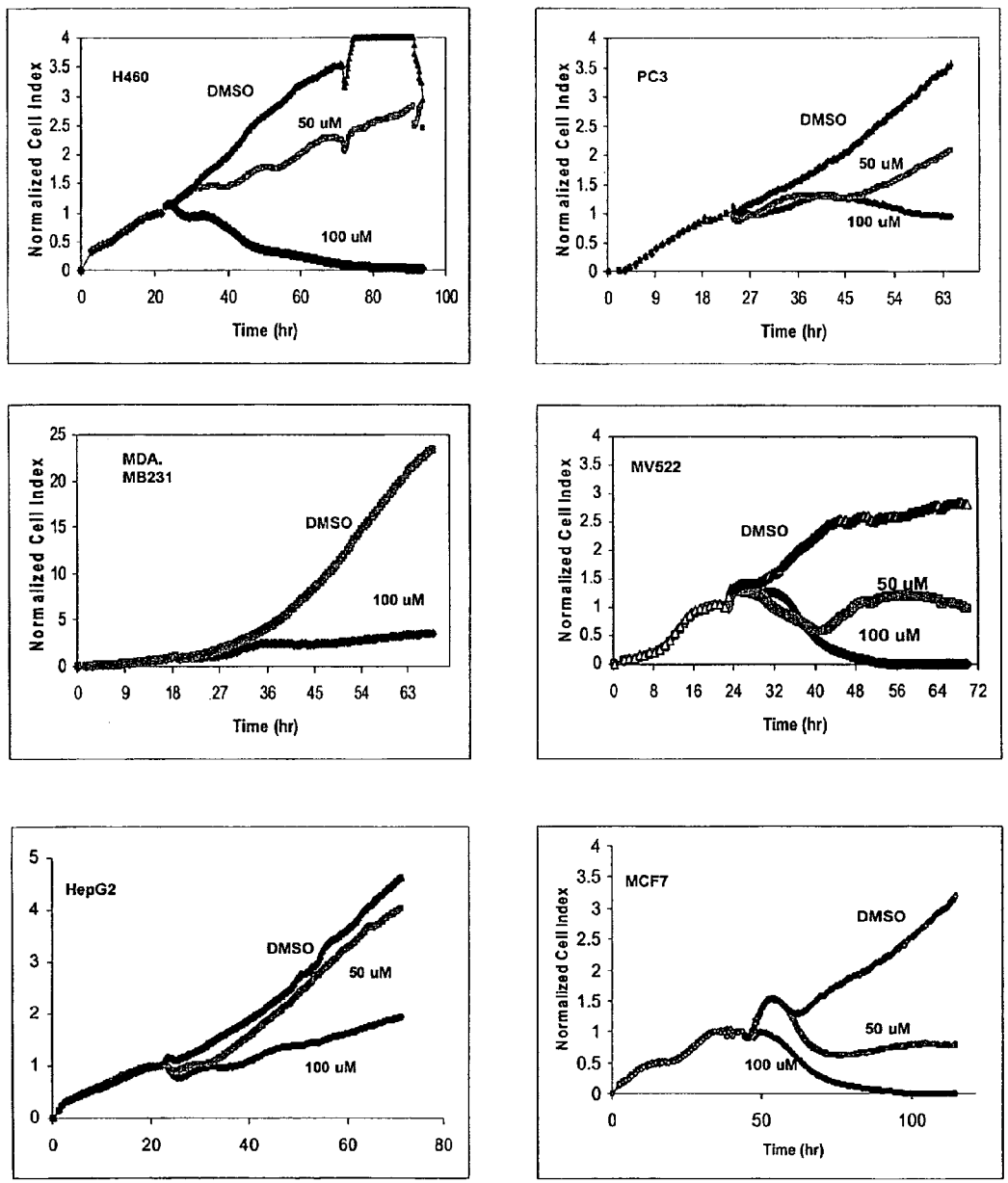
FIGS. 10A and B shows the responses of various cell types (listed in Table 1) to olomoucine treatment as monitored using a cell-substrate imepdnace monitoring system of the presnet invention. The indicated cell lines were seeded onto microtiter devices fabricated with electronic sensor arrays shown in FIG. 1B. The cellular responses were continuously monitored at 15 or 30 or 60 minutes time interval before and after treatment with olomoucine.
Figure 10B:
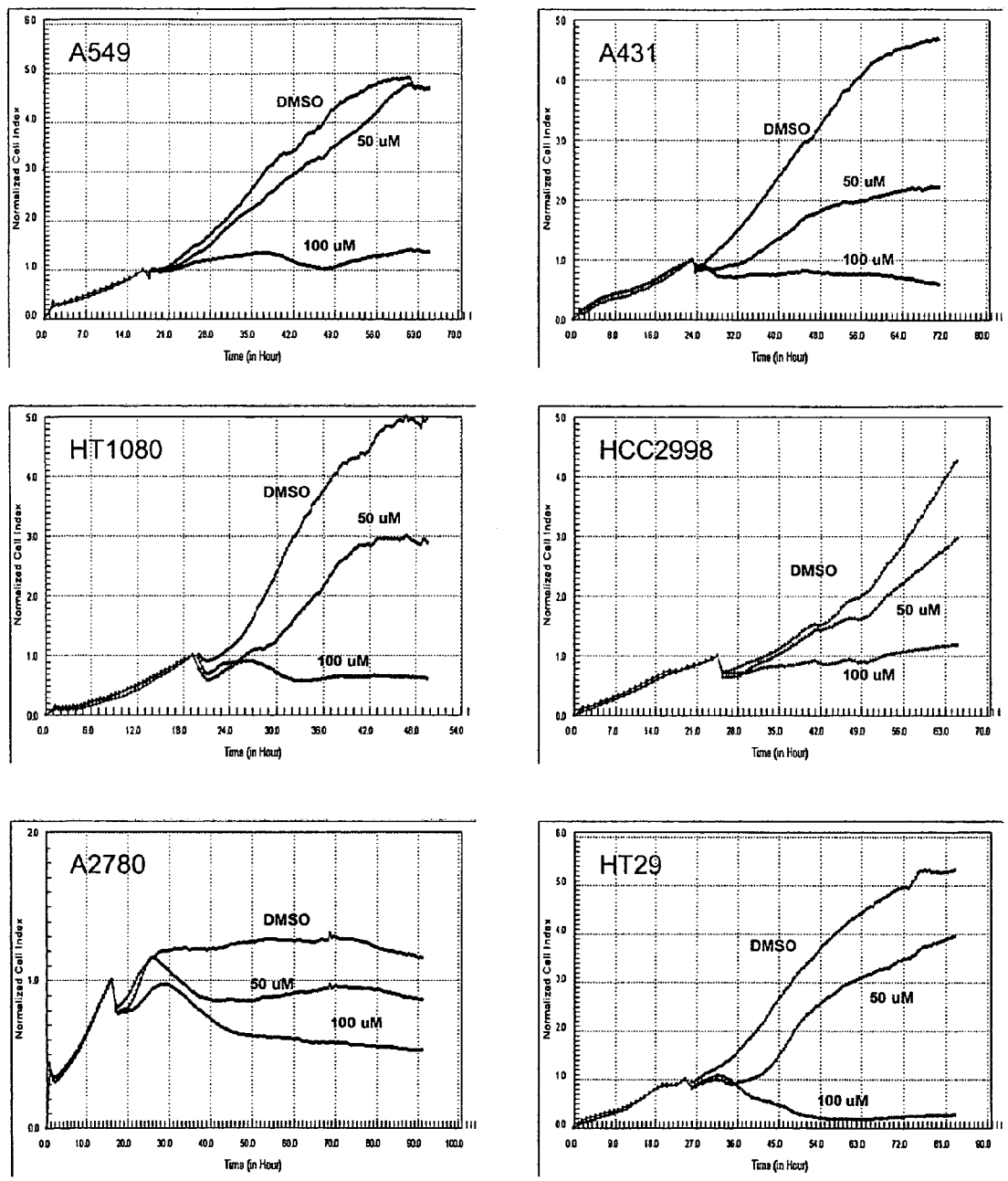

FIGS. 10A and B show the responses of various cell types (listed in Table 1) to olomoucine treatment as monitored using a cell-substrate imepdnace monitoring system of the presnet invention. The indicated cell lines were seeded onto microtiter devices fabricated with electronic sensor arrays shown in FIG. 1. The cellular responses were continuously monitored at 15 or 30 or 60 minutes time interval before and after treatment with olomoucine. Comparison among these cell index curves showed that certain similarity does exist. Take the treatment of olomoucine at 100 uM as an example. For a significant number of cell types tested, olomoucine treatment resulted in a near-constant cell index for some length of time (for example: 10, 20 or 30 hrs) a long time. This relates to the fact olomoucine is a cell cycle resting compound and for some time period following compound addition, cells do not divide any more and so cell number does not change but cells remain "live". Thus, for such time period, cell index did not change with time. The "near-constant" cell index curves were also observed for cells treated with roscovitine, which is another compound causing cell cycle arrest. The cell index curves shown in FIGS. 10A and 10B are strikingly different from the cell index curves shown in FIGS. 9A and 9B, and FIGS. 11A and 11B, where compounds follow different mechanism of compound action.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

Cell-based Assays with More than One Compound

The present invention also provides methods of comparing the effects of two or more different compounds on cells. In one aspect, the method comprises: providing a device of the present invention having three or more electrode arrays, each of which is associated with a fluid container of the device; attaching the device to an impedance analyzer; introducing cells into three or more fluid containers of the device that comprise an electrode array; adding at least one test compound to at least one of the three or more fluid containers comprising cells and adding at least one different test compound to at least one other of the three or more fluid containers comprising cells to provide at least two different test compound fluid containers; providing as a control fluid container at least one of the three or more fluid containers, in which the control fluid container receives cells but does not receive compound; attaching an impedance analyzer to the device; monitoring cell-substrate impedance of the two or more different test compound fluid containers that comprise different compounds and the one or more control fluid containers at at least three time points after adding the one or more test compounds; and analyzing impedance measurements from the two or more different test compound fluid containers and from the one or more control fluid containers at at least three time points after adding the one or more test compounds, in which changes in impedance can provide information about cell responses to the one or more test compounds.

In a related aspect, the present invention provides a method for performing a cell-based assay investigating the effect of two or more test compounds on cells using a cell-substrate impedance monitoring system. The method includes: a) providing a cell-substrate impedance monitoring system of the present invention; b) introducing cells into at least two wells of the device that each comprise an electrode array; c) adding to at least one well of the device comprising cells and an electrode array a first test compound; d) adding to at least one other well of the device comprising cells and an electrode array a second test compound; and e) monitoring cell-substrate impedance of at least one well comprising cells and a first compound and at least one well comprising cells and a second compound, in which changes in impedance can provide information about cell responses to the first and second compounds.

Preferably, time-dependent responses of cells to the first compound and the second compound are compared to see how similar or different the responses from the two compounds are. In one preferred embodiment of this method, time-dependent cytotoxic responses are compared.

The cells and test compound that can be used in the assay can be any as described above for assays testing effects of test compounds.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

Preferably, data from impedance monitoring of wells that comprise different test compounds are compared.

In one embodiment, for at least two different compound wells, impedance at three or more assay time points can be plotted versus time. Preferably, for a control well that does not receive compound, impedance at the same three or more assay time points is also plotted versus time. The impedance curves of different compound wells can be compared with the control impedance curve to determine whether the compounds have a similar or different effect on cells.

Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration the response of cells to different compounds are similar or different. Preferably, impedance curves or cell index curves generated from one or more control wells comprising cells in the absence of compound are compared with the test compound curves to assess the compound-specific effects of each compound. The effects of the compounds on cells can be for example, effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect on cells of one or more of the compounds used in the assay may be known. The mechanism of action of one or more compounds used in the assay may be known. In such cases, comparison of the responses of cells to other test compounds used in the assay with cellular responses to the one or more compounds whose effects are characterized can give information as to the similarity or difference in response of different compounds to a known compound.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

A plurality of compounds can be assayed with multiple cell types. In one preferred embodiment of this method, time-dependent cytotoxic responses of different cell types to a set of compounds are compared.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

A variety of assays can be employed, where the effect of two or more test compound on the behavior cells is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In one preferred embodiment of this method, time-dependent cytotoxic responses of cells to a set of compounds are compared. "Cytotoxicity profiling" in which the impedance responses of cells in response to a plurality of potentially cytotoxic compounds are compared, can provide information on the efficacy and mechanism of a test compound. Cytotoxicity profiling can be performed by comparing any combination of impedance plots, kinetic parameters derived from impedance plots, CI plots, CCI values, and CCI plots.

In one embodiment of the method, analyzing the cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Evaluating the Effect of Different Concentrations of a Compound on Cells

The present invention also includes methods of performing assays to test the effect of different concentrations of one or more test compounds on cells.

In one aspect, a method for testing different concentrations of a test compound on cells comprises: providing a device of the present invention having three or more electrode arrays, each of which is associated with a fluid container of the device; attaching the device to an impedance analyzer; introducing cells into at least two of the three or more fluid containers of the device that comprise an electrode array; adding different concentrations of a test compound to the two or more fluid containers of the device that comprise cells; providing a control fluid container that comprises cells but does not receive compound; monitoring cell-substrate impedance of the two or more different test compound fluid containers that comprise different concentrations of a test compound and of the one or more control fluid containers at at least three time points after adding a test compound; and analyzing impedance measurements from the two or more different test compound fluid containers and one or more control fluid containers at at least three time points after adding a test compound, in which changes in impedance can provide information about cell responses to the test compounds.

In a related aspect, the present invention provides a method for performing a cell-based assay investigating the effect of two or more concentrations of a test compound on cells using a cell-substrate impedance monitoring system. The method includes: providing a cell-substrate impedance monitoring system of the present invention; introducing cells into at least two of the three or more wells of the device that comprise an electrode array; adding different concentrations of a test compound to the two or more wells of the device that comprise cells; providing a control well that comprises cells but does not receive test compound; monitoring cell-substrate impedance of the two or more different test compound wells that comprise different concentrations of a test compound and the one or more control wells at at least three time points after adding a test compound; and analyzing impedance measurements from the two or more different test compound wells and the one or more control wells at at least three time points after adding a test compound, in which changes in impedance can provide information about cell responses to the test compounds.

The cells and test compound that can be used in the assay can be any as described above for assays testing effects of test compounds.

Impedance monitoring can be as described above for assays testing effects of test compounds. Preferably impedance is monitored from the at least two different test compound wells and at least one control well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurements taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In one embodiment, for at least two different compound concentrations, impedance or, preferably, cell index (including normalized cell index or delta cell index), at three or more assay time points is be plotted versus time. Preferably, for a control well that does not receive compound, impedance at the same three or more assay time points is also plotted versus time. An impedance curve or cell index curve can give an indication of the time frame at which a compound affects cell response. In some preferred embodiments, the cell index can be used as an indicator of cytotoxicity.

FIGS. 9A and B shows the responses of various cell types (listed in Table 1) to doxorubicin treatment as monitored using a cell-substrate imepdnace monitoring system of the presnet invention. The indicated cell lines were seeded onto microtiter devices fabricated with electronic sensor arrays shown in FIG. 1. The cellular responses were continuously monitored at 15 or 30 or 60 minutes time interval before and after treatment with doxorubicin. Comparison among these cell index curves showed that certain similarity does exist. Take the treatment of doxoorubincin at 3.13 uM as an example. For most of cell types tested, initially after the treatment, cell index increased with time in similar way to the cell index from DMSO control wells. After 10-20 hrs, depending on cell type, the cell index reached a peak and started decreasing with time. From that time on, the cell index monotonically decreases. Such cell index curves—characterized by "going up first and then going down"-were also observed for the cells treated with 5-Fluorouracil. Both Doxorubicin and 5-Fluorouacil act on cells through effects on DNA replication or topology.

Furthermore, such cell index curves are strikingly different from the cell index curves shown in FIGS. 10A and 10B, where 100 uM of olomoucine resulted in a nearly constant cell index value for 10, 20 even 30 hrs after compound addition. The cell index curves shown in FIG. 9 are also strikingly different from the cell index curves in FIG. 11, where nM concentration of paclitaxel caused an intial cell index decrease for about 15 hrs (it varies between cell types) and then a cell index increase. These dynamic changes in cell index curves reflect the fact that these different compounds interacts with the cells differently. Compounds that interact with cells in similar way or following same mechanism would result in a similar cell index response curves. One application of this is to investigate the mechanism of compound action based on the observed cell index curves. If cell index responses follow a certain pattern, then one may be able to deduce the mechanism of compound action. Alternatively, if two compounds showed similar, dynamic cell index response curves, then these two compounds may act on the cells with similar or same mechanism of compound action.

Figure 11A:
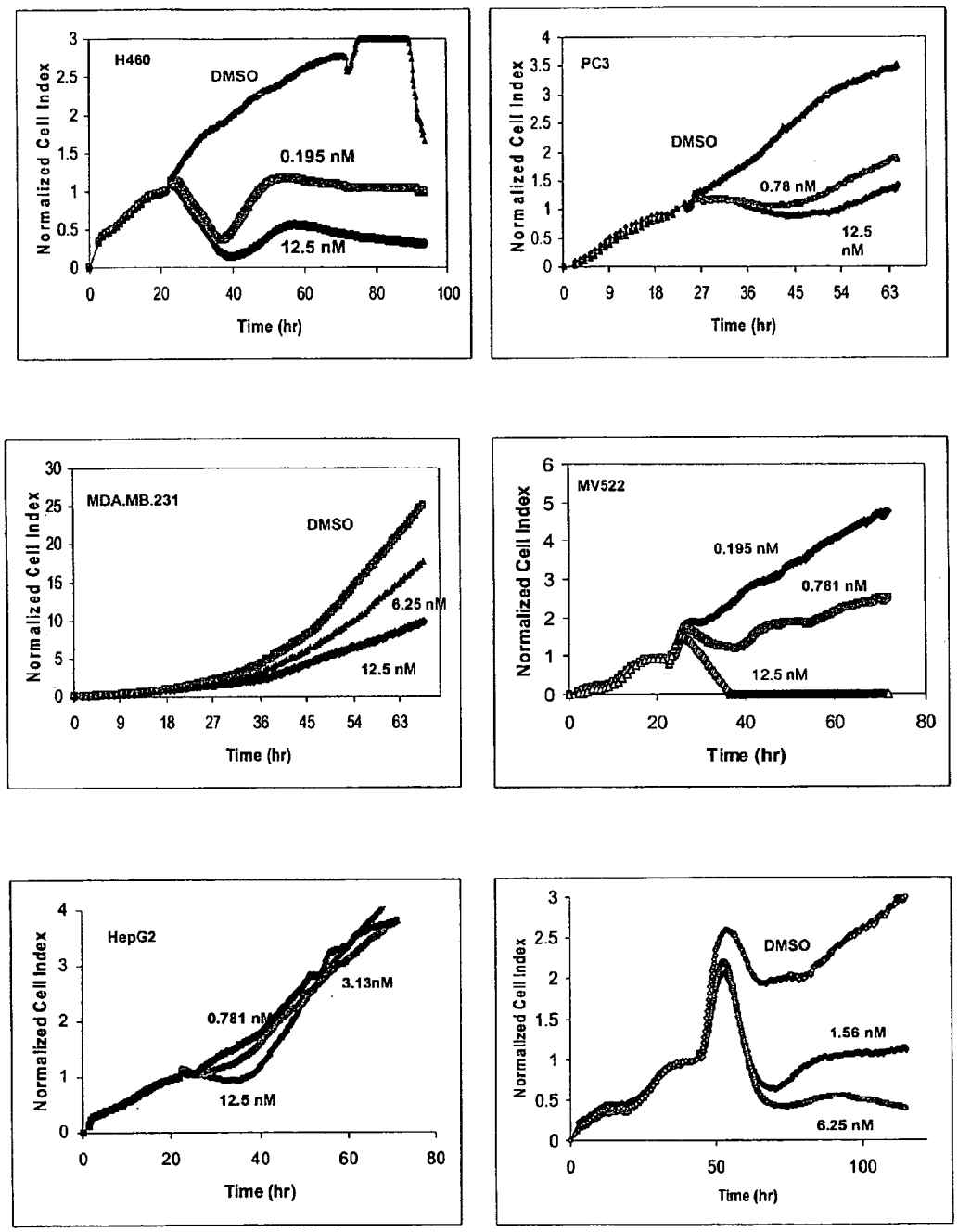
FIGS. 11A and 11B show the responses of various cell types (listed in Table 1) to paclitaxel treatment as monitored using a cell-substrate imepdnace monitoring system of the presnet invention. The indicated cell lines were seeded onto microtiter devices fabricated with electronic sensor arrays shown in FIG. 1B. The cellular responses were continuously monitored at 15 or 30 or 60 minutes time interval before and after treatment with paclitaxel.
Figure 11B:
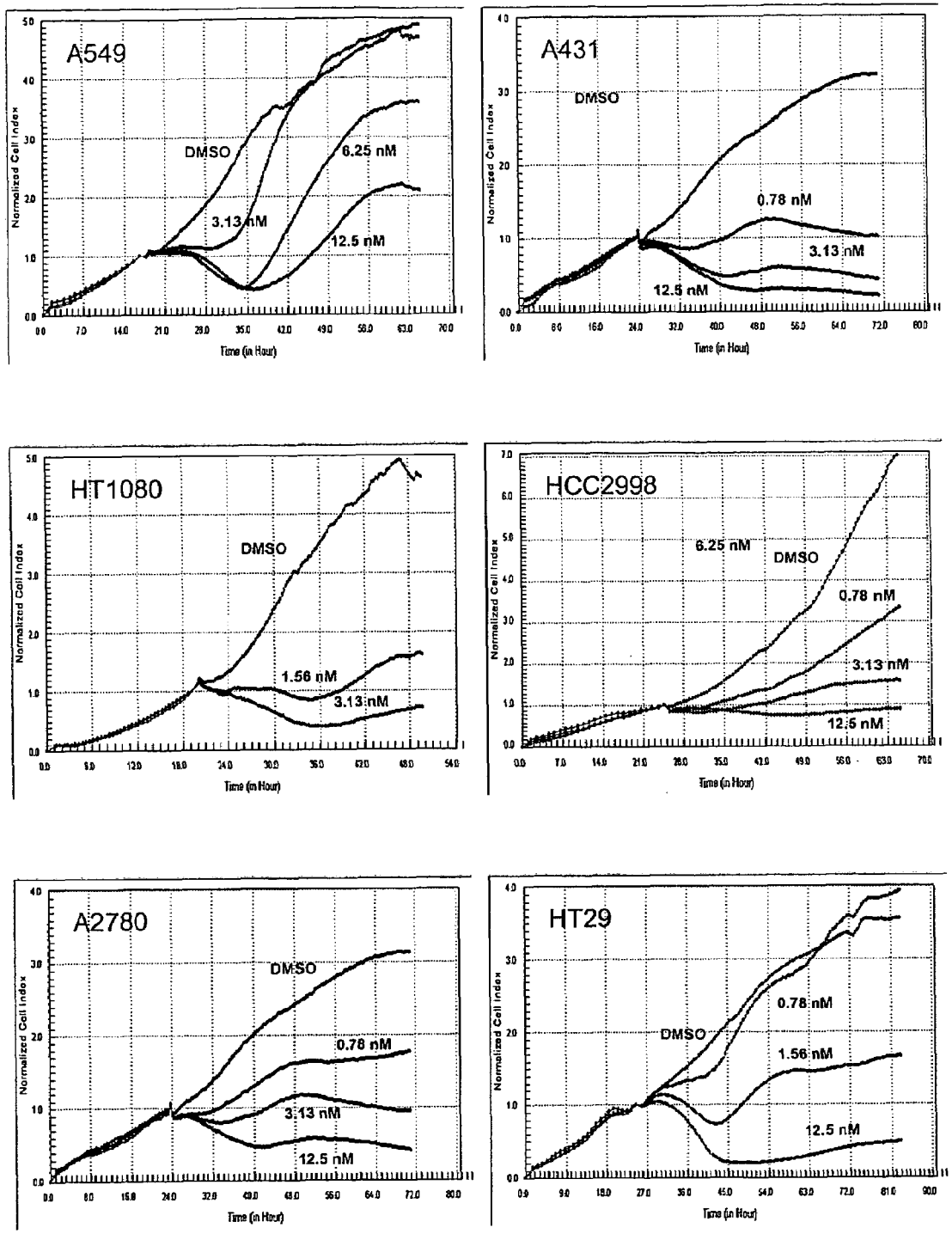
Figure 16A:
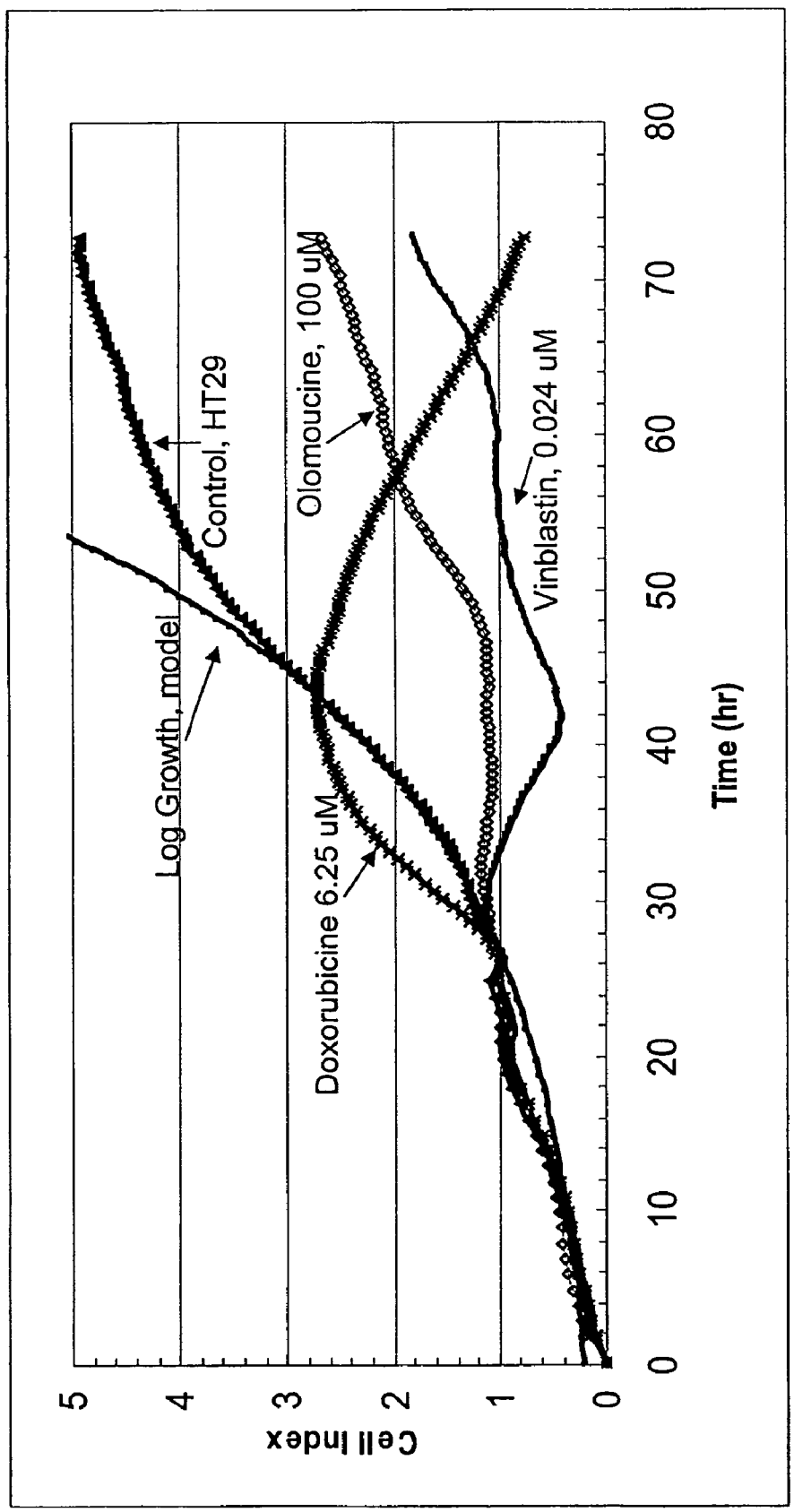
FIG. 16A shows the cell index curves of HT29 cells before and after treatment with various compounds. Also shown is an theoretical exponential increase of cell index with time (labeled as "Log-growth, model") and cells treated with DMSO vehicle control (labeled as "Control, HT29").
Figure 22:
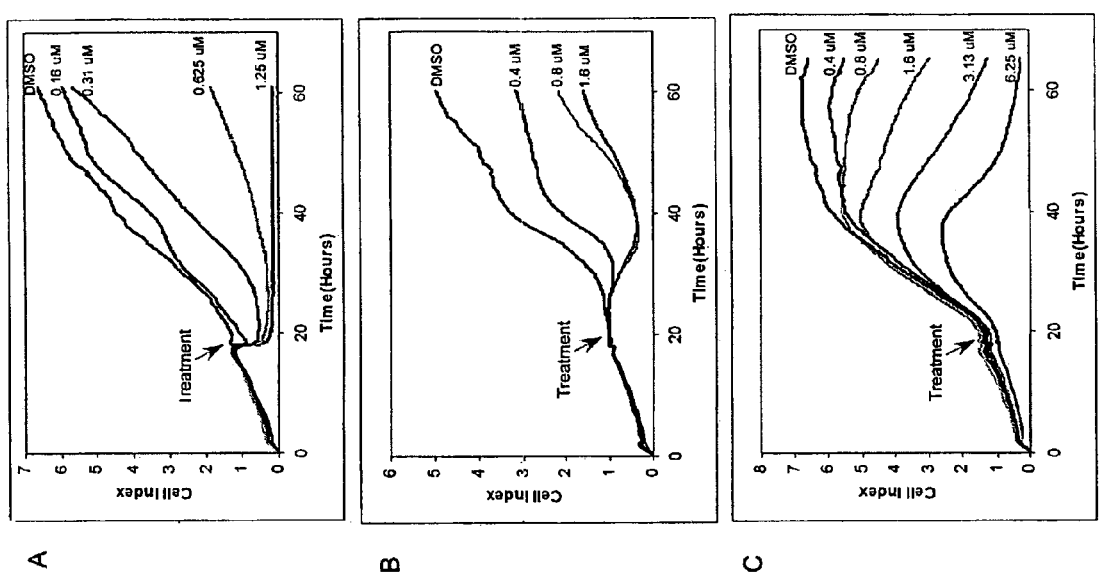
FIG. 22. Dynamic monitoring of cytotoxic compounds with target cells using a cell-substrate imepdnace monitoring system of the presnet invention. A549 cells were seeded in a device of the present inventoon and continuously monitored using the RT-CES system. The cells were treated with the indicated final concentrations of (A) staurosporine, (B) vinblastine and (C) 5-flourouracil.

FIGS. 11A and 11B shows the responses of various cell types (listed in Table 1) to paclitaxel treatment as monitored using a cell-substrate imepdnace monitoring system of the presnet invention. The indicated cell lines were seeded onto microtiter devices fabricated with electronic sensor arrays shown in FIG. 1. The cellular responses were continuously monitored at 15 or 30 or 60 minutes time interval before and after treatment with paclitaxel. Comparison among these cell index curves showed that certain similarity does exist. Take the treatment of palitaxel at 0.78-12.5 nM range as examples. Typically, such nM paclitaxel treatment resulted in an initial decrease in cell index for about 15-20 hrs. For one particular cell index curve, after the cell index reached a minimum, it then reversed its decreasing trend and started to increase. Such "going down and then going up" feature in cell index curves was also observed in cell index curves for cells treated with vinblastin or colcemid. Examples of cell index curve for vinblastin-treated cells are shown in FIG. 16A and FIG. 22. All these compounds—i.e., paclitaxel, vinblastin and colcemid, are so called mitotic poisons and follow similar mechanism of drug action. For example, both vinblastin and paclitaxel act on microtubule dynamics within a cell.

In addition, for a given assay time point, cell index (including normalized cell index or delta cell index), can be plotted versus compound concentration. Such dose response relationships can be used to derive a time-dependent IC5, IC10, IC20, IC30, IC40, IC50, IC60, IC70, IC80, IC90, or IC95. In some preferred embodiments, a time-dependent IC50 is calculated for a compound. Determining a range of time-dependent IC50s for a compound provides information on when the effect of the compound on cells is maximal.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

Preferably, data from impedance monitoring of wells that comprise different cell types are compared. In one preferred embodiment impedance monitoring is performed for different cell types exposed to multiple dose concentrations of a compound. In some embodiments, multiple compounds can be tested with multiple cell types. In some embodiments, multiple compounds at multiple concentrations can be tested with multiple cell types.

Cytotoxicity Profiling

In another aspect, the present invention provides a method for performing real-time cytotoxicity assay of a compound, comprising: a) providing an above described system; b) seeding cells to the wells of multiple-well devices; c) adding the compound to the wells containing cells; d) monitoring cell-substrate impedance before and after adding the compound at a regular or irregular time interval; wherein the time dependent impedance change provides information about time dependent cytotoxicity of the compound. In one embodiment, the cell-substrate impedance is monitored at regular time intervals. In exemplary embodiments, the impedance is measured at a regular 2 hour, 1 hour, 30 min or 15 min time interval before and after adding the compound.

In one embodiment of the above method, multiple wells with same cell types are used, wherein each well is added with the compound of different concentrations. The method provides the time-dependent and concentration-dependent cytotoxic responses.

In yet another aspect, the present invention provides a method for analyzing and comparing time-dependent cytotoxic effects of a first compound and a second compound on a cell type, comprising: a) performing a real-time cytotoxicity assay on a cell type with the first compound using the method described above; b) performing a real-time cytotoxicity assay on said cell type with the second compound using the method described above; c) comparing the time-dependent cytotoxic responses of the first compound and the second compound to see how similar or different the responses from the two compounds are. In one embodiment of this method, time-dependent cytotoxic responses are determined for the first compound at multiple dose concentrations. In another embodiment, time-dependent cytotoxic responses are determined for the second compound at multiple dose concentrations. In yet another embodiment, time-dependent cytotoxic responses are determined for both first compound and second compound at multiple dose concentrations.

In another embodiment of above methods, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In one embodiment of the method described above, time dependent IC50 may be derived for the compounds and comparison between their cytotoxic responses is done by comparing their time dependent IC50 curves based on cell index values. If the IC50 curves follow a similar time-dependent trend, the two compounds may follow a similar mechanism for inducing cytotoxicty effects. In another embodiment of the method described, direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

In one embodiment of the method, analyzing real-time cytotoxicity response may include the derivation of time-dependent IC50 values for the compound on the multiple cell types. In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

In yet another embodiment, the above methods are applied to perform cytotoxicity profiling of multiple compounds on multiple cell types.

In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Some examples of compound assays that can be performed using a cell-substrate impedance system of the present invention are provided by way of illustration with reference to the figures. In these examples, cell index is calculated using the same method as the Cell Index calculation method (A) as described in Section C of the present application. In some of the figures of the present application, Normalized Cell Index was plotted. The Normalized Cell Index at a given time point is calculated by dividing the Cell Index at the time point by the Cell Index at a reference time point. Thus, the Normalized Cell Index is 1 at the reference time point.

As described in the present application, if the cell attachment conditions remain unchanged or exhibit little change over the course of an assay that uses impedance monitoring, then the larger the cell index, the larger the number of the cells in the wells. A decrease in cell index suggests that some cells are detaching from the substrate surface or dying under the influence of the compound. An increase in cell index suggests that more cells are attaching to the substrate surfaces, indicating an increase in overall cell number.

Figure 5:
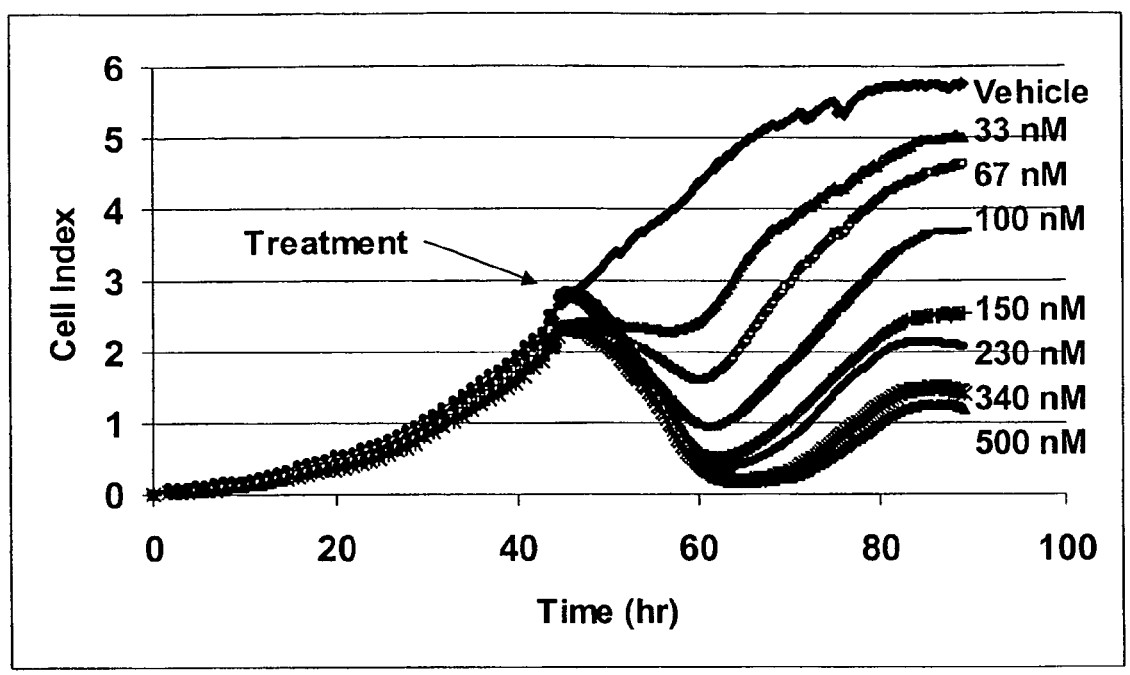
FIG. 5 shows time-dependent cell index for H460 cells treated by anticancer drug paclitaxel. Different wells of cultured H460 cells were treated at their exponential growth phase with different concentrations of Paclitaxel. The dynamic response of the cells to different doses of paclitaxel was monitored in real time every 15 minutes for 50 hours after treatment using a cell-substrate impedance monitoring system of the presnet invention. For paclitaxel concentration between 67 nM and 500 nM, H460 cells exhibited a gradual decrease in cell index initially after the compound addition. However, the cell index reached a minimum at a time dependent on the compound concentration between about 15 hours and 20 hours after compound addition. After that point, the cell index exhibited a gradual increase in cell index. The cell index for compound concentration of 33 nM exhibited a near-constant value for time up to about 15 hours after compound addition. After 15 hours following the compound addition, the cell index exhibited a gradual increase in cell index.

FIG. 5 shows curves that represent the time-dependent cell index for H460 cells treated with different concentrations of the anticancer drug paclitaxel. In this experiment, H460 cells were introduced into wells of a 16× cell-substrate impedance monitoring device (16× E-Plate). The device was positioned on a device station that was located in an incubator maintaining conditions of 37 degrees C. and 5% $CO_2$. The cells were cultured and treated at their exponential growth phase with different concentrations of paclitaxel. The dynamic response of the cells to different doses of paclitaxel was monitored by monitoring cell-substrate impedance in real time every 15 minutes for 50 hours after treatment using a cell-substrate impedance monitoring system. The cell-substrate impedance monitoring system calculated the cell index at each time point monitored and plotted the cell index as a function of time. For paclitaxel concentrations between 67 nanomolar and 500 nanomolar, H460 cells exhibited a gradual decrease in cell index after compound addition. However, the cell index reached a minimum at a time dependent on the compound concentration, between about 15 hours and 20 hours after compound addition. After that point, there was a gradual increase in cell index in these wells. The cell index for compound concentration of 33 nanomolar exhibited a near-constant value for up to about 15 hours after compound addition. After 15 hours following compound addition, the cell index exhibited a gradual increase.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

Figure 6:
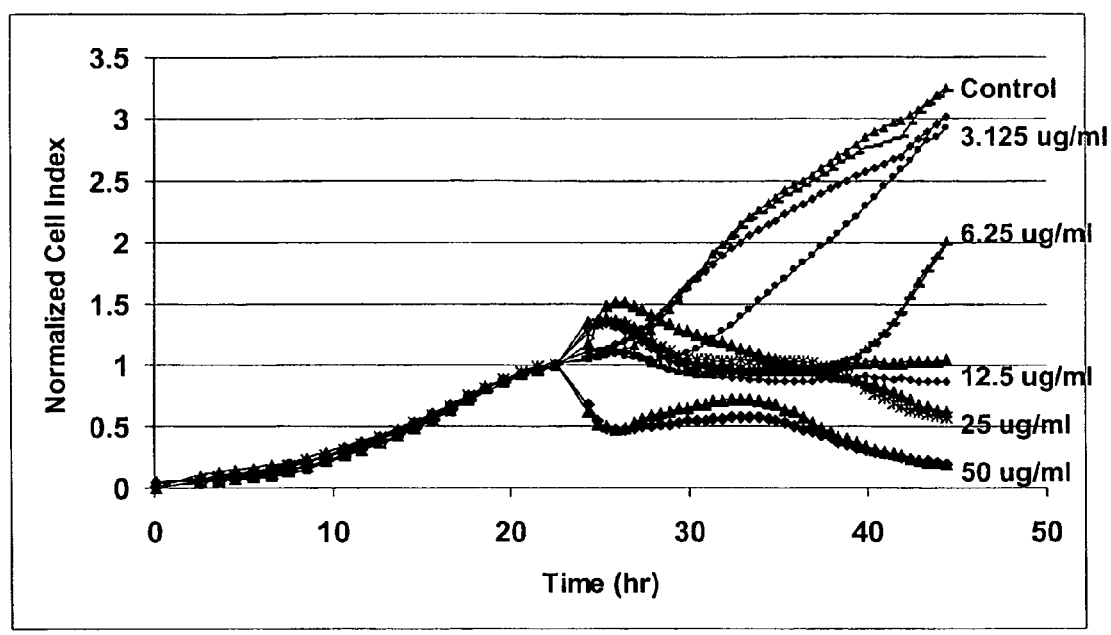
FIG. 6 shows time-dependent cell index for H460 cells treated by anticancer drug AC101103. Different wells of cultured H460 cells were treated at their exponential growth phase with different concentrations of AC101103. The dynamic response of the cells to different doses of AC101103 was monitored in real time every 30 minutes for about 20 hours on a cell substrate impedance monitoring system of the presnet invention. The time-dependent cell index in FIG. 6 is significantly different from those shown in FIG. 5. For compound concentrations at 3.125 ug/ml, 6.25 ug/ml and 12.5 ug/ml, the cell index exhibited a near-constant value for about 5 hrs, about 15 hrs and >20 hrs respectively. For compound concentrations at 3.125 ug/ml and 6.25 ug/ml, the cell index started to increase after about 5 hrs and about 15 hrs following compound addition. For the compound concentration of 25 ug/ml, there was a gradual, yet slow decrease in the cell index after compound addition. For the compound concentration of 50 ug/ml, there was an about 10 hr time period over which the cell index remained near-constant, and after that, the cell index decreased steadily.

FIG. 6 shows curves that represent the time-dependent cell index for H460 cells treated with anticancer drug AC101103. H460 cells were introduced into wells of a 16× cell-substrate impedance monitoring device (16× E-Plate). The device was positioned on a device station that was located in an incubator maintaining conditions of 37 degrees C. and 5% $CO_2$. The cells were cultured and treated at their exponential growth phase with different concentrations of AC101103. The dynamic response of the cells to different doses of AC101103 was monitored by measuring impedance in real time every 30 minutes for about 20 hours after treatment on the cell-substrate monitoring system.

Notably, the time-dependent cell index in FIG. 6 is significantly different from those shown in FIG. 5. For compound concentrations at 3.125 microgram/ml, 6.25 microgram/ml and 12.5 microgram/ml, the cell index exhibited a near-constant value for about 5 hrs, about 15 hrs and >20 hrs respectively. For compound concentrations at 3.125 microgram/ml and 6.25 microgram/ml, the cell index started to increase after about 5 hrs and about 15 hrs following compound addition. For the compound concentration of 25 microgram/ml, there was a gradual, yet slow decrease in the cell index after compound addition. For the compound concentration of 50 microgram/ml, there was an about 10 hr time period over which the cell index remained near-constant, and after that, the cell index decreased steadily.

Figure 7:
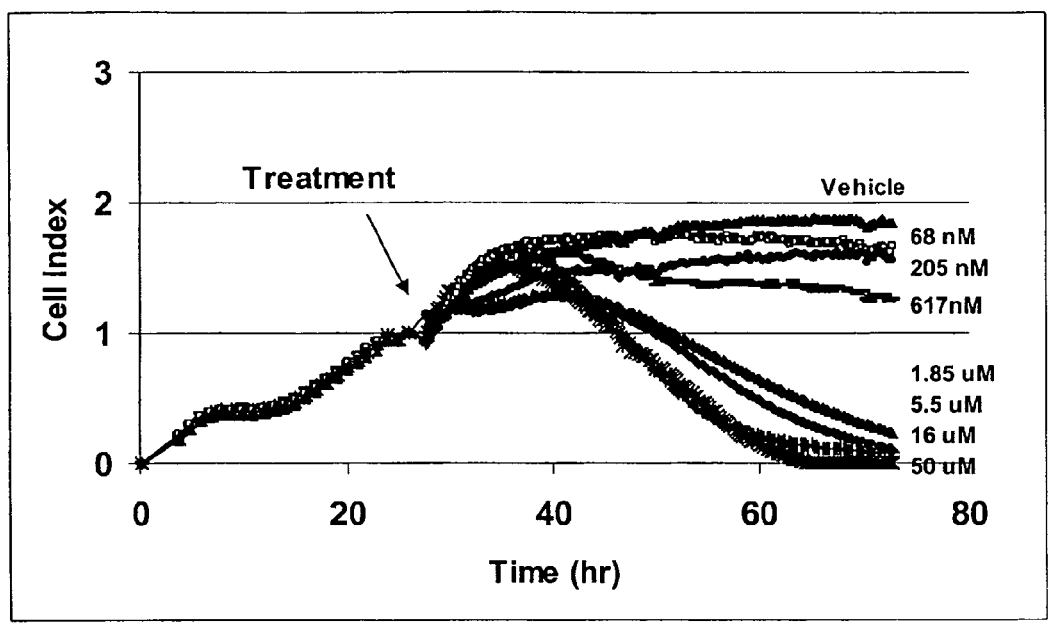
FIG. 7 shows dynamic drug response curves of A549 cells treated with doxorubicin. 10,000 A549 cells were seeded in each well of a 16× device. The cell attachment and cell growth were monitored on the cell-substrate impedance monitoring system of the present invention in real time before treatment. When the cells were in exponential growth phase, doxorubicin at different concentration was added to the cells. Same volume of a solvent used for dissolve the drug was served as vehicle control. The time, and drug dose dependent cell response to doxorubicin was recorded in real time.

FIG. 7 shows dynamic drug response curves of A549 cells treated with doxorubicin. 10,000 A549 cells were seeded into each well of a 16× device (16× E-Plate). The device was positioned on a device station that was located in an incubator maintaining conditions of 37 degrees C. and 5% $CO_2$. Cell attachment and cell growth were monitored on a cell-substrate impedance system in real time before treatment by monitoring impedance at regular intervals. When the cells were in exponential growth phase, doxorubicin at different concentrations was added to the wells. The same volume of the solvent used to dissolve the drug was added to some wells as a control. The time, and drug dose dependent cell response (calculated as cell index) to doxorubicin was recorded in real time on the cell-substrate impedance monitoring system as shown in this figure.

D.4. Real-time Cell Based Assays to Assess or Quantify Target Cell Killing by Effector Cells To address some of the limitations with current assay methods for measuring NK-mediated (or effector-cell mediated) target cell killing, the present invention discloses a lable-free and kinetic-based method for meausimg NK-mediated (or effector cell-medaited) cytotoxicty. The method is based on non-invasive measurement of the viability of target cells that have been seeded on microtiter plates (E-plates) that have incorporated microelectrode arrays at the bottom of the wells. The interaction of adherent target cells with the microelectrodes results in displacement of the ionic environment between the cell sensor electrode and the media in a precise and specific way which is dependent on the number of target cells seeded, the morphology of the cells and the quality of cell adhesion (Abassi et al., 2004; Solly et al., 2004; Xing et al., 2005). The status of the target cells can be continuously monitored by measuring the impedance of microelectrode arrays in the wells. Effector-mediated cytotoxicity results in target cell death which is accompanied by morphological changes such as a loss of the integrity of the actin cytoskeleton and cell rounding that is ultimately accompanied by de-adhesion of the cells (or loss of cell-substarte contact). All these morphological events leads to a reduction of cell-substrate impedances over time. Furthermore, since the effector cells are suspended cells they only interact with the target cells through specific receptors on the cell surface and not with the sensor electrodes in the well. Therefore, the addition of effcetor cells to the target cells has very minimal effect on the cell-substrate impedance. Thus, cell-substrate impedance measured over time with the target cells and effector cells in the well provides the information as for the status of target cells.

NK cells have been shown to recognize and eradicate tumor cells (target cells) by a variety of mechanisms including direct killing by perforin or granzymes, inducing apoptosis through the death receptors and by antibody-dependent cellular cytotoxicity. In the present invention, we utilize and quantify loss of cell-substrate (electrode) contact due to cytotoxicity or apoptosis by measuring cell-substrate impedance as a means to assess effector cell mediated killing of target cells using cell sensor technology.

The methods previously disclosed in U.S. Provisional Patent Application No. 60/598, filed on Aug. 4, 2004; U.S. 608, 60/630,071, filed on Nov. 22, 2004; U.S. Provisional Patent Application No. 60/689,422, filed on Jun. 10, 2005, and those provided herein may be utilized to measure or determine cytolytic activity of a variety of effector cells. More specifically, the present invention provides methods of measuring cytolytic activity including providing a device capable of monitoring cell-substrate impedance operably connected to an impedance analyzer, adding target cells to at least one well of the device, adding effector cells to the well, monitoring impedance of the well and optionally determining a cell index from the impedance, and determining viability of the target cells. In some embodiments viability of the target cells are determined by comparing the impedance or cell index between two time points. Non-limiting examples of suitable time points are before and after adding effector cells. Monitoring impedance and determining a cell index may be performed using methods disclosed in the present application.

As a non-limiting example, target cells or cell lines such as primary cells, tissue culture cell lines or tumor cell lines may be seeded in ACEA's microtiter plates (for example, 16× or 96× E-Plates, E-Plates are the microtiter plates that have incorporated microelectrode arrays at the bottom of the wells) at a predetermined density. Cell adhesion and proliferation may be monitored continuously using the real-time cell electronic sensing (RT-CES™) system. After an overnight incubation (16-24 hours), the appropriate effector cells may be added at a pre-determined ratio of effector cell to target cell to the wells containing the target cells. The cellular response of the target cells may be continuously monitored overtime using the RT-CES.

Target Cells

Target cell refers to any cell that can be lysed or killed by the effector cells. The present invention may be utilized to assess or quantify killing of a variety of target cells by effector cells. Thus, a variety of target cells may be utilized with the present invention. For example target cells may include but are not limited to cancer cells, cells isolated from cancerous tissue, primary cells purified or derived from human, mouse and other animal origin, endothelial cells, or any cells from a cell line derived from a living organism (for example: human, mouse, rat, other animals), or cell lines infected with bacteria or virus.

Target cells may be added to one or more wells or fluid containers of the devices capable of monitoring cell-substrate impedance, depending on the desired assay or experiment. Target cells may be added along with compounds, without compounds, with additional cells and the like. Target cells may be added to wells and incubated in the wells for some time period prior to addition of effector cells. Target cells may be utilized as controls in an assay including studying the effect of an effector cell on a target cell. In this embodiment a control well may include target cells without effector cells for a real-time comparison of impedance or cell index.

After target cells are added into wells, cell-substrate impedance may be monitored at at lest two time points. Optionally, measured cell-substrate impedance may be used to derive cell index at a time point. The measured impedance or optionally derived cell index may be used to determine quantity of target cells (i.e., viable target cells) in the well. In some embodiments, the measured impedance or optionally derived cell index may be used to determine viability of target cells.

In the assay for measuring cytolytic activity of effector cells, one is interested in how many target cells or what percentage of target cells have been killed by the effector cells. Thus, the quantity or viability of target cells may be determined at any point in during an assay. For example, the quantity target cells may be determined before adding effector cells or may be determined after adding effector cells. In some embodiments the quantity of target cells are determined both before and after adding effector cells. Target cells may be quantified using a variety of techniques such as but not limited to using a pre-derived formula that correlates cell number with cell index at a time point.

Effector Cells

One skilled in the art of immunology would recognize the present invention may utilize a variety of effector cells. Effector cells may be any cell capable of killing or lysing a target cell or a target cell marked with antibody. As non-limiting examples effector cells may be Natural Killer (NK) cells, Cytotoxic T-Lymphocytes (CTLs), neutrophils, easonophils, macrophages, Natural Killer T (NKT) cells, B-cells, T-cells, a cell type having cytolytic activity and the like. Effector cells may include primary cells or cell lines derived from humoan, mouse or other animal origin.

Effector cells may be added to one or more wells or fluid containers at a predetermined ratio to the target cells. One skilled in the field of biology would be able to provide or determine the appropriate ratio (or ratios) of effector cell target cell.

The present invention also provides for the addition of a compound or factor capable of activating, deactivating or stimulating effector cells. Such compounds may vary depending on the effector cell but may include lypo-polysaccharide (LPS), an antibody, an accessory compound, a compound obtained or screened from a library of compounds and the like. Thus the compound or factor may be any suitable compound or factor used in the biologocial arts for stimulation of an effector cell. As non-limiting examples the compound may be a monoclonal antibody, a polyclonal antibody, a peptide, a protein, a lipid, a biomolecule, a nucleic acid molecule, a naked DNA molecule and the like. A variety of antibodies may be obtained or provided for the present invention such as but not limited to IgG, IgM, IgE, IgA as well as heavy chain portions, light chain portions including kappa and lambda light chains, Fc portions, Fab portions, Fab'2 portions and the like. Antibodies may be humanized or may be cross-species.

Similarly additional cell types or cell lines may be provided with effector cells. Such cells include but are not limited to accessory cells.

Prior to and after addition of effector cells to the wells containing target cells, cell-substrate impedance is measured. Since the effector cells are suspended cells they only interact with the target cells through specific receptors on the cell surface and not with the sensor electrodes in the well. Therefore, the addition of effcetor cells to the target cells has very minimal effect on the cell-substrate impedance. Thus, cell-substrate impedance measured over time with the target cells and effector cells in the well provides the information as for the status of target cells.

Monitoring Impedance

Impedance may be monitored using the methods previously disclosed in the present application. Monitoring impedance may include performing one or more impedance measurements at one or more time points or a series of measurements at a series of time points. Monitoring impedance may include performing impedance measurements at multiple frequencies. Impedance measurement includes the measurement of resistance and/or reactance. A series of three or more impedance measurements at three or more time points may be performed to provide a time-dependent, impedance curve that may depict a maximum or minimum effect of a compound or effector cells on target cells, or may depict when a maximum effect of compound or effector cells on target cells is reached. Depending on the desired assay, impedance may be monitored or measured at regular or irregular time intervals during an assay period.

In some embodiments an impedance measurement is performed at a time point or time points before adding effector cells or immediately prior to adding effector cells and after adding effector cells. In one exemplary embodiment, impedance measurement may be performed at a time point of less than less than 30 minutes, less than 1 hour, less than 2 hours, less than 4 hours, or less than 10 hours, or less than 24 hours, or other time length prior to adding effector cells. In another exemplary embodiment, impedance measurement may be performed at a time point immediately preceding or prior to adding effector cells, such as less than 20 minutes, less than 10 minutes, less than 5 minutes, less than 2 minutes, or less than 1 minute prior to adding effector cells. In still another exemplary embodiment, impedance measurement may be performed at regular or irregular time intervals prior to addition of effector cells. As can be envisioned, a series of two, three, four or more measurements may be desired after adding effector cells. In one exemplary embodiment, impedance measurement may be performed at regular time intervals (for example, every hour, or every 15 minutes) after adding effector cells. In another exemplary embodiment, impedance measurement may be performed at irregular time intervals (for example, initially every 10 minutes up to 1 hour and followed by every 1 hour up to 24 hours) after adding effector cells. In still another exemplary embodiment, impedance measurement may be performed at a time point of more than 1 minute, more than 5 minute, more than 30 minutes, more than 1 hour, more than 2 hours, more than 5 hours, more than 10 hours after adding effector cells.

A method of the present invention is to screen for cytotoxic effect of effector cells (for example, NK cells, Cytotoxic T cells, neutiphils) on target cells using measurement of cell-substrate impedance. It is based on quantification of cytotoxicity that arise as a response to interaction of effector cells with their target cells. Because the impedance readout replies on the interaction of target cells with the sensor electrodes, the cell killing or cytolysis that is mediated by the effector cells, leads to morphological changes or total loss of adherence of the target cells to the surface of the electrodes in the well. Consequently, morphology changes or more prominently the loss of adhesion due to cytotoxiicty leads to a time-dependent decrease in the cell-substrate impedance which correlates with target cell killing. The more the target cells are killed due to effcetor-cell mediated cytotoxicity (i.e., the lower the viability of target cells is), the larger the decrease in the cell-substrate impedance is.

Cell Index

The methods of the present invention may include comparing one or more impedance measurements or comparing one or more cell indexes or cell index values. In one embodiment, a cell index is determined by calculating, for each measurement frequency, the relative-change in resistance (a component of impedance) of a well when target cells are present in the well with respect to that of the well when no cell is present, and then finding the maximum relative-change in resistance for all frequencies measured. The maximum relative-change in resistance is used as cell index (see equation (4) in Section C. Methods for Calculating Cell Index (CI) and Cell Change Index (CCI) of the present invention). If impedance is measured at a single frequency, then the relative change in resistance (a component of impedance) of a well when target cells are present in the well with respect to that of the well when no cell is present. Other methods for calculating cell index have been disclosed in a previous Section C. Methods for Calculating Cell Index (CI) and Cell Change Index (CCI) of the present invention).

The cell index may be a normalized cell index. Methods of normalizing a cell index have been previously disclosed in the present application and may be utilized when measuring cytolytic activity. In some embodiments normalization is determined at a time point immediately preceding a point in which effector cells are added to a well or fluid container. In some embodiments, the time point immediately preceding a point in which effector cells are added to a well refers a time point of less than 2 hours, less than 1 hour, less than 40 minutes, less than 20 minutes, less than 10 minutes, less than 5 minutes, less than 2 minutes, or less than 1 minute prior to adding effector cells.

Determining Viability of a Target Cell and Cytolytic Activity of Effector Cells

In the present invention, cell-substrate impedance is measured as an indicator for the status (e.g quantity, viability) of target cells prior to and/or after addition of effector cells. The impedance and optionally the cell index may be used to determine the viability of the target cells and therefore the cytolytic activity of the effector cells. For example, an impedance or cell index that decreases after the addition of effector cells may suggest decreased viability or increased cytolytic activity by the effector cells.

In one exemplary embodiment, the viability of target cells at a time point after adding effector cells in a well may be determined by comparing impedance of the well at the time point of interest to impedance of the well at a time point before adding effector cells. For example, the viability of target cells may be calculated using the formula, Viability=Resistance$_{at\ a\ time\ point\ after\ adding\ effector\ cells}$/Resistance$_{at\ a\ time\ point\ prior\ to\ effector\ cells}$, where resistance is a component of impedance of the well measured at a chosen frequency. Non-limiting example of the frequency includes ~1 kHz, ~5 kHz, ~10 kHz, ~20 kHz, ~50 KHz, less than 1 kHz, between 1 and 10 kHz, between 10 and 100 kHz, or above 100 kHz. For above formula to be valid, there are several implicit assumptions. First, the resistance of the well at the chosen frequency is assumed to follow linear or approximately linear relationship with the number of viable cells in the well. Secondly, in the time period between two time points of prior to and after adding effector cells, there is little or none cell proliferation of target cells. Thus, the viability of target cells at a time point after adding effector cells may be defined as the percentage for viable target cells at the time of interest out of total initial viable target cells at a time point prior to (or, for example, immediately preceding) adding effector cells.

In another approach, viability of target cells at a time point after addition of effector cells may be determined by comparing the cell index of the well prior to and after addition of effector cells. Viability of target cells may be calculated as the ratio of the cell index of the well at the time point of interest to the cell index of the well immediately prior to addition of effector cells. Such a calculation has an implicit assumption that the cell index of a well may be approximately proportional to the number of the viable cells in the well.

In still another approach, viability of target cells in a test well at a time point after addition of effector cells may be determined by comparing the impedance (or cell index) of the well at the time point of interest to the impedance (or cell index) of a control well to which same number of target cells and no effector cells are added. Viability of target cells at a time point after adding effector cells may be calculated as the ratio of the impedance (or cell index) of the test well at the time point of interest to the impedance (or cell index) of the control well at the same time point. Such a calculation of viability of target cells in a test well has an implicit assumption that if there is no killing or lysis of target cells by effector cells, the impedance or cell index of the test well would be the same as that of the control well. For such calculation of viability of target cells, cell index may be normalized cell index.

In an antibody dependent cellular cytotoxicity assay, target cells are added to both a test well and a control well. A specific antibody that interacts with the specific target on the target cells is added to the test well, and a non-specific antibody is added to the control well. Effector cells are added to both control well and test wells. Viability of target cells in the test well at a time point after adding effector cells may be determined by comparing the impedance (or cell index) of the well at the time point of interest to the impedance (or cell index) of the control well. Viability of target cells at a time point after adding effector cells may be calculated as the ratio of the impedance (or cell index) of the test well at the time point of interest to the impedance (or cell index) of the control well at the same time point. Such a calculation of viability of target cells in the test well has an implicit assumption that if there is no killing or lysis of target cells by effector cells, the impedance or cell index of the test well would be the same as that of the control well. For such calculation of viability of target cells, cell index may be normalized cell index.

The above approach for determining viability of target cells in a test well by comparing impedance or optionally cell index of the test well to the impedance or optionally cell index of the control well may also be applied to complement mediated cellular cytotoxicity assay and to complement-dependent, effector cell-medaited cytotoxicity assay.

Cytolytic activity of effector cells refers to the ability of effector cells to lyse or kill target cells. For a given ratio of effector cell number to target cell number and for a specific time period after addition of effector cells to target cells, if effector cells of a first type kills more target cells than effector cells of a second type, then the effector cells of the first type have higher cytolytic activity. There are various parameters that can be determined and be used to indicate or quantify cytolytic activity of effector cells. For example, viability of target cells at a time point after effector cells are added to target cells in a well can be used to indicate the cytolytic activity of the effector cells. A low viability of target cells indicates that many target cells have been killed by the effector cells and shows that the effector cells have high cytolytic activity. In another example, percent cytolysis (or percentage of cytolysis) of target cells at a time point after effector cells are added to target cells can also be used to indicate the cytolytic activity. A low percent cytolysis indicates that few target cells have been killed by the effector cells and show that the effector cells have low cytolytic activity. In one exemplary embodiment of the present invention, the cytolytic activity of the effector cells are expressed as percent cytolysis or percentage of cytolysis, which may be derived at any given time point after adding effector cells to a test well by the formula of {percent cytolysis=(1−cell index of test well/cell index of control well)}, where same number of target cells have been added to both control well and test well. In an assay screening for cytotoxic effects of effector cells, effector cells are added to only test well and no effector cells are added to control well (for control well, a same volume of culture media used suspending effector cells is added at the same time when effector cells are added to test well). In an antibody dependent cellular cytotoxicity (ADCC) assay, a specific antibody that interacts with the specific target on the target cells is added to test well, and a non-specific antibody is added to control well. Effector cells are added to both control well and test wells. An implicit assumption for this formula is that cell index follows approximately linear relationship with the number of viable target cells in the well. Thus, if no target cell is killed or lysed by effector cells, cell index of test well will be the same as cell index of control and percent cytolysis is zero. Effector cells have no cytolytic activity. If all target cells are killed or lysed by effected cells, cell index of test well will be zero or approximately zero, then percent cytolysis is 1 or 100%. The effector cells have a 100% cytolytic activity. In general, the more the target cells are killed or lysed, the smaller the cell index of test well, and the larger the percent cytolysis. Furthermore, in some embodiments, cell index in the above equation to calculate percent cytolysis is normalized cell index.

Screening for Cytotoxic Effects of Effector Cells

In one aspect, the present invention is directed at a method to screen for effector cell (for example, NK, Cytotoxic T Lymphocytes—CTL, or neutrophil)-mediated killing of target cells using electronic cell sensing technology. One approach for electronic measurement of cells is based on the measurement of cell-substrate or cell-electrode impedances. The approach features in the integration of cell biology with microelectronics and is based on the electronic detection of biological assay process. The details of this cell electronic sensing technology, called real-time cell electronic sensing (RT-CES), and associated devices, systems and methods of use have been provided in, PCT application number PCT/US03/22557, titled "Impedance based devices and methods for use in assays", filed on Jul. 18, 2003; U.S. patent application Ser. No. 10/705,447, titled "Impedance based devices and methods for use in assays", filed on Nov. 10, 2003; PCT Application No. PCT/US04/037696, entitled "Real time electronic cell sensing system and application for cell based assays", filed on Nov. 12, 2004; U.S. patent application Ser. No. 10/987,732, entitled "Real time electronic cell sensing system and application for cell based assays" filed Nov. 12, 2004; PCT Application No. PCT/US05/004481, entitled "Real time electronic cell sensing system and applications for cytotoxicity profiling and compound assays", filed on Feb. 9, 2005; U.S. patent application Ser. No. 11/055,639, entitled "Real time electronic cell sensing system and applications for cytotoxicity profiling and compound assays" filed Feb. 9, 2005. All the above applications are incorporated by reference.

For measurement of cell-substrate or cell-electrode impedance, microelectrodes having appropriate geometries are fabricated onto the bottom surfaces of microtiter plate or similar device, facing into the wells. Cells are introduced into the wells of the devices (E-Plates), and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells, electronic impedance between or among electrodes at a single frequency or multiple frequencies can be measured automatically and in real time. Based on measured electrode impedance values, a cell index may be derived and provided. The cell index obtained for a given well reflects: 1) how many cells are attached to the electrode surfaces in this well, 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In one aspect, the method of the present invention is to screen for cytotoxic effect of effector cells (such as NK cells, CTL or neutrophil) on target cells using measurement of cell-substrate impendence. The method is based on quantification in real time of cytotoxicity that arise as a response to interaction of effector cells such as NK cells, CTL or neutrophils with their target cells. Because the electronic impedance between or among electrodes relies on the interaction of target cells with the electrodes, the cell killing that is mediated by the effector cells, leads to morphological changes or total loss of adherence of the target cells to the surface of the electrodes, or eventual lysis of the target cells in the well. Consequently, morphology changes or more prominently the loss of adhesion due to cytotoxicity leads to a time-dependent decrease in the cell-substarte impedance which correlates with target cell killing. Furthermore, since the effector cells are suspended cells they only interact with the effector cells through specific receptors on the cell surface and not with the electrodes in the well. Therefore, the addition of effector cells to the target cells has no or minimal effect on the electronic impedance. In addition, unlike the limitation of a time window of four hours for the chromium-based cytotoxicity assay, there is not time limitation for the electronic-based assay described here. The assay window can be as short as a few minutes or as long as a few days.

Screening for Antibody-dependent Cellular Cytotoxicity (ADCC) Using Electronic Cell Sensor Technology ADCC is a mechanism by which NK cells are targeted to IgG-coated cells resulting in lysis of the antibody coated cells. A specific receptor for the constant region of IgG, called FcγRIII is expressed on the NK cell membrane and mediates activation of NK cells and subsequent ADCC. ADCC is the dominant component of the activity of antibodies against tumors. It is believed that certain tumors bear antigens which are recognized by the humoral immune system. The subsequent interaction of the antibody with the antigen on tumor cells will mark the tumor cells for demise by the innate immune components such as NK cells.

The present invention includes applications relating to ADCC measurement and monitoring. More specifically the present invention includes a method of screening for antibody-dependent cellular toxicity (ADCC) including providing a device such as the RT-CES device(s) (e.g., E-Plates) or a device capable of monitoring cell-substrate impedance operably connected to an impedance analyzer, where the device includes two or more wells for receiving cells, adding target cells to at least two of the wells, adding antibody capable of interacting with the target cells to a test well and an isotype control or non-specific antibody to a control well, adding effector cells to the two or more wells, monitoring impedance of the test well and the control well before and after said adding effector cells and optionally determining a cell index from the impedance, where monitoring impedance includes measuring impedance during at least one time point before and at least one time point after effector cells are added, and determining viability of the target cells in the test well at the desired or chosen time point after the effector cells are added. As previously discussed viability may be determined by comparing the impedance or optionally the cell index of the test well to the control well.

For example, tumor cells expressing a specific antigen or marker may be seeded in ACEA's microtiter plates or devices (for example, 16× or 96× E-Plates) at a predetermined density. Cell adhesion and proliferation in the devices may be continuously monitored by RT-CES system (which includes, for example, a device station or E-Plate station, impedance analyzer and integrated software for controlling the impedance analyzer and device station). At approximately 16-24 hours after starting the experiment, cells may be incubated with an IgG antibody which will interact with the specific target on the tumor cell. The IgG antibody may be allowed to incubate with the target cells for a predetermined amount of time. Also as a control a non-specific IgG antibody (non-specific antibody) may also be added. NK cells or other effector cells may be added at a predetermined ratio of effector cell to target cells. The target cell response to ADCC mediated by the effector cells may be monitored continuously by RT-CES system.

The methods previously disclosed also apply to ADCC measurement, monitoring and screening. In one embodiment, the methods may be automated using the RT-CES system as described. In some exemplary embodiments, the methods may include monitoring impedance at one or more time points prior to adding antibody, one or more time points after adding antibody and before adding effector cells and one or more time points after adding effector cells. In some embodiments, impedance is measured at three or more time points after adding effector cells.

A variety of antibodies may be used with the present invention. The appropriate antibody should be able to bind the target cells via its variable region and to bind the effector cells via its constant region. An antibody may be obtained by screening a library of antibodies. Thus, the antibody may be any suitable antibody such as but not limited to a mouse antibody, a rat antibody, a humanized mouse antibody, a humanized rat antibody and the like.

The viability of target cells and cytolytic activity of the effector cell may be determined by procedures similar to those previously disclosed in the present invention. For example, the viability of target cells may be calculated using the formula, Viability=$\text{Resistance}_{at\ a\ time\ point\ after\ adding\ effector\ cells}/\text{Resistance}_{at\ a\ time\ point\ prior\ to\ effector\ cells}$, where resistance is a component of impedance of the well measured at a chosen frequency. Non-limiting example of the frequency includes ~1 kHz, ~5 kHz, ~10 kHz, ~20 kHz, ~50 KHz, less than 1 kHz, between 1 and 10 kHz, between 10 and 100 kHz, or above 100 kHz. Discussions about this formula have been disclosed above in the present invention. In another example, viability of target cells at a time point after addition of effector cells may be determined by comparing the cell index of the well prior to and after addition of effector cells. Viability of target cells may be calculated as the ratio of the cell index of the well at the time point of interest to the cell index of the well immediately prior to addition of effector cells. Such a calculation has an implicit assumption that the cell index of a well may be approximately proportional to the number of the viable cells in the well and there is little or no cell proliferation of target cells in the well in the time period between the two time points of measurement, one at time of interest and the other immediately prior to addition of addition of effector cells.

Cytolytic activity of effector cells refers to the ability of effector cells to lyse or kill target cells. In one exemplary embodiment of the present invention, the cytolytic activity of the effector cells are expressed as percent cytolysis or percentage of cytolysis, which may be derived at any given time point after adding effector cells to a test well by the equation of {percent cytolysis=(1-cell index of test well/cell index of control well)}, where same number of target cells have been added to both control well and test well, and a specific IgG antibody has been added to test well and a non-specificn, control IgG has been added to control well, and same number of effector cells have also been added to both test well and control well. An implicit assumption for this equation is that cell index follows approximately linear relationship with the number of viable target cells in the well. Thus, if no target cell is killed or lysed by effector cells, cell index of test well will be the same as cell index of control and percent cytolysis is zero. Effector cells have no cytolytic activity. If all target cells are killed or lysed by effected cells, cellmindex of test well will be zero or approximately zero, then percent cytolysis is 1 or 100%. The effector cells have a 100% cytolytic activity. In general, the more the target cells are killed or lysed, the smaller the cell index of test well, and the larger the percent cytolysis. Furthermore, in some embodiments, in above equation to calculate percent cytolysis, cell index is normalized cell index.

Methods to Assay for Complement-mediated Cellular Cytotoxicity in the Presence of Neutrophils or Anti-MHC Antibody Using Electronic Cell Sensor Technology The methods of the present invention may be used to assay for complement-mediated cellular cytotoxicity in the presence of neutrophils or anti-MHC antibody. The complement system is one of the major effector mechanisms of the humoral and innate immunity. Complement proteins bind to tumor cells that have been targeted by IgG and IgM antibodies through interaction with the constant domain of the antibodies. The interaction of complement proteins with the antibody on the surface of tumor cells will lead to the destruction of the tumor cells by the formation of pores on the membrane of target cells by components of the complement pathway or by recruitment of neutrophils which either engulf tumor cells or induce its destruction by granzymes. Neutrophils contain specific receptors which recognize components of the complement system.

Thus the present invention includes a method of assaying for complement-mediated cellular cytotoxicity including providing any one of the disclosed devices capable of monitoring cell-substrate impedance operably connected to an impedance analyzer and having at least two wells, adding target cells to the at least two wells, adding complement and antibody capable of interacting with the target cells to a test well and a complement without antibody or with an isotype control antibody to a control well, monitoring impedance of the test well and the control well before and after adding complement and optionally determining a cell index from the impedance, determining viability of said target cells in the first well at a given time point after adding the complement and antibody by comparing the impedance or optionally the cell index of the test well to the control well.

As with previous applications of the present invention, impedance may be measured at a variety of time points. Among these are at least one time point before adding the complement and at least three time points after adding the complement.

For example, complement-mediated cellular cytotoxicity in the presence of an antibody (IgG or IgM) specific for a particular target on tumor cells alone or in the presence of the antibody together with neutrophils, may be assayed as follows using the RT-CES system: tumor cells may be seeded on ACEA's microtiter plates (for example, 16× or 96× E-Plates) at a predetermined density and the adhesion and proliferation of the cells may be continuously monitored using the RT-CES. At approximately 16-24 hours after the start of the experiment, the cells may be incubated with complement-containing media for approximately an hour. If the effect of antibody on complement-mediated cellular cytotoxicity is being assayed, then a predetermined concentration or concentrations of antibody will be added with the complement to the cells. As a control, complement alone may be added or complement together with an irrelevant antibody or an appropriate isotype control may be added. Similarly, if complement-mediated cellular cytotoxicity is being assayed in the presence of antibody and neutrophils or other effector cells, the cells may be incubated with complement as described in above in the presence of an antibody specific against an antigen expressed by the tumor cells. A predetermined ratio of neutrophils or other effector cells may be added to the wells containing the tumor cells, antibody and complement. The effect of antibody alone or antibody and neutrophil in the presence or absence of complement may be continuously monitored using the RT-CES system. If the cells are incubated with complement and antibody against a specific antigen expressed by tumor cells, it is expected that the antibody dose-dependently sensitizes the target cells to complement-mediated killing. As a result the RT-CES recording of the target cells is expected to decrease in a time-dependent manner due to killing of the target cells. Similarly, addition of effector cells such as neutrophils to cells presensitized with an antibody specific against a particular target on tumor cells in the presence of complement would be expected to result in a time-dependent decrease in the cell-electrode impedance response of the target cells.

EXAMPLES

Example 1

Figure 12A:
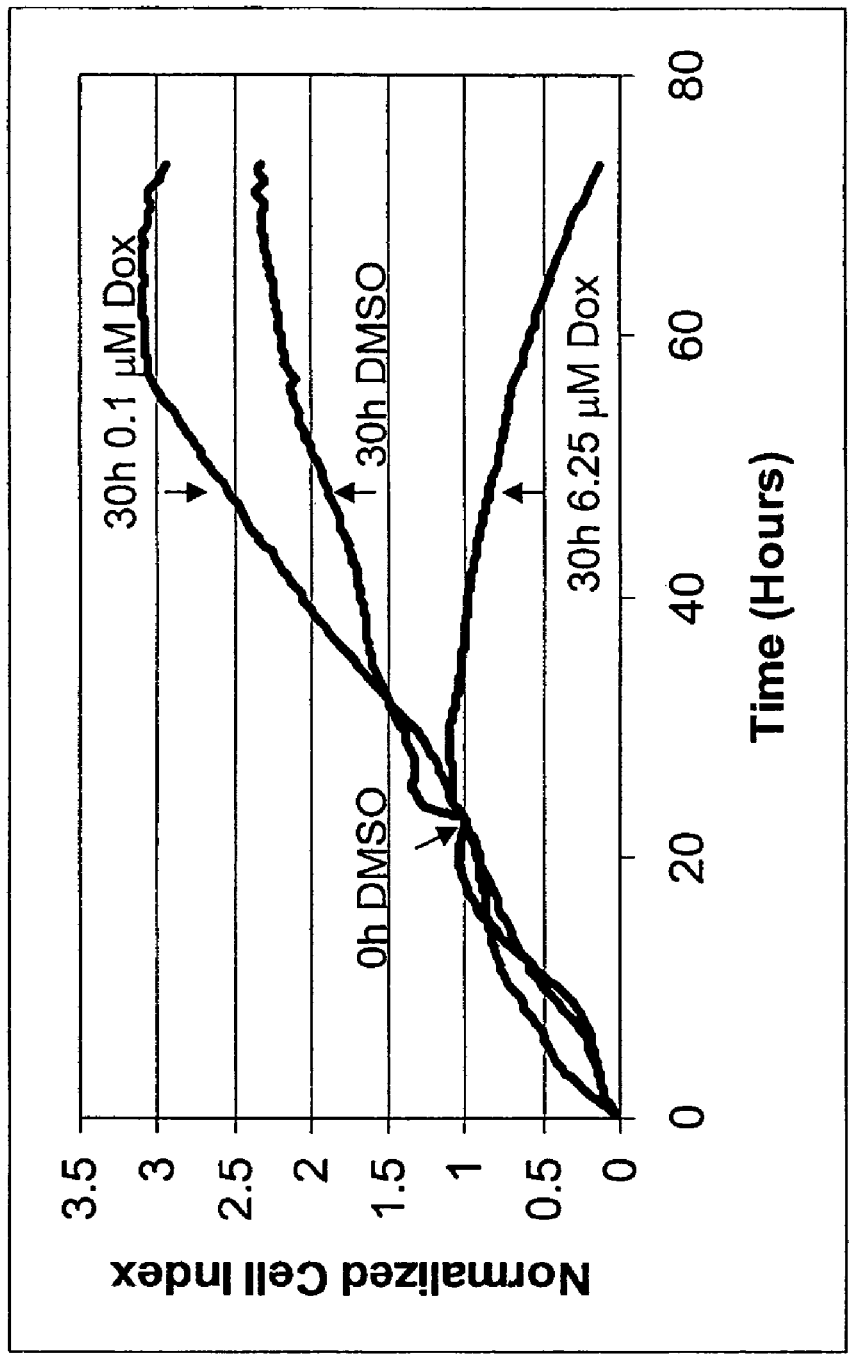
FIG. 12A shows the response of MV522 cells to doxorubicin treatment as monitored using a cell-substrate imepdnace monitoring system of the presnet invention. MV522 cells were seeded onto microtiter devices fabricated with electronic sensor arrays shown in FIG. 1B and were treated with either DMSO or doxorubicin at the indicated time and concentration.
Figure 13A:
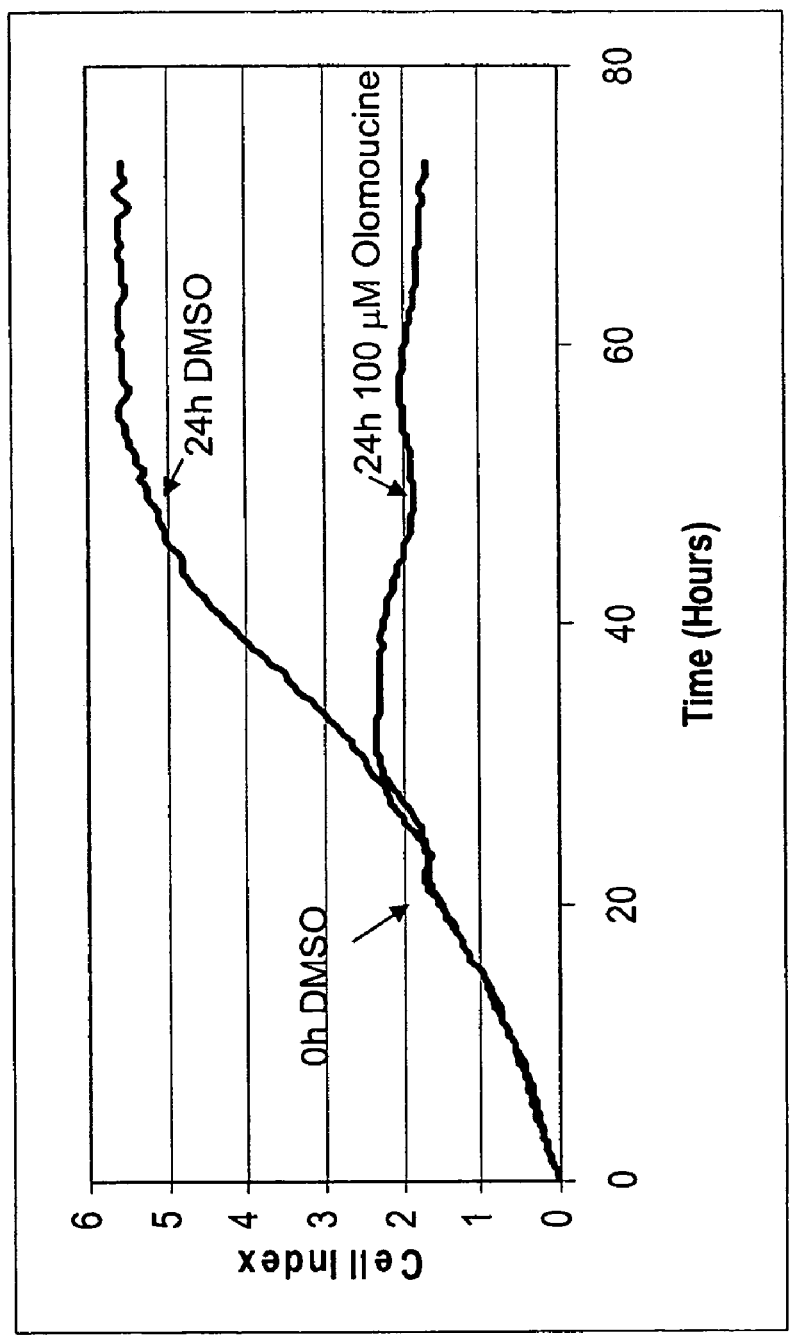
FIG. 13A shows the response of A549 cells to olomoucine treatment as monitored using a cell-substrate imepdnace monitoring system of the presnet invention. A549 cells were seeded onto microtiter devices fabricated with electronic sensor arrays shown in FIG. 1B and were treated with either DMSO or olomoucine at the indicated time and concentration.
Figure 13B:
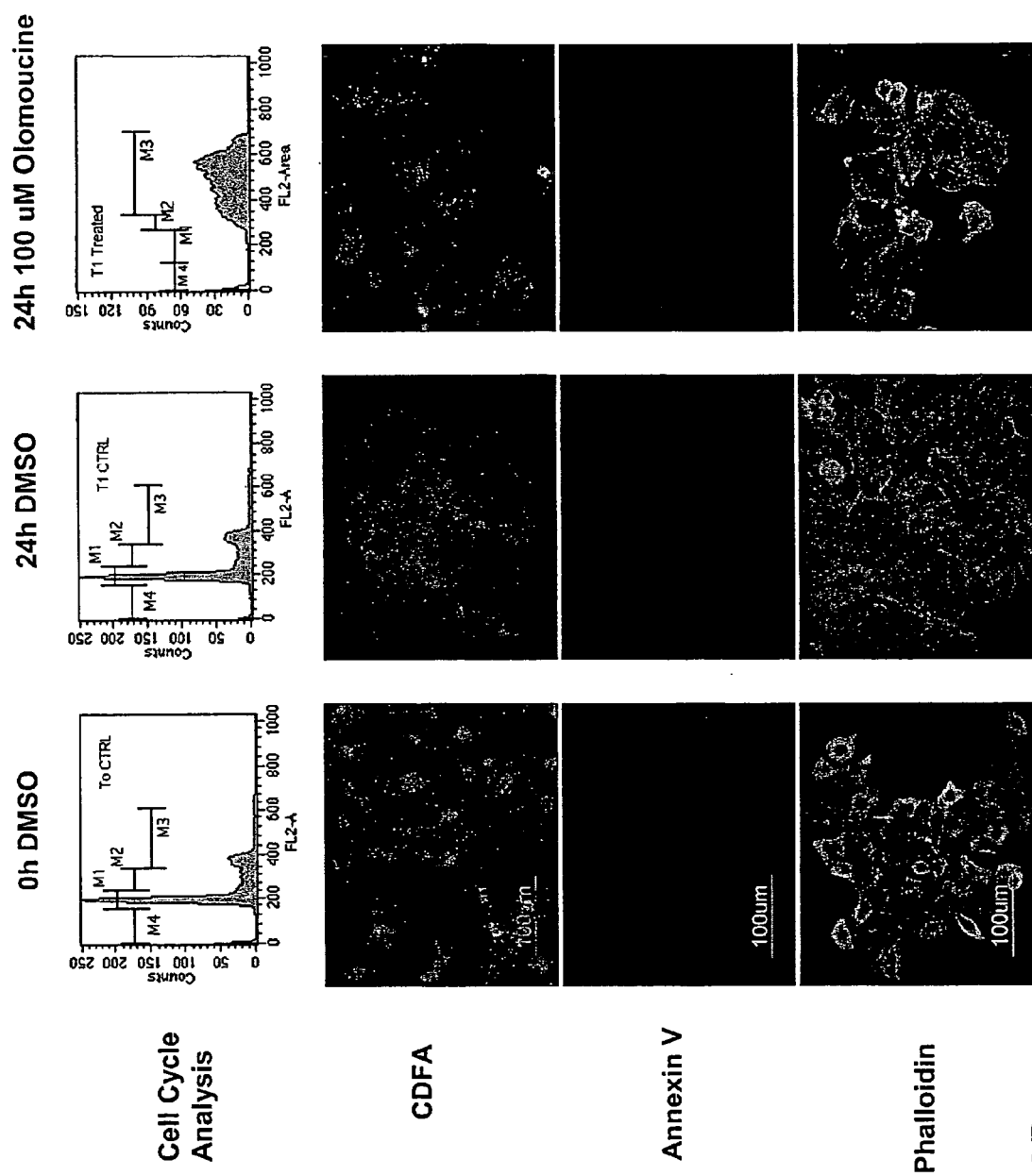
FIG. 13B shows the characterization of the cell biological effect of olomoucine treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 14A:
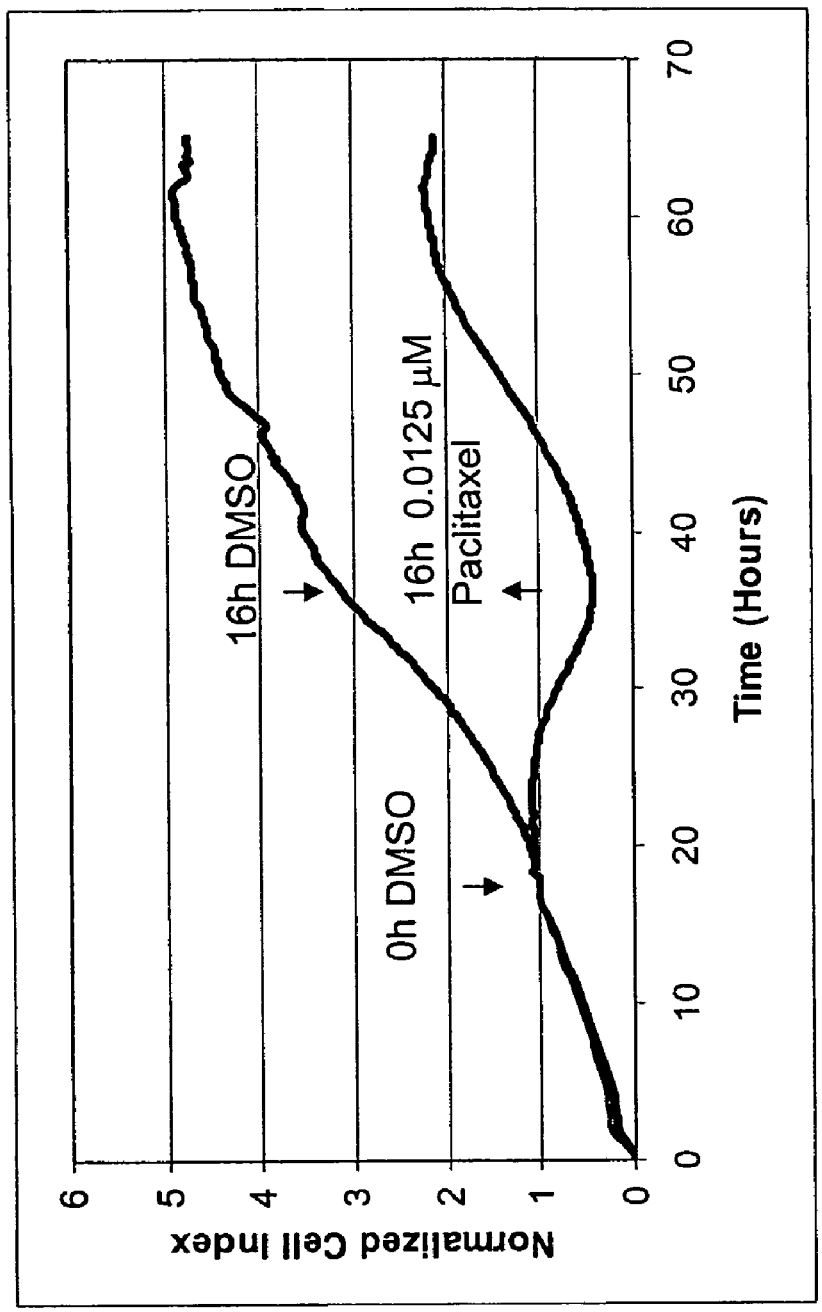
FIG. 14A shows the response of A549 cells to paclitaxel treatment as monitored using a cell-substrate imepdnace monitoring system of the presnet invention. A549 cells were seeded onto microtiter devices fabricated with electronic sensor arrays shown in FIG. 1B and were treated with either DMSO or paclitaxel at the indicated time and concentration.
Figure 14:
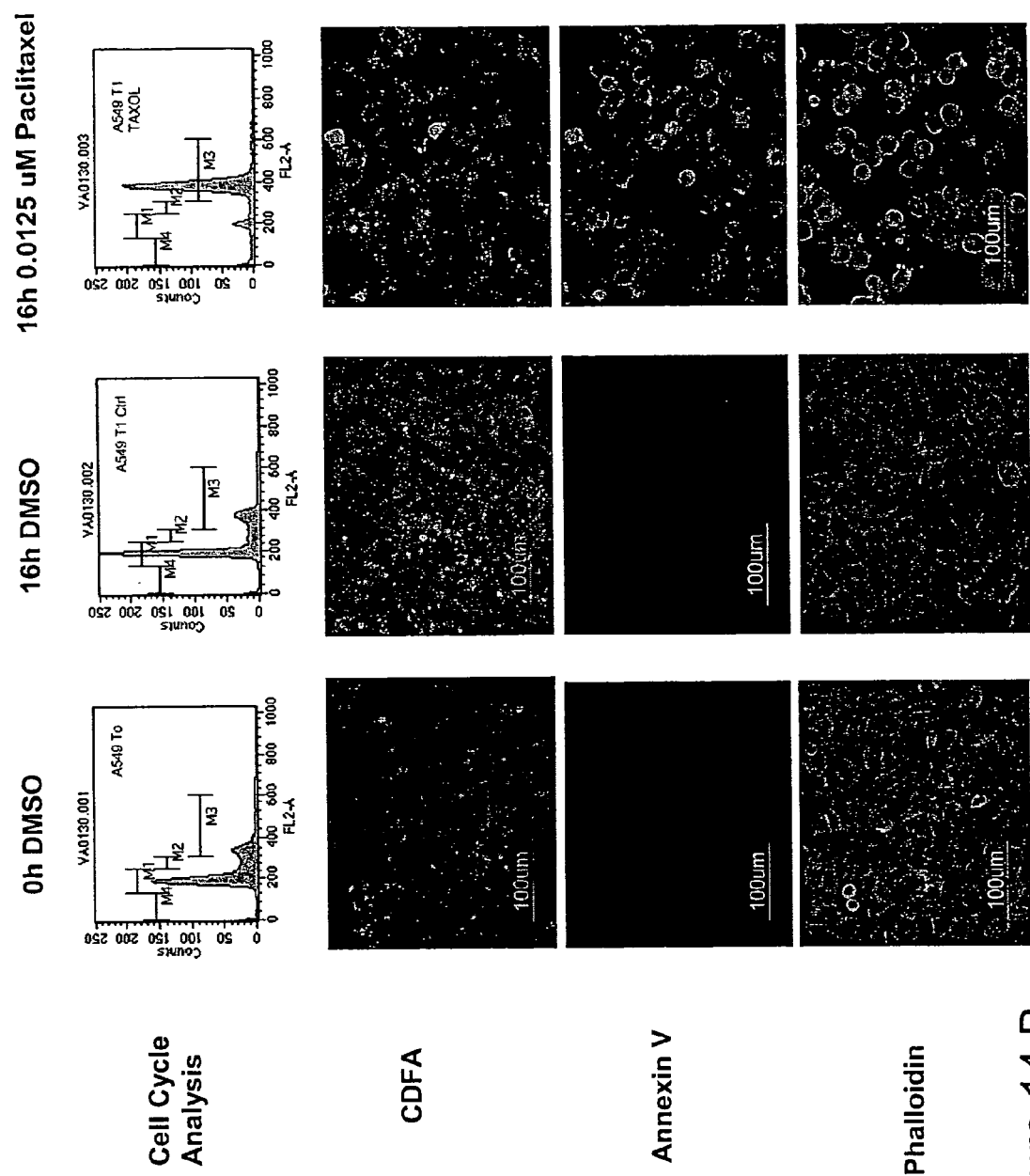
FIG. 14B shows the characterization of the cell biological effect of paclitaxel n treatment on A549 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 15A:
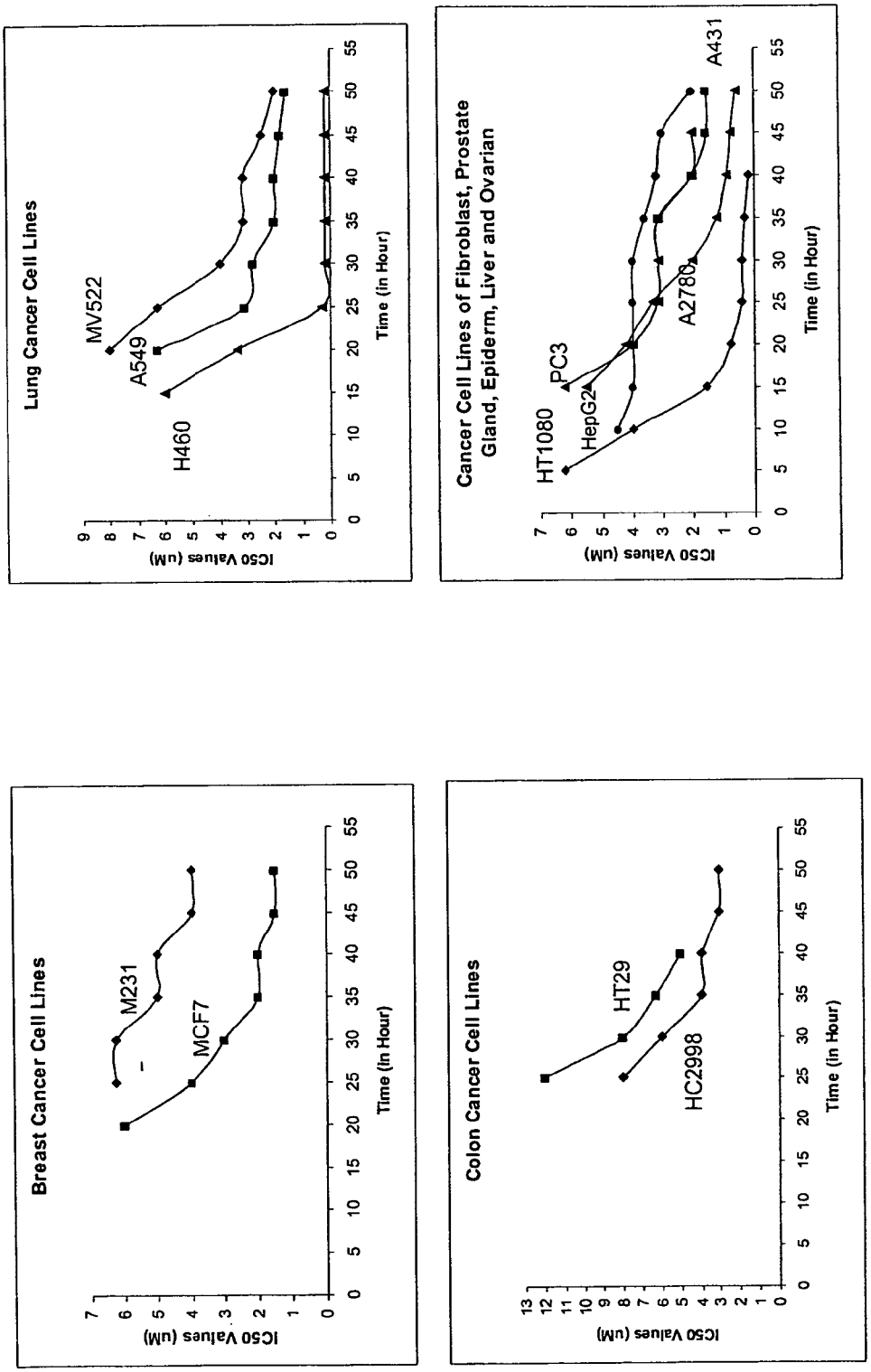
FIG. 15. The time dependent IC values for each compound (15A: Doxorubicin; 15B: Paclitaxel; 15C: Olomoucine; 15D: Tamoxifan) for the indicated cell lines as estimated at 5 hr intervals from the cell index curves obtained using a cell-substrate imepdnace monitoring system of the presnet invention.
Figure 15B:
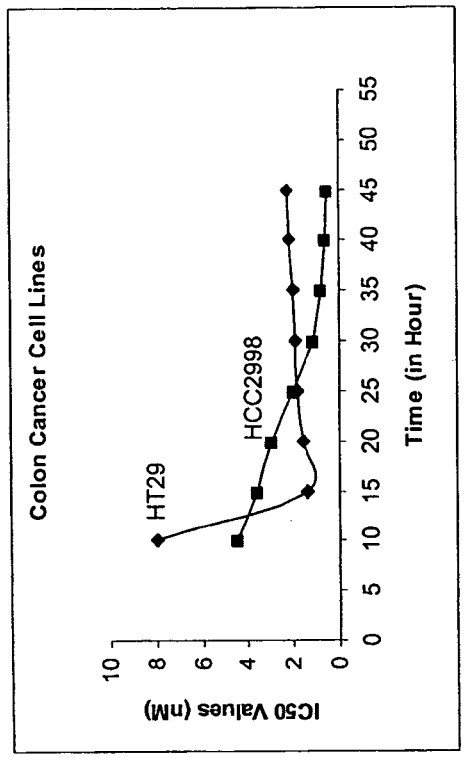
Figure 15B:
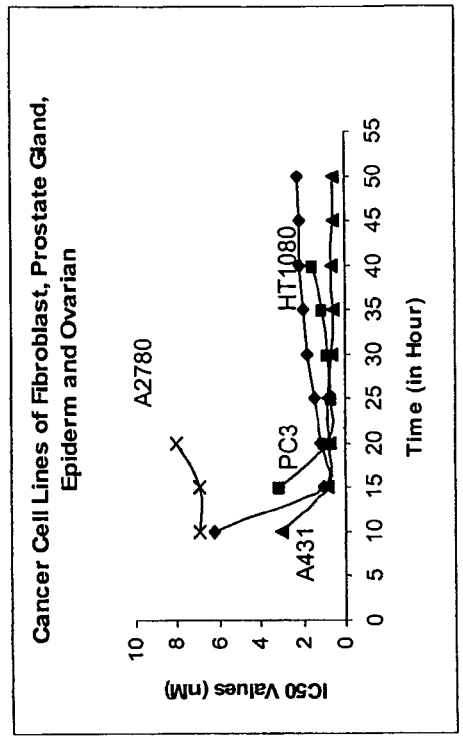
Figure 15B:
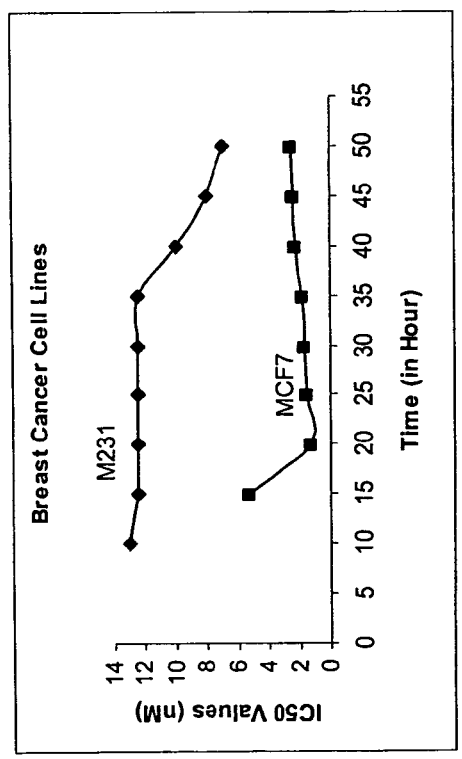
Figure 15B:
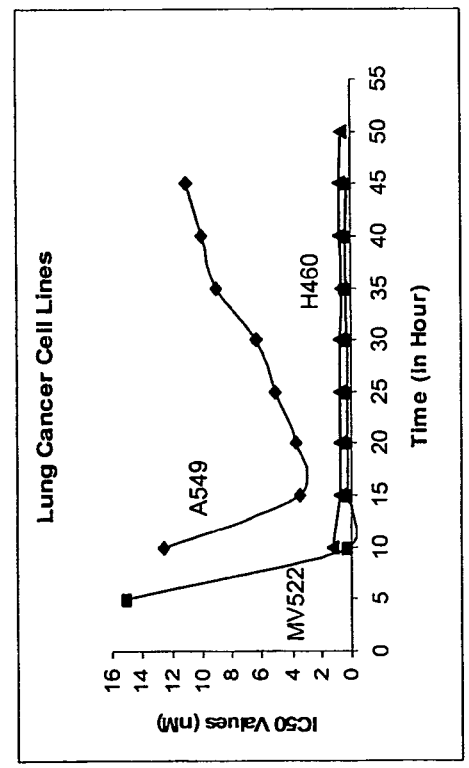
Figure 15C:
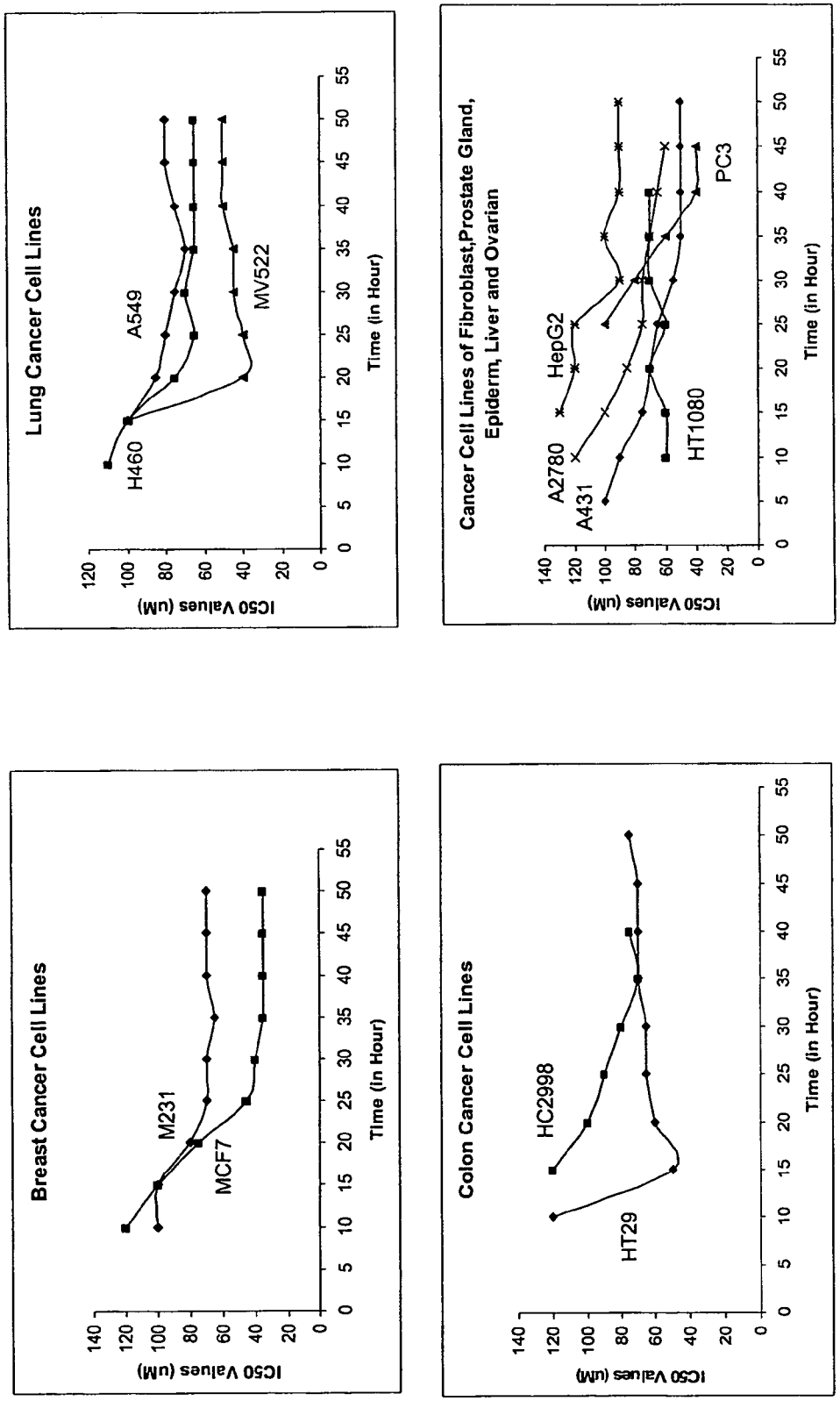
Figure 15D:
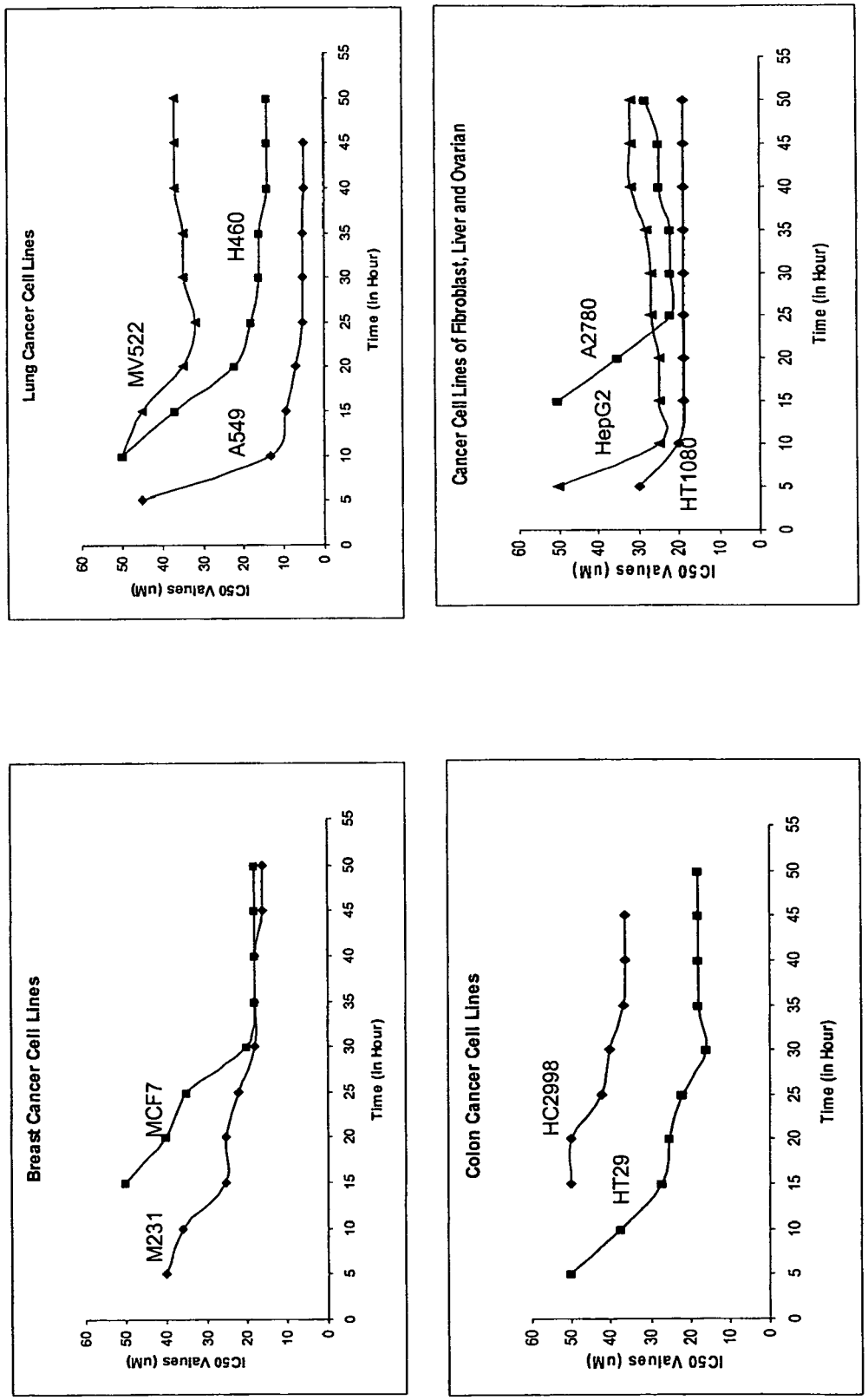
Figure 16B:
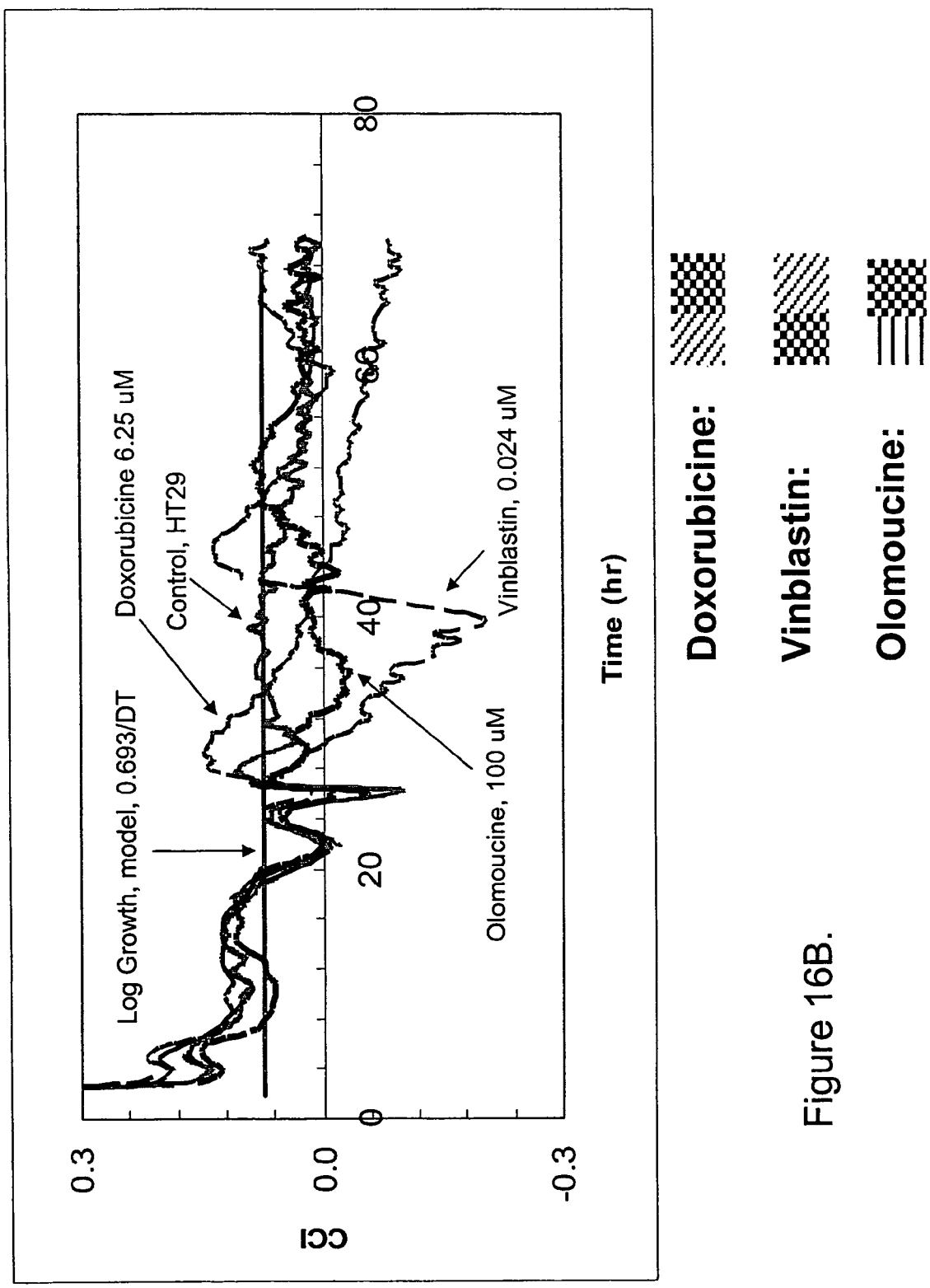
FIG. 16B shows the derived cell change index (CCI) from the cell index curves shown in FIG. 16A. Also shown is the "black-white shading codes" used for different responses based on the convention shown in FIG. 16C.
Figure 17:
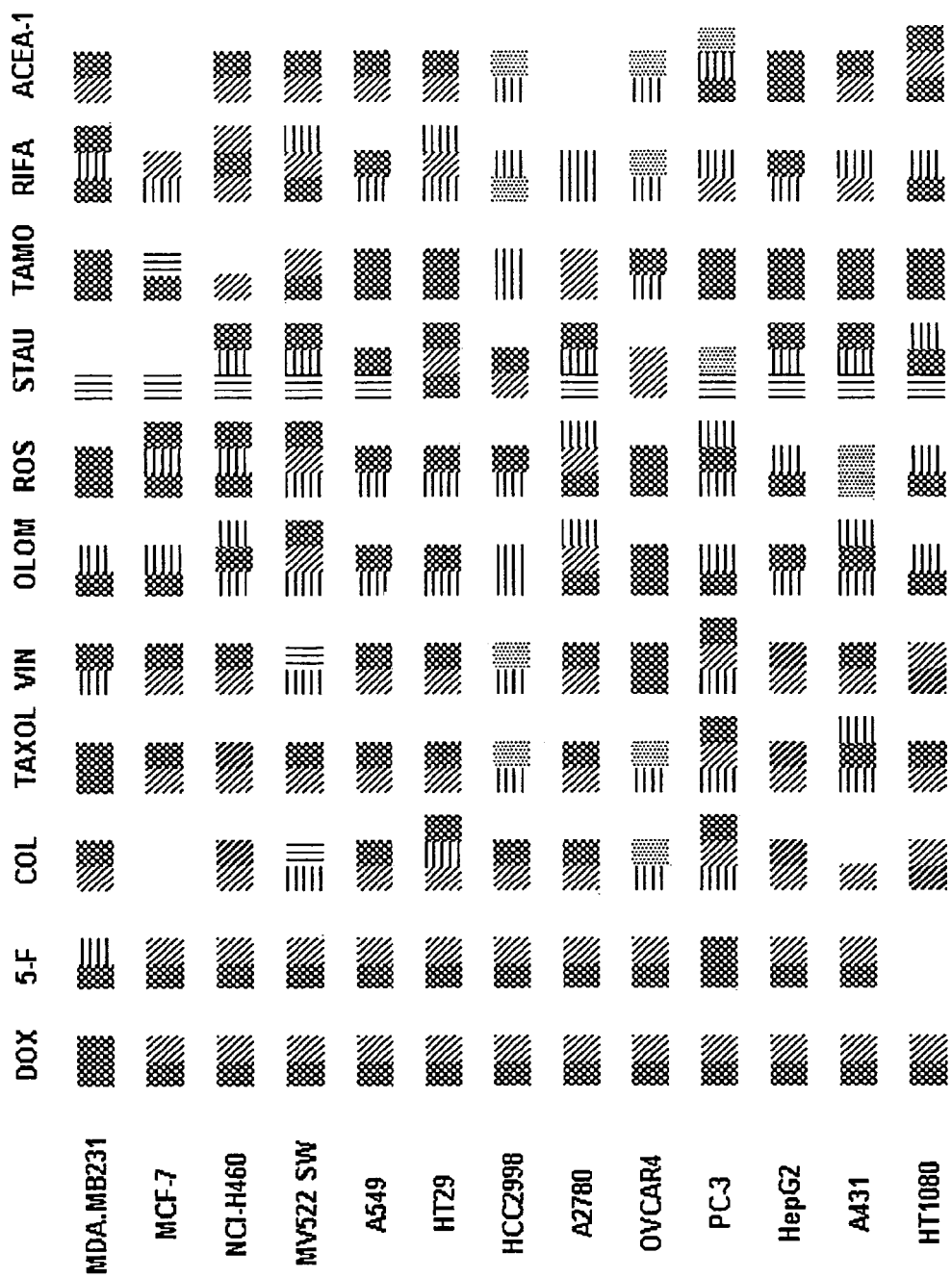
FIG. 17 shows the cell response profile of each cell line tested against the indicated chemotherapeutic agents. For each cell line and compound, the time-dependent cell change index (CCI) was calculated from their corresponding RT-CES responses at an IC50 concentration. (IC 50 is time dependent so that the IC50 concentration at 30 h, or the concentration closest to that, after drug addition is used). The specific CCI curves as related to specific cellular responses were coded according to the convention described in FIG. 16C and displayed in groups of compounds with similar mechanism of action. DOX: doxorubicin; 5-F: 5-Fluorouracil; COL: Colcemid; TAXOL: paclitaxel; VIN: vinblastin; OLOM: Olomoucine; ROS: Roscovitine; STAU: Staurosporine; TAMO: Tamoxifan; RIFA: Rifampicin; ACEA-1: an ACEA test compound.

Profiling of Dynamic Cell Responses to Anti-cancer Drugs Using ACEA RT-CES System In this study, we used the RT-CES system to dynamically monitor cancer cell responses to chemotherapeutic compounds with characterized mechanisms, and to profile the specific cell response patterns. Thirteen cancer cell lines including cancers of breast, prostate, lung, colon, ovary, kidney, fibroblast, and central nervous system were tested (Table 1). Each cancer cell type was treated with 11 chemotherapeutic compounds, classified as DNA damaging agents, protein kinase inhibitors, anti-mitotic drugs, cell cycle specific inhibitors, protein synthesis inhibitors plus a compound of unknown category (Table 2). Dynamic and dose dependent cell-compound interaction patterns were characterized and summarized for all the tested cell lines and compounds. The profiles for three drugs, doxorubicin, olomoucine and paclitaxel against a panel of 12 different cell lines are presented in FIGS. 9, 10 and 11, respectively. In addition, we characterized the biological effect of these compounds on cells by monitoring cell cycle progression, cell viability and morphological status of the cells in an attempt to correlate specific cellular response to the shape of the cell index trace (FIGS. 12, 13 and 14). Furthermore we calculated the time-dependent IC-50 values for each compound against the various cell lines (FIG. 15) and developed an algorithm to calculate Cell Change Index to profile the dynamic cell response of the different chemotherapeutic agents across the different cell lines. Cell Change Index was calculated for the dynamic RT-CES responses of different cell lines to different chemotherapeutic agents using the definitions described above. Based on the time-dependent values of CCI, each CCI value region across the time scale is represented by black-white shading-based coding. For example, if after compound addition, the CCI value (for a particular cell line under a specific compound treatment at the concentration of IC50 value) is nearly zero for certain period of time and then becomes positive, attaining a value about 0.7/DT (DT is doubling). Then the cell response to this compound is represented as a ▤rectangle followed by a ▦rectangle. Examples of such analysis is shown in FIG. 16. The overall black-white shading-based coding map representing the cell dynamic responses to various compounds is shown in FIG. 17.

In summary of this study, we note that using the RT-CES system to screen chemotherapeutic agents results in unique activity patterns that is dependent on the compound itself, the concentration, length of incubation and the cell type. The "signature" patterns of each drug correlates with specific biological phenomenon such as log growth, cell cycle rest, morphology change and cell death. Cell Change Index was a good parameter derived from RT-CES data to mathematically describe cell changes. Cell response profiling based on CCI value indicates that drugs with similar mechanism of action displays similar patterns. Thus, the similarity in the dynamic cell-compound interaction patterns may indicate similarity in mechanism of action, mode of resistance and possibly molecular targets. The RT-CES system can be readily adapted to high throughput dynamic screening and analysis of anti-cancer compounds and the information-intensive approach presented in this study can be applied to profile existing cancer chemotherapeutic agents, screen new compounds and provide insight into the mechanism of action of anti-cancer agents.

TABLE 1

List of cancer cell lines tested against a number of chemical compounds.

| Cancer Cell Line | Organ or Tissue Origin |
| --- | --- |
| MDA.MB231 | Breast Cancer |
| MCF7 | Breast Cancer |
| NCI-H460 | Non-Small Cell Lung Cancer |
| MV522 SW | Non-Small Cell Lung Cancer |
| A549 | Non-Small Cell Lung Cancer |
| HT29 | Colon cancer |
| HCC2998 | Colon cancer |
| A2780 | Ovarian Cancer |
| OVCAR4 | Ovarian Cancer |
| PC-3 | Prostate Cancer |
| HepG2 | Human Hepatosarcoma |
| A431 | Epidermoid Cancer |
| HT1080 | Fibrosarcoma | hours depending on the experiment. The electronic readout, cell-sensor impedance is displayed as a parameter called Cell Index.

Figure 18:
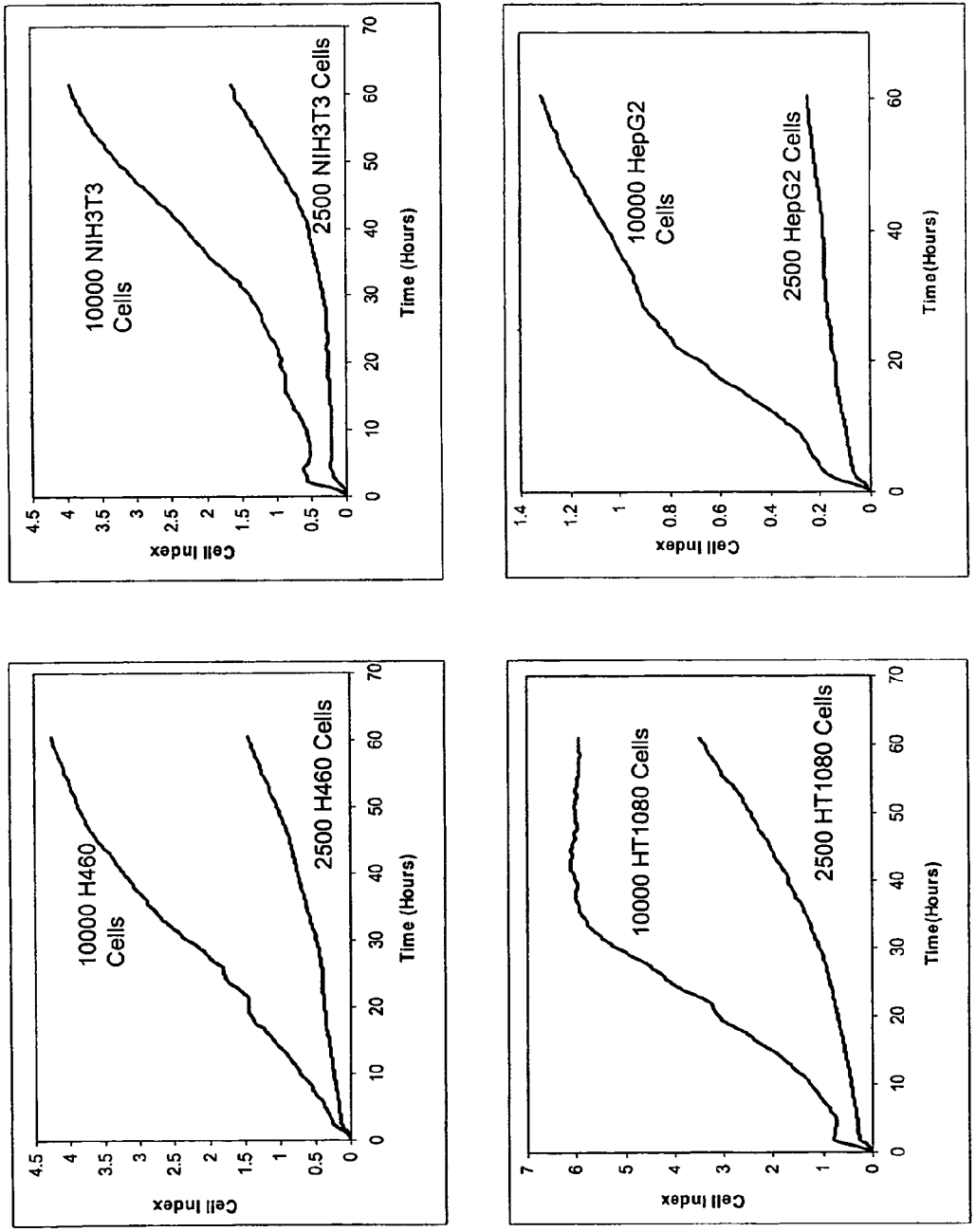
FIG. 18. Dynamic monitoring of cell proliferation. H1080 fibrosarcoma cells, H460 lung cancer cells, HepG2 hepatosarcoma cancer cells and NIH3T3 mouse fibroblast cell lines were seeded at a density of 2500 and 10,000 cells per well of ACEA 96× e-Plate device. The adhesion, spreading and proliferation of the cells were dynamically monitored every 30 minutes using a cell-substrate imepdnace monitoring system of the presnet invention.

Drug Treatment and Cytotoxicity Assessment. For each cell type the optimum cell concentration was chosen based on their respective proliferation pattern (FIG. 18). The indicated cell numbers were seeded per well of ACEA's 16× or 96× E-Plate™ (exemplary devices of the present invention) in 100 μL final volume. The attachment, spreading and proliferation of the cells were continuously monitored every 30 minutes using the RT-CES system (an exemplary system of the present invention). Approximately 24 hours after seeding, when the cells were in the log growth phase, the cells were treated with 100 μL of the indicated compounds dissolved in cell culture media. The cells were also treated with DMSO, which served as vehicle control. Depending on the experiment, the final DMSO concentration in the media was in the range of 0.25%-0.5%.

MTT Assay. Increasing numbers of NIH3T3 cells were seeded in 16× e-plate and monitored by RT-CES to obtain the corresponding Cell Index. The media was immediately

TABLE 2

List of chemical compounds used in the study of profiling cell dynamic responses to a number of anti-cancer compounds.

| Machanisms of Compound Action Effect on DNA replication or Topology | Chemical Compounds | concentration From High to Low (dilution factor:2) |
| --- | --- | --- |
| | Doxorubincin | 6.25 uM-0.098 uM |
| | 5-Fluorouracil | 50 uM-0.78 uM |
| Mitotic Poisons | | |
| | Colcemid | 3.125 uM-0.049 uM |
| | Paclitaxol | 0.0125 uM-0.00019 uM |
| | Vinblastin | 1.56 uM-0.024 uM |
| Cell Cycle Arrest | | |
| | Olomoucine | 100 uM-1.56 uM |
| | Roscovitine | 50 uM-0.78 uM |
| Kinase Inhibitors | | |
| | Staurosporine | 5 uM-0.078 uM |
| | Tamoxifan | 50 uM-0.78 uM |
| Protein synthesis Inhibitor | | |
| | Rifampicin | 100 uM-1.56 uM |
| Unknown type | | |
| | ACEA-1 | |

Example 2

Cytotoxicity Profiling

Methods

Cells. All the cells used in this study were obtained from ATCC and maintained at 37° C. incubator with 5% CO$_2$ saturation. H460, HepG2 and HT1080 cells were maintained in RPMI media containing 5% FBS and 1% penicillin and streptomycin. NIH3T3 cells were maintained in DMEM media containing 10% FBS and 1% penicillin and streptomycin.

Cell Proliferation Assays. For each of the cell type, the indicated number of cells was seeded per well in 96× microtiter plates (e-plate™) with incorporated electrode structures in individual wells device in 100 μL of media. The attachment, spreading and proliferation of the cells were continuously monitored every 30 minutes using the RT-CES™ system (a cell-substrate impedance monitoring system. Cell proliferation was monitored for a period of 48-72 hours depending on the experiment. The electronic readout, cell-sensor impedance is displayed as a parameter aspirated and the cells were then assayed by using the standard MTT assay according to the manufacturer's protocol.

Flow Cytometry. A549 cells were seeded at a density of 500,000 cells/well in 60 mm tissue culture dishes. Approximately, 24 hours after seeding, the cells were treated with the indicated final concentration of Olomoucine and 16 hours later the cells were washed with PBS, trypsinized, washed twice with PBS and fixed in 70% methanol and stored at 4° C. until the staining step. The cells were stained with propidium iodide and analyzed by FACS using a wavelength of 488 nm.

Monitoring Dynamic Cell Proliferation in Real-Time Using the RT-CES

In order to assess dynamic cell proliferation using the RT-CES system, H460 human lung cancer cells, H1080 fibrosarcoma cells, HepG2 human hepatosarcoma cells and NIH3T3 mouse fibroblasts were seeded at 2500 and 10,000 cells per well in triplicate in ACEA's 96× e-plate™. The cells were continuously monitored every 30 minutes using the RT-CES system for the indicated period of time (FIG. 18). As shown in FIG. 18, each cell type has its own characteristic kinetic trace, based on the number of cells seeded, the overall size and morphology of the cells and the degree to which the cells interact with the sensor surface. Also, the adhesion and spreading kinetics as well as time when the cells enter the log growth phase is characteristic of each of the indicated cell lines and therefore offers an excellent internal control and a way to standardize and validate stock cultures during different phases of the manufacturing process.

Figure 19:
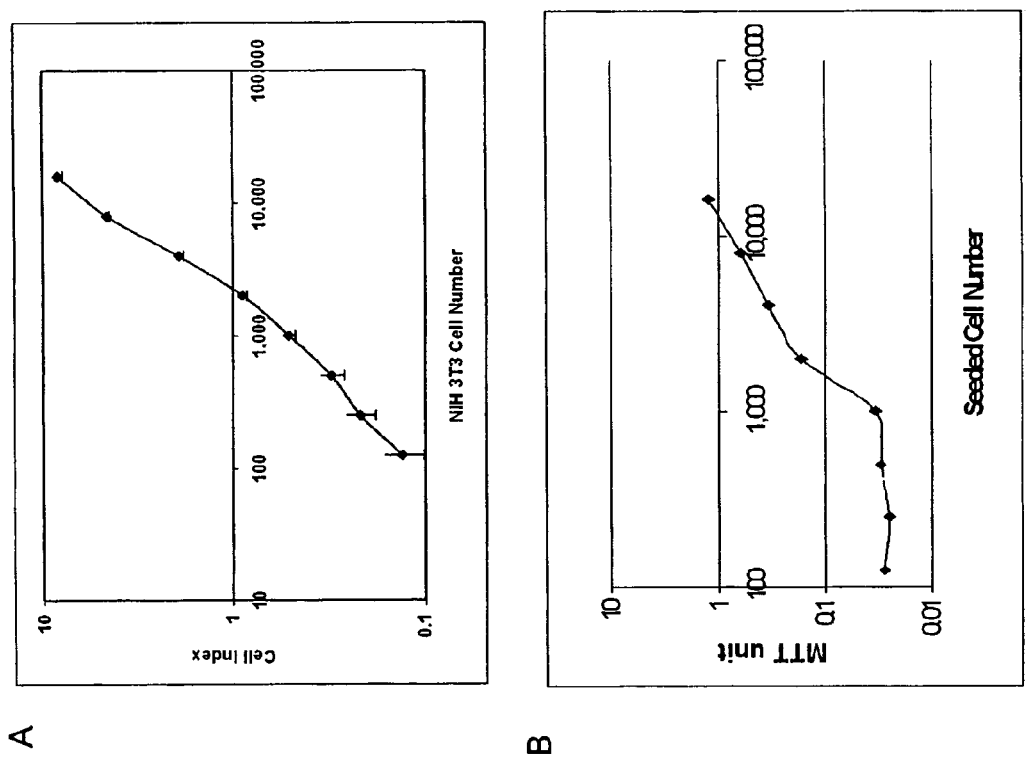
FIG. 19. Correlation between cell-substrate impedance measurement (as shown here, Cell Index) and number of cells seeded and comparison of Cell Index with MTT. (A) Increasing numbers of NIH3T3 ranging from 100 cells all the way up to 10,000 cells were seeded in a device of the present invention and the cells were monitored for 10 hours at which point the Cell Index was obtained. The Cell Index value was plotted against the corresponding number of cells. (B) The cells described in FIG. 19A were assayed by MTT assay at the end of the experiment and the optical density at 590 nm was plotted against the number of cells seeded.

To ascertain that the RT-CES units of Cell Index correlates with the number of the cells in the well, increasing numbers of NIH3T3 cells were seeded in ACEA 16× e-plate™ and were monitored for up to 10 hours, at which time the Cell Index was acquired. FIG. 19A shows a plot of Cell number seeded versus the Cell Index obtained and indicates that for this particular cell type the RT-CES system could detect as little as 100 cells and the readout is linear by two orders of magnitude all the way up to 10000 cells. In addition, at the end of the experiment described in FIG. 19A, the cells were also assayed by the MTT assay. As shown in FIG. 19B, even at up to 1000 cells the MTT assay is not appreciably different than background values and for cell numbers exceeding 1000, then the MTT units correlates with the number of cells seeded in a linear fashion. However, it is important to remember that while the RT-CES system is capable of dynamic and continuous measurements, for comparative reasons the experiment described in FIG. 19 was only conducted at a single point, since MTT is a single point assay.

Assessment of Drug Interaction with Target Cells Using the RT-CES™ System

To assess drug potency using the RT-CES system, the IC-50 value of Tamoxifen was determined for different cell lines and compared with MTT assay at 48 hours after Tamoxifen addition. According to Table 3, the IC-50 values obtained for Tamoxifen for the different cell lines using the RT-CES system is very consistent with the values obtained by the MTT assay, indicating that the RT-CES system can be used to assess the potency of various drugs against different adherent cell lines.

Figure 20:
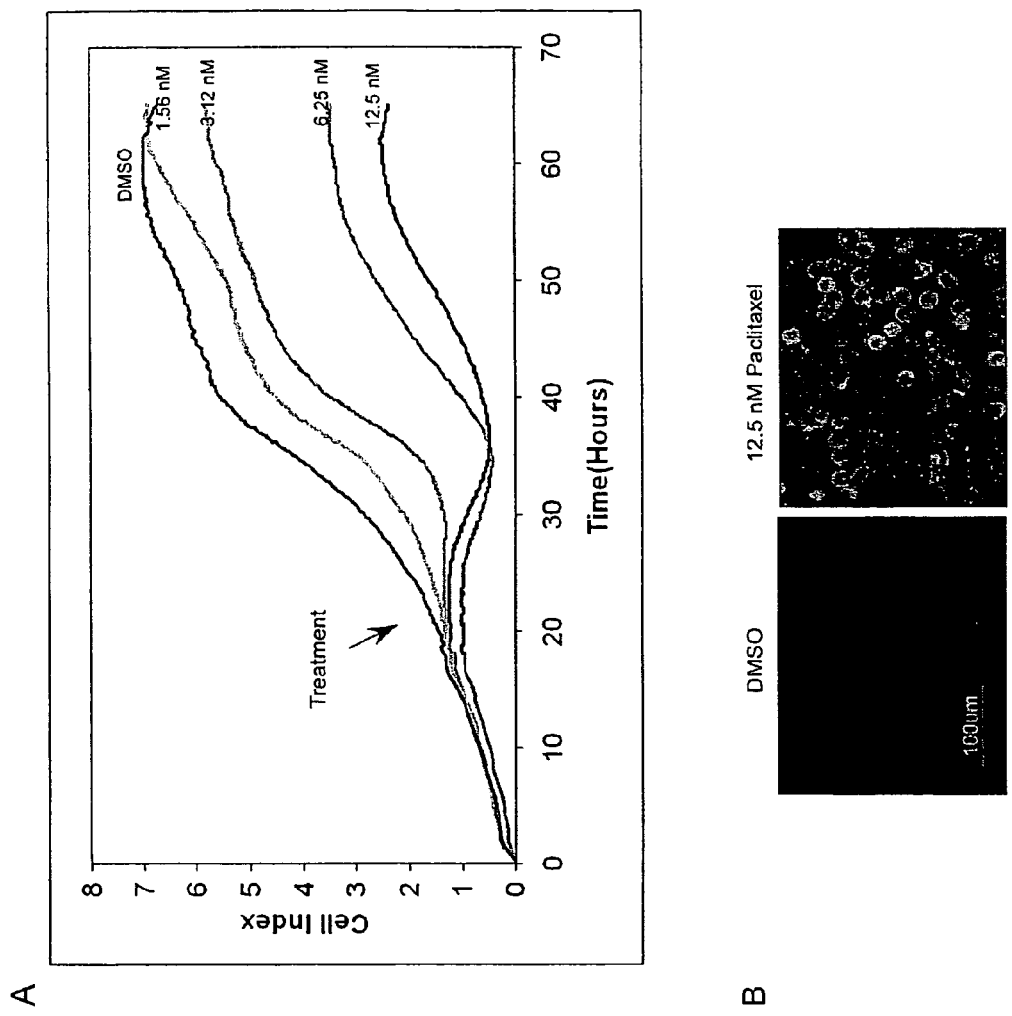
FIG. 20. Dynamic monitoring of drug interaction with target cells using a cell-substrate imepdnace monitoring system of the presnet invention. (A) A549 cells were seeded in a device of present invention at a density of 10,000 cells per well and the cells were continuously monitored up to 24 hours at which point paclitaxel was added at the indicated final concentrations. (B) Annexin V staining of A549 cells treated with DMSO or 12.5 nM paclitaxel for 20 hours. The cells were observed with fluorescence microscope and images were captured with an attached digital camera.

In order to observe the kinetics of drug interaction with target cells, A549 non-small lung cancer cells were seeded in ACEA 96× e-plate™ and continuously monitored until the cells reached the log growth phase at which point different concentrations of paclitaxel were added to the cells at the indicated final concentration. As shown in FIG. 20A, paclitaxel at the highest concentration initially induces a cytotoxic effect which is mainly due to cell death as judged by Annexin V staining (FIG. 20B). Remarkably, the cells recover from the initial cytotoxic effect of the drug and start to re-proliferate. While it remains to be determined if this phenomenon is due to metabolism and inactivation of paclitaxel or due to the emergence of paclitaxel-resistant subpopulation, this experiment clearly exemplifies the tremendous advantage of real-time measurement which is offered by the RT-CES system and allows the user to the opportunity to observe and assess the entire history of drug interaction with the target cells which provides further information in addition to cell viability or cytotoxicity. The phenomenon observed in FIG. 20A would've been easily missed by traditional single-point assays such as MTT.

Figure 21:
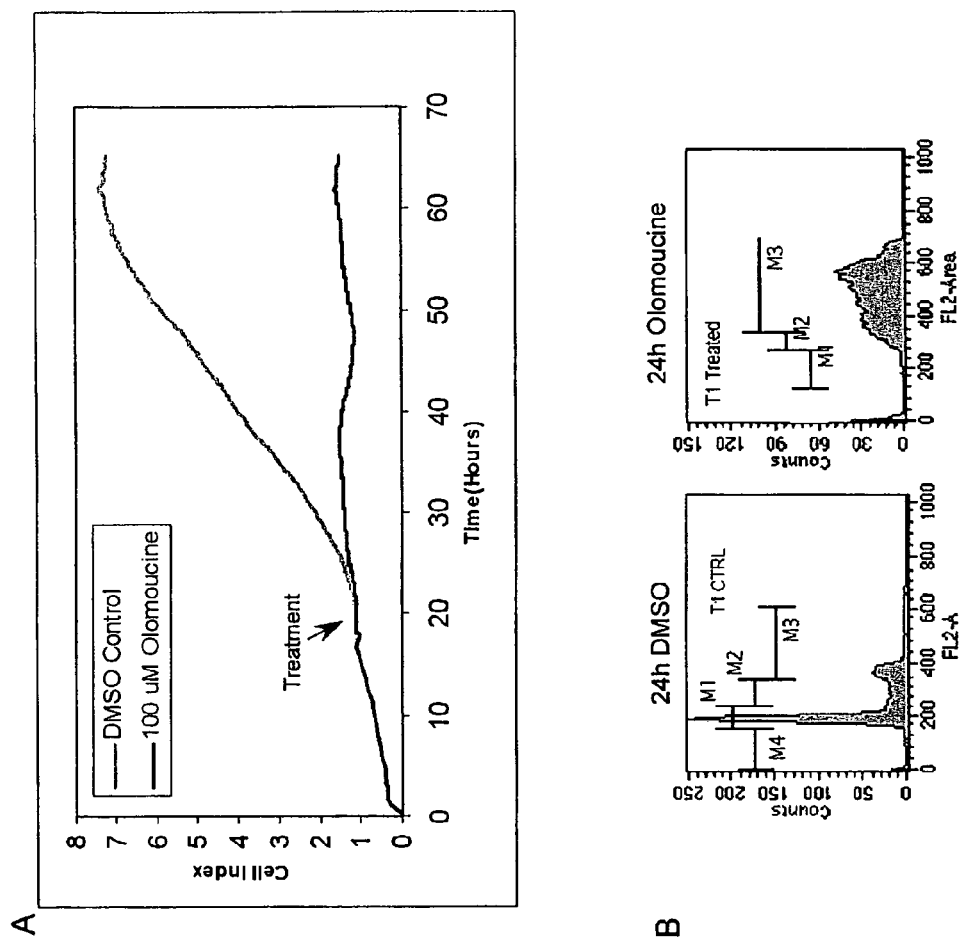
FIG. 21. Dynamic monitoring of cell cycle arrest using a cell-substrate imepdnace monitoring system of the presnet invention. A549 cells were seeded in a device of present invention at 10,000 cells per well and continuously monitored using the RT-CES. The cells were treated with either (A) DMSO or 100 µM Olomoucine (B) A549 cells growing on tissue culture dishes for 20 hours were treated with DMSO or 100 µM Olomoucine. Cell cycle analysis was performed by flow cytometry.

Yet another major advantage of using the RT-CES system to continually monitor the interaction of drugs with target cells is that the user can obtain insight into the mechanism of action of the drug of interest. To demonstrate this point, A549 cells were seeded in ACEA 96× microtiter device and continually monitored by the RT-CES. The cells were treated with either DMSO as the vehicle control or with 100 μM Olomoucine which is a CDK inhibitor and induces cell cycle arrest either at G1→S transition or at the G2→M transition, depending on the cell line. As shown in FIG. 21A addition of Olomoucine to exponentially growing A549 cells causes the trace of the Cell Index recordings of the cells to level off and remain in a steady state that is reminiscent of cell cycle block, where the cells are neither proliferating nor dying off. The control cells treated with DMSO continue to proliferate until they reach confluence, at which time they are contact inhibited and the Cell Index recording levels off. To demonstrate that the effect of Olomoucine on A549 cells as monitored by the RT-CES was indeed due to an arrest of the cell cycle, A549 cells growing on tissue culture dish were treated with the same concentrations of DMSO and Olomoucine and subjected to flow cytometry analysis. As shown in FIG. 21B, the flow cytometry analysis indicates that treatment of A549 cells with the indicated concentration of Olomoucine induces cell cycle arrest at the G2→M transition, where CDKs such as CDK2 is active. Taken together, using the RT-CES system to dynamically monitor drug interaction with the target cells offers the user the opportunity to understand the mechanism of drug action and its mode of interaction with the target cell.

In order to assess the RT-CES system for analysis of cytotoxicity, the interaction of A549 cells was examined with cytotoxic agents with different mechanism of action. FIG. 22 shows the characteristic trace of A549 cells monitored by RT-CES™ and treated with different concentrations of 5-fluorouracil, vinblastine and staurosporine. According to FIG. 22, dynamic monitoring of the interaction of the indicated cytotoxic agents leads to the generation of characteristic kinetic patterns that is dependent on the cellular background, the concentration of the drug, the duration of exposure and the mechanism of drug action. Since each compound has its own characteristic pattern, these kinetic traces could potentially be used to determine the mechanism of action of compounds with unknown targets by comparing the kinetic profile to the profile of compounds with known mechanism of action.

Label-free and dynamic monitoring of cell proliferation, viability and cytotoxicity using the RT-CES system offers very distinct and important advantages over traditional end-point assays. It allows for built in internal quality control to assure consistency and reproducibility between the different assays. Dynamic monitoring allows for observation of the entire episode of drug interaction with target cells and the user can therefore have a better understanding of the mode and mechanism of drug interaction. Furthermore, the actual kinetic trace of the drug interaction with the target cell is very significant because it can offer clues as to the mechanism of drug interaction with the target cell. Finally, since each compound or drug has its own characteristic profile with respect to its interaction with target cells, the RT-CES system can be used as a way to determine the mechanism of action of drugs with unknown targets.

TABLE 3

Comparison of IC-50 values for Tamoxifen treatment of different cancer cell lines using the RT-CES system versus MTT assay. The indicated cell lines were seeded in ACEA 16X devices and monitored by RT-CES. Approximately 24 hours later, the cells were treated with increasing concentrations of Tamoxifen and then continually monitored by RT-CES. The experiment was stopped about 48 hours later and the cells in the 16X devices (16X E-Plates) were assayed by using MTT. The IC-50 values derived from RT-CES system are time-dependent. In the table, the IC-50 values at about 48 hrs after compound treatment are shown for RT-CES system determination and MTT assay.

| Cell Type | RT-CES ™ | MTT Assay |
|---|---|---|
| HT1080 | 2.4 μM | 30.0 μM |
| NIH3T3 | 16.0 μM | 19.0 μM |
| HepG2 | 15.2 μM | 16.2 μM |
| HUEVEC | 7.5 μM | 8.0 μM |

Example 3

Figure 23:
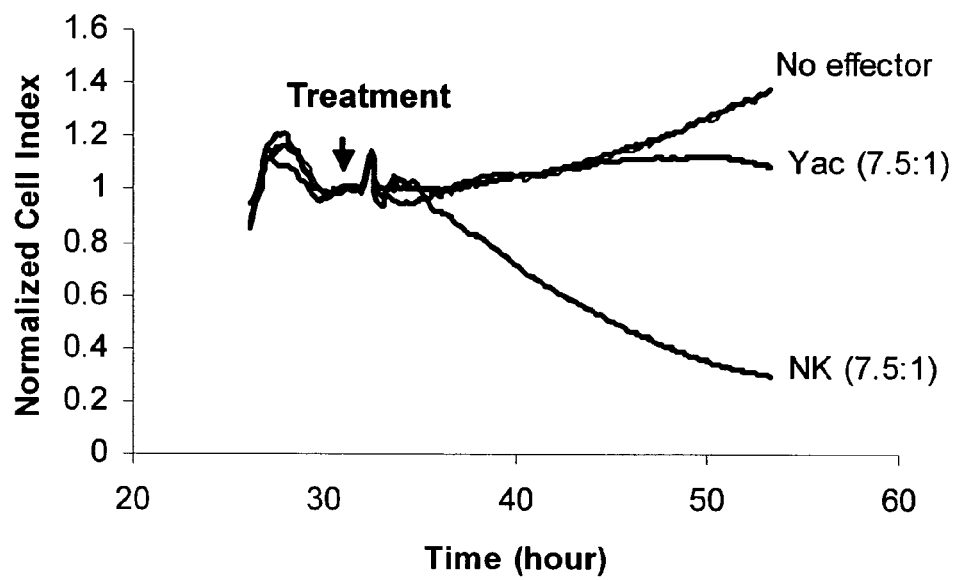
FIG. 23. NIH3T3 cells (target cells) were seeded at a density of 20,000 cells/well on ACEA's microtiter plate (16× E-Plate). The adhesion and proliferation of the NIH3T3 cells were monitored continuously on RT-CES. The cells were allowed to proliferate to log growth phase and then treated with effector NK cells at a ratio effector: target of 7.5:1. As a control the target cells were treated with media alone or with effector cells that lack the killing ability.
Figure 24:
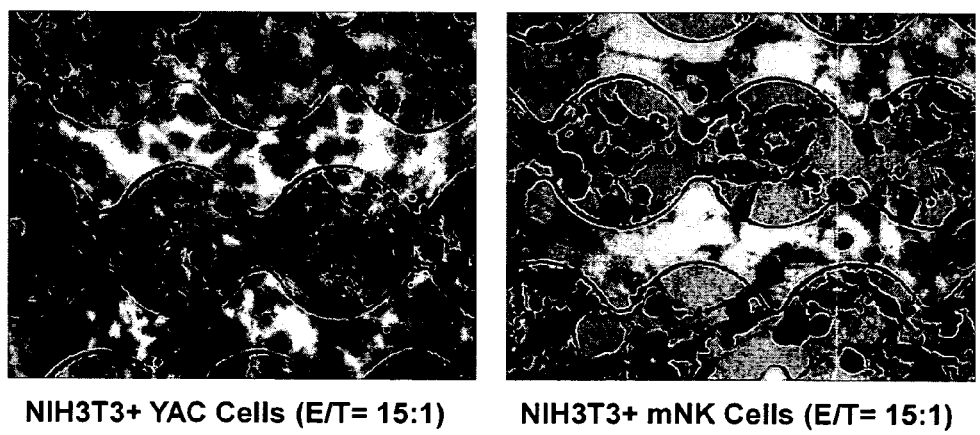
FIG. 24. The NIH3T3 target cells described in FIG. 23 were washed, fixed in methanol and stained with Giemsa blue dye at the end of the assay. The cells were visualized and photographed using a lightmicroscope connected to CCD camera. (A) The cytotoxic effect of the NK cells (effector cells) upon the target cells is apparent by empty gaps in the bottom of the plate, where the target cells have undergone cell death due to interaction with the effector cells. (B) The control effector Yac cell line has no effect on target cells as assessed by the absence of gaps seen in A.

Demonstration of NK-mediated Cell Killing of NIH3T3 Target Cells Using the RT-CES System NIH3T3 cells (target cells) were seeded at a density of 20,000 cells/well into wells of ACEA's 16× microtiter plates (16× E-Plate). The cells were monitored continuously using the RT-CES and were allowed to adhere and proliferate overnight. After 18 hours the cells were incubated with effector NK cell line at an effector to target ratio of 7.5:1. The target cell response was continuously monitored for the next 24 hours. As a control a mouse NK cell line which was deficient in its killing ability, Yac, was also added at an effector to target ratio of 7.5:1 or alternatively only 100 uL of media was added to the cells. As indicated by FIGS. 23 and 24, the mouse NK cell line mediates target cell killing as evidenced by a drop in the cell index number over time which is indicative of cell death. On the other hand the control Yac cell line did not have a major effect on target cells as did the addition of media alone. This experiment indicates that effector cell killing of target cells can be monitored in real-time using the RT-CES system.

Example 4

Testing of Cytolytic Activity in Human and Murine NK Cell Lines

The present application discloses a label free assessment or monitoring of NK cell-mediated cytolytic activity that utilizes a microelectronic sensor-based platform system, the RT-CES (real time electronic sensing) system. Using this system, a human and a murine NK cell lines were both tested for their cytolytic activities using 9 different target cell lines, including cancer cell lines commonly used in the field. The quantitative and dynamic measurement of NK-cell mediated cytolysis was performed on RT-CES system without any labeling steps and reagents. The experimental results are consistent. Moreover, RT-CES system offers fully automated measurement of the cytolysis in real time, which enables a large scale screening of chemical compounds or genes responsible for the regulation of NK cell-mediated cytolytic activity Cells. The NK 92, the NIH 3T3 cell line, and all the cancer cell lines used in these experiments were purchased from ATCC. The mouse NK cell line (mNK) was provided by Dr. Hui Shao of University of Louisville. All the cell lines were maintained at 37° C. incubator with 5% $CO_2$. The NK92 and mNK lines were maintained in Alpha MEM with 2 mM L-glutamine, 1.5 g/L Sodium bicarbonate, supplemented with 0.2 m inositol, 0.1 mM 2-mercaptoenthanol, 0.02 mM folic acid, 12.5% horse serum, 12.5% FBS, and 100-200 U/ml recombinant IL-2. Other cancer cell lines were maintained in RPMI media containing 5% FBS and 1% penicillin and streptomycin (GIBCO). The NIH 3T3 cells were maintained in DMEM media containing 10% FBS and 1% penicillin and streptomycin.

RT-CES system. The system includes three components: the analyzer and e-plate station, the integrated software, and 16-well or 96-well e-plates (16× or 96× E-Plates, see above description). The e-plate station or device station is placed inside the incubator and connected to the analyzer outside the incubator through a thin cable. The e-plate containing the cells is placed onto the e-plate station inside the incubator and the experiment data are collected automatically by the analyzer under the control of integrated software.

Cytolytic analysis. Target cells were seeded into the wells of either 16-well or 96-well e-plate in 100 μl of media. Cell growth was dynamically monitored using the RT-CES system for a period of 24-34 hours, depending on the experiment until they reached log growth phase and formed a monolayer. Effector cells at different concentrations were then directly added into individual wells containing the target cells. For background control, effector cells were added to a well without target cells. After addition of the effector cells, the e-plate was returned to the e-plate station and the measurements were automatically collected by the analyzer every 15 minutes for up to 20 hours.

Cell morphology analysis by microscopy The effect of NK cell-mediated cytolysis on target cells was examined using a Nikon upright microscope. When Cell Index reached 50% of the control upon addition of effector cells, cells were fixed in 80% methanol for 5 minutes and stained with Giemsa blue. The morphology of the cells was examined by microscopy and photographed using an accompanying CCD camera.

Experiment data analysis The integrated software is able to display entire history of the experiment from seeding the cells to the end of cytolysis. The time- and effector to target ratio (E/T)-dependent curves can be displayed in real time allowing for dynamic monitoring of NK cell activity. The electronic readout, cell-electrode impedance is displayed as a dimensionless parameter called Cell Index. The cell index here is determined by calculating, for each measurement frequency $f$, the relative-change (Relative change$(f)=(R_{cell}(f)-R_{background}(f))/R_{background}(f)$) in resistance (a component of impedance) of a well when target cells are present in the well ($R_{cell}(f)$) with respect to background resistance ($R_{background}(f)$) of the well when no cell is present and only cell culture medium is in the well, and then finding the maximum relative-change in resistance for all frequencies measured (Cell Index=max {Relative change$(f)$} for all measurement frequencies). The maximum relative-change in resistance is used as cell index (see equation (4) in Section C. Methods for Calculating Cell Index (CI) and Cell Change Index (CCI) of the present invention). To quantify the lysis at specific time points, the cell index data was exported from RT-CES software to Microsoft Excel and percentage cytolysis at specific E/T ratio at a given time was determined by comparing the cell index for a well with specific E/T ratio to the cell index of a control well without adding NK cells and calculated using the following equation: Percentage of cytolysis=$(1-CI_{at\ a\ given\ E/T\ ratio}/CI_{without\ NK\ cells})\times100$.

Figure 25A:
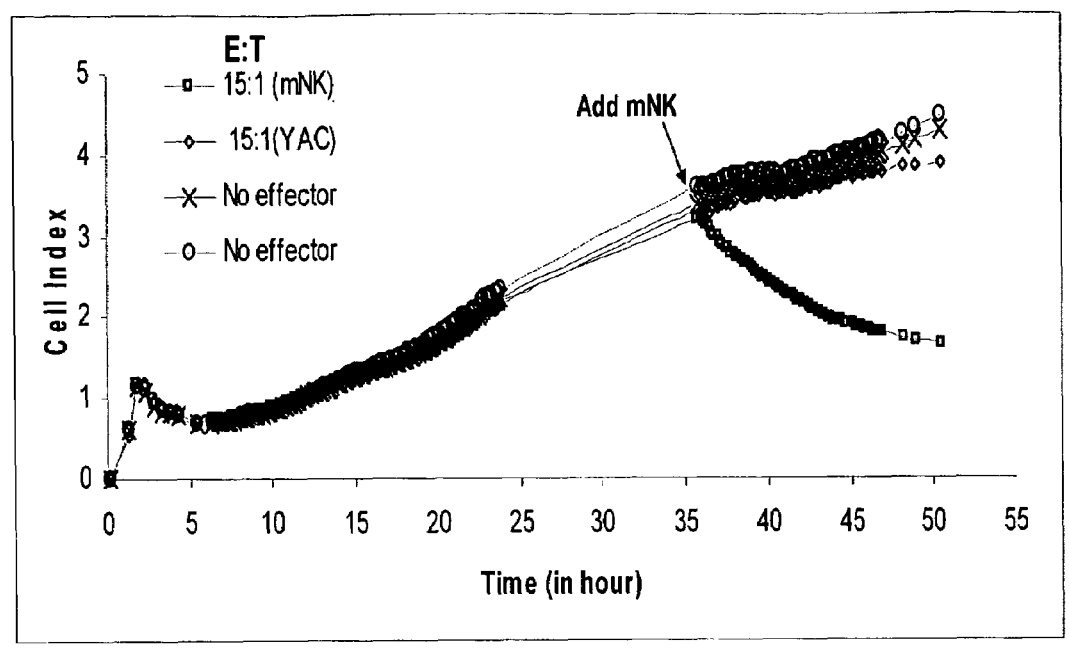
FIG. 25. Dynamic monitoring of NK cell-mediated cytolysis on the RT-CES system (A) Dynamic monitoring of NK-cell mediated cytolysis of NIH 3T3 cells (target cells). The NIH 3T3 cells were seeded in the wells of the 96-well e-plate at 5000 cells/well, and cell attachment, spreading and proliferation were monitored in real time. 34 hours after seeding of the cells, Cell Index (CI) values reached 3, which is equivalent to approximately 10,000 cells/well. 150,000 mNK cells (effector cells) or YAC cells (control effector cells) which function as the negative control were added to each well in triplicates. The mNK cell-mediated cytolysis was then dynamically monitored. (B) Time-dependent cytolytic activity of mNK cells for different ratios of E/T (effector cell number:target cell number). The cytolytic activity at a given time point was calculated and presented as the percentage of cytolysis, or percent cytolysis {% of cytolysis=($CI_{no\ effector}$−$CI_{effector}$)/$CI_{no\ effector}$×100}, where $CI_{effector}$ and $CI_{no\ fector}$ were cell indexes for wells with and without added effector cells, respectively at the time point of interest. For calculation of percent cytolysis shown here, normalized cell index values were used for CI. In general, cell index values or normalized cell index values may be used in the calculation of percentage of cytolysis, or percent cytolysis.
Figure 25B:
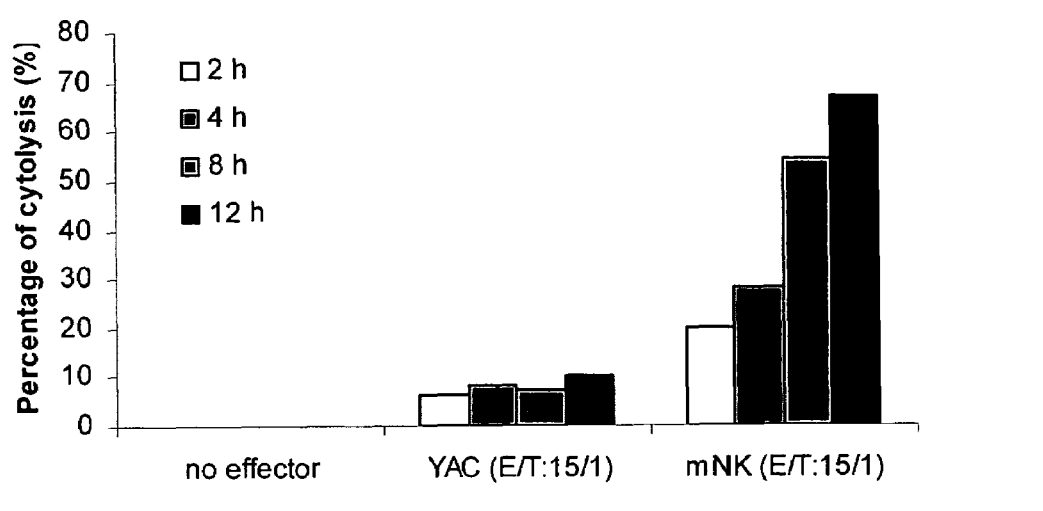

Normalized cell index values were used in the calculation of percentage of cytolysis in FIGS. 25b, 26b, 26d, 27a and 27b Results and Discussion: Dynamic monitoring of NK cell-mediated cytolysis. To assess NK cell-mediated cytolytic activity using the RT-CES system, a murine NK cell line (mNK line), and a target cell line, NIH 3T3 cells were used. The target NIH3T3 cells were seeded in the wells of 96-well e-plate at 5,000 cells per well and cell growth was continuously monitored on RT-CES system every 60 minutes until the cells reached growth phase, 34 hours later. The effector murine NK cells were then directly added to the well at different E/T ratio, and the NK cell-mediated cytolyses was dynamically monitored on the RT-CES system. As shown in the FIG. 25a, a significant decline of the Cell Index was seen in NIH 3T3 cells after the addition of mNK cells at the E/T ratio of 15 to 1, compared to the Cell Index from the media control. Furthermore, no significant decline of the Cell Index was seen in the effector control wells using YAC cells, a T lymphocyte line without cytolysis effect, indicating the decrease in the Cell Index due to addition of the mNK cells is specific and is most likely mediated by cytolysis. A time-dependent cytolysis of the NIH 3T3 cells was also seen in the presences of mNK cells but not in the presence of YAC cells (FIG. 25b). To further confirm the cytolysis effect, target cells were stained at 8 hours after addition of the mNK cells to target cells, when the cytolysis was approximately 50%, and then examined under microscope (data not shown). In the presence of mNK cells, the target cells were effectively cleared away by the cytolytic action of the mNK when compared to control YAC cells. In summary, RT-CES system offers the only assay format so far to directly monitor NK cell mediated cytolysis without labeling the target cells and without using any chemical reporters. In addition, the entire history of the cytolysis can be dynamically monitored on the RT-CES system, which is difficult to perform by any label-based and endpoint assay format. Analysis of the kinetics of cytolysis indicates that for the mNK cells, a slow cytolysis was detected. The cytolysis is detected within 2 hours of mNK cell addition and interestingly, after 4 hours only less than 30% cytolytic activity is detected. Four hour incubation time is the standard incubation period for radioisotope based endpoint assays. Data obtained by the RT-CES system clearly shows that cytolytic activity can reach up to 70%, which occurs after 12 hours of adding the mNK cells. Such cytolytic activity which occurs after the standard incubation time of the assay can be easily missed by existing label-based, endpoint assays. Therefore, the RT-CES system not only offers label free detection but, more importantly, also allows more accurate assessment of cytolytic activity by dynamically monitoring of the entire history of the cytolysis.

Quantitative Measurement of NK Cell-mediated Cytolysis

Figure 26A:
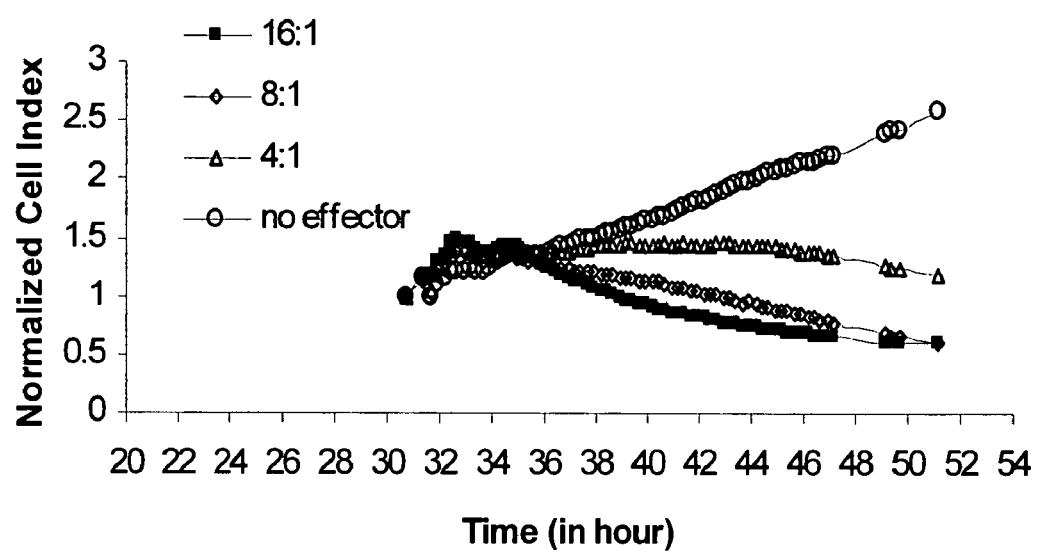
FIG. 26. Label free and quantitative measurement of cytolytic activity of mNK cells (murine Natural Killer cells) and NK92 cells. (A). Quantitative measurement of cytolytic activity of mNK cells. The NIH 3T3 cells were seeded to the 96-well e-plate. Cell growth was monitored in real time on the RT-CES system until the CI values reached 3, equivalent to 10,000 cells/well. The mNK cells (effector cells) were added to target cells at different cell concentrations, making a series of E/T ratios (effector cell number to target cell number) as indicated. The cytolysis of the target cells at different E/T ratios was dynamically monitored on the RT-CES system. The normalized Cell Index was used, in which the Cell Index values obtained from post addition of mNK cells were normalized against the Cell Index value from the same well shortly-before the addition of mNK cells. (B). Time-dependent cytolytic activity of mNK cells at different E/T ratios. The percentage of cytolysis, or percent cytolysis, of the NIH 3T3 cells by mNK cells was calculated according to the equation, {percentage of cytolysis=($NCI_{no\ effector}$−$NCI_{effector}$)/$NCI_{no\ effector}$×100}, where $NCI_{effector}$ and $NCI_{no\ ffector}$ were normalized cell indexes for wells with and without added effector cells, respectively at the time point of interest. The time dependent cytolytic activities are indicated. (C). Quantitative measurement of cytolyic activity of NK92 cells. The target cells, MCF7 were seeded as described and the cell growth was monitored on the RT-CES system as described above. The NK92 cells were then added to each well at different concentration making the series of E/T ratios as indicated. The cytolytic activities of NK92 cells on MCF7 cells at different E/T ratios were dynamically monitored on the RT-CES system. (D). Time-dependent cytolytic activity of NK92 cells at different E/T ratios. The percentage of cytolysis of the MCF7 cells by NK 92 cells was calculated as described in (B), and was indicated.
Figure 26B:
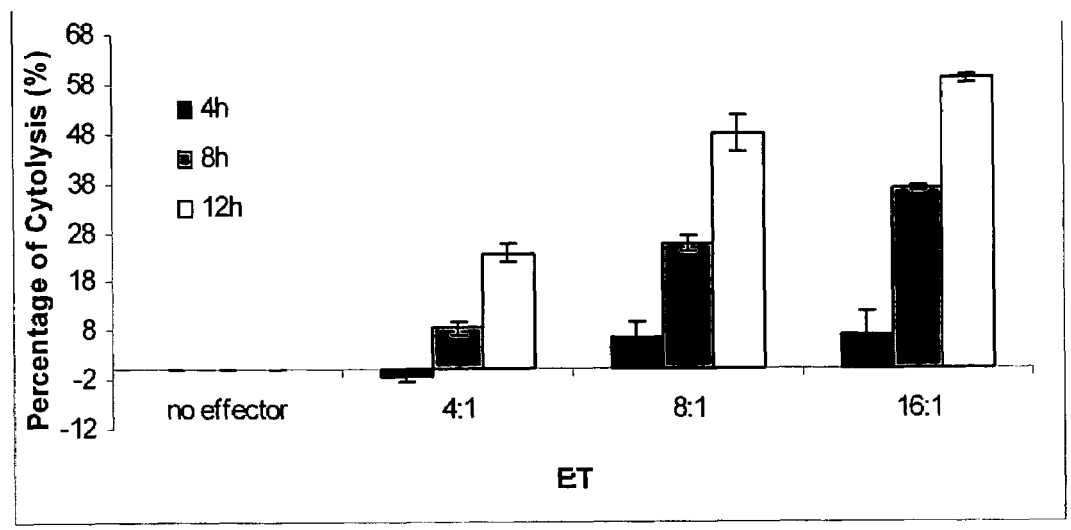
Figure 26C:
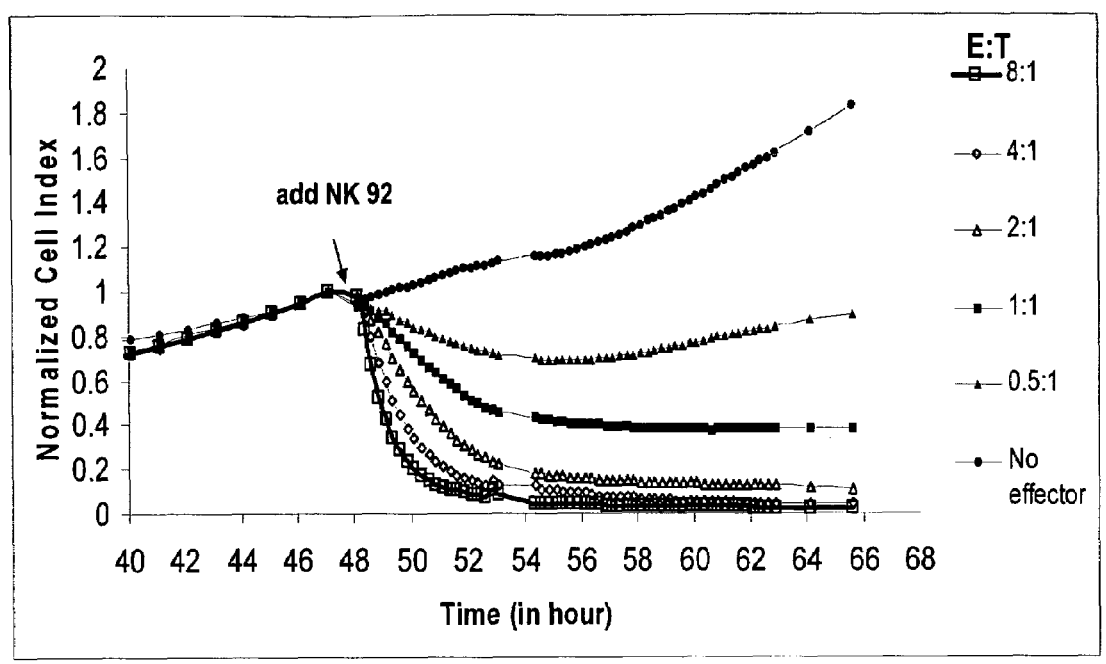
Figure 26D:
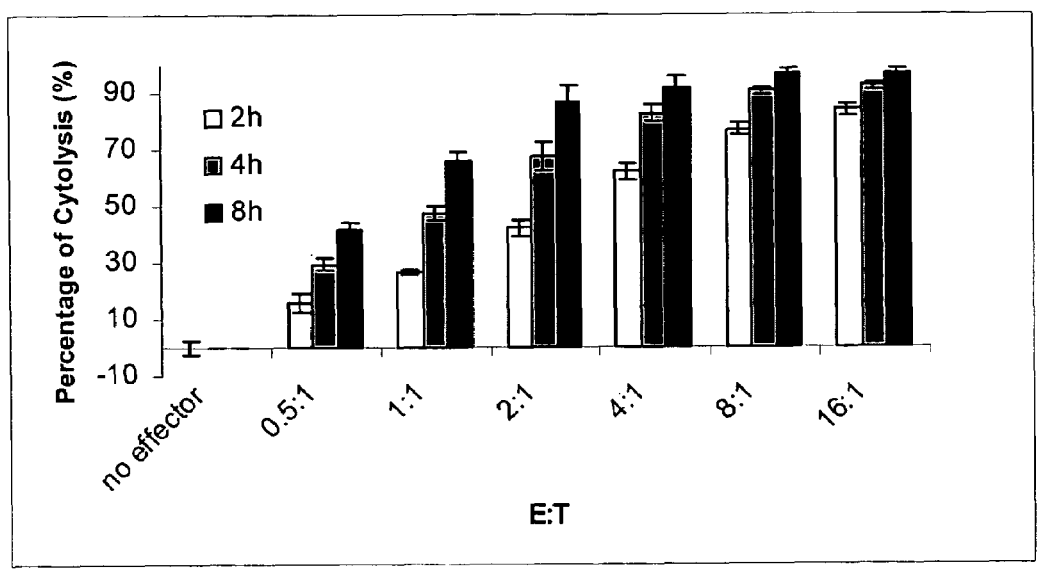

The Cell Index readout of the RT-CES system is correlated with cell number (Solly et al., 2004), and was used to quantitatively monitor cytotoxicity induced by chemical compounds such as anticancer drugs. To test whether mNK cell activity can be quantitatively assayed in the RT-CES system, we monitored cytolysis at different ratios of effector/target. Both murine and human NK cell lines (mNK and NK92) were used as effectors, and the NIH 3T3 line and the MCF7 line (human breast cancer cells) were used as the targets for each of the effectors, respectively. As described above, the target cells were first seeded to the 96well e-plate at 5,000 cells/well, and the cell growth were then monitored on the RT-CES system. When the target cells reached growth phase, the NK cells were directly added to wells at different concentrations. The NK cell-mediated cytolyses at different E/T ratios were then monitored in real time on RT-CES system. As shown in FIGS. 26a and 26c, subsequent to the addition of mNK or NK92 cells to its target cells, the Cell Indices declined compared to the no effector control. The decline in the Cell Index values is E/T ratio dependent. For either case (FIG. 26a for NIH3T3 cells and FIG. 26c for MCF7 cells), the higher the E/T ratio, the lower Cell Index value was obtained. This strongly indicates that RT-CES system allows for specific and quantitative measurement of NK cell-mediated cytolytic activity. Moreover, the dynamic monitoring of the cytolysis may provide more insights with respect to the underlying mechanisms of NK cell-mediated killing. For example, analysis of the dynamics of cytolysis indicates that the NK92 cells are much more potent effectors than mNK cells. At the E/T ratio of 4 to 1 or higher, greater than 90% cytolysis of the MCF7 can be achieved within 4 hours after addition of NK92 cells (FIG. 26d), whereas as for mNK cells it is only about 30% (FIG. 26b). The different cytolytic kinetics of NK cells indicates the distinct nature of interaction between effector cells and target cells, such as expression of NK receptors and ligands, and mechanisms underlying the NK cell-mediated cytolysis.

Figure 27A:
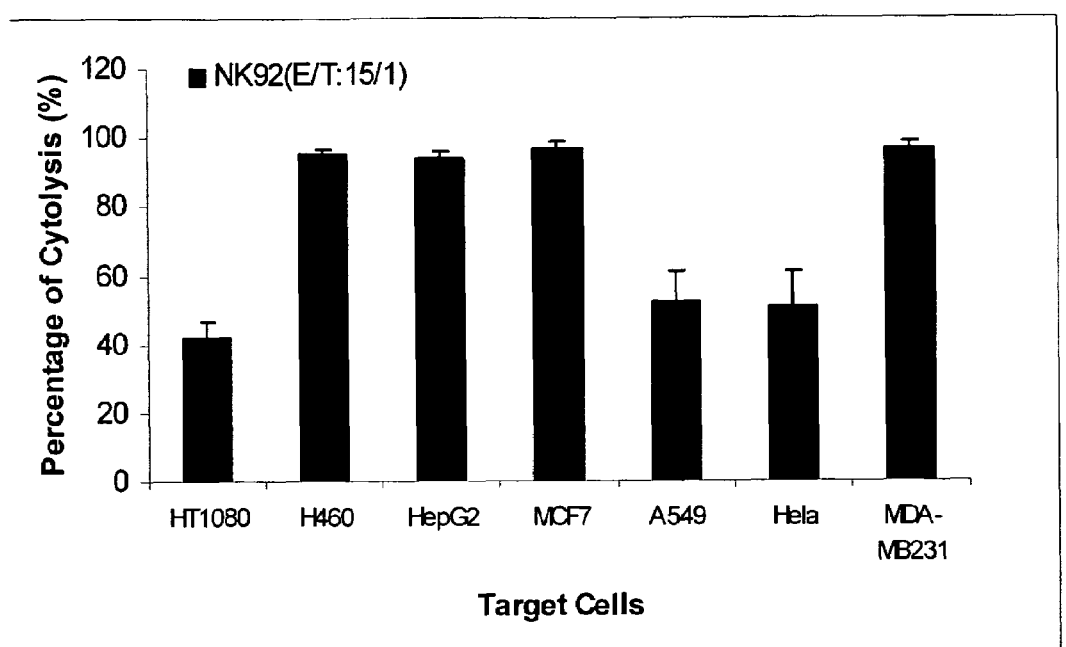
FIG. 27. Label free assessing cytolysis of a variety of cell lines by NK cells on RT-CES system. (A) The NK92-mediated cytolysis of 7 different cancer lines. The percentage of cytolysis indicated for each line is calculated based on the Cell Index value of individual wells after 8 hours of addition of NK92 cells, which showed the maximum cytolysis. (B) The mNK-mediated cytolysis of 9 different cell lines. The percentage of cytolysis indicated for each line is calculated based on the Cell Index values of individual wells after 12 hours of addition of mNK cells, which showed the maximum cytolysis.
Figure 27B:
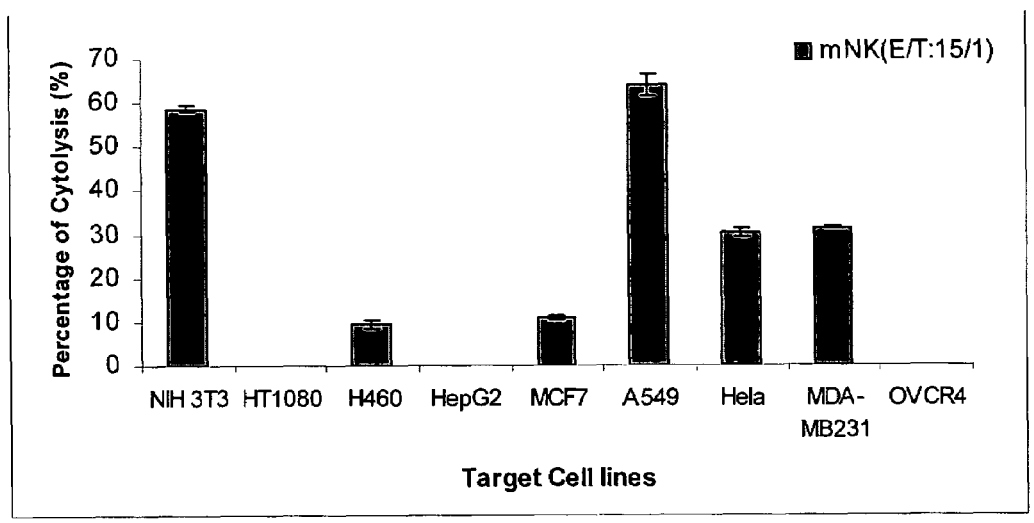
Figure 28:
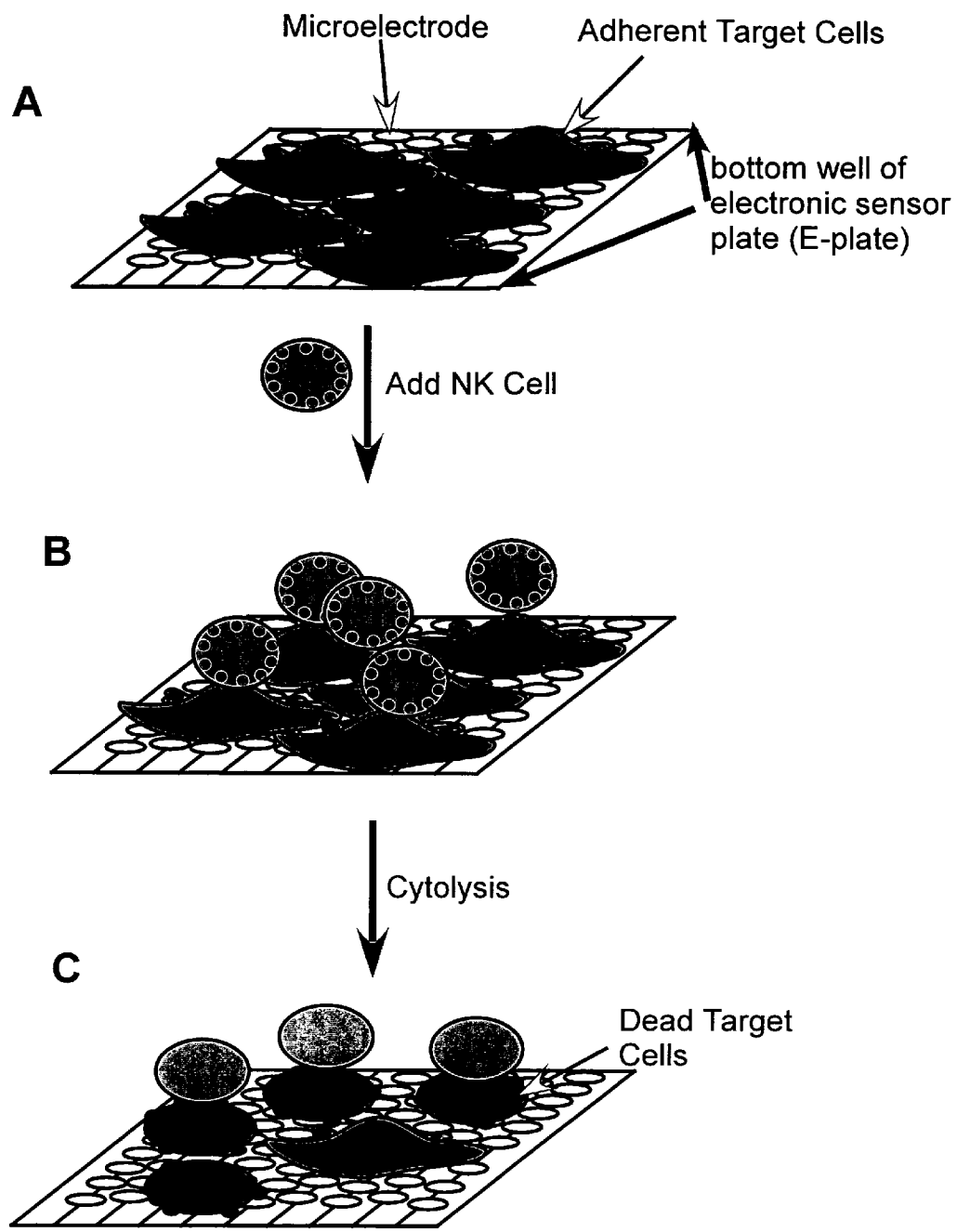
FIG. 28. Principle of RT-CES system used for measurement of effector-mediated cytolysis of target cells. (A) The interaction of adherent target cells with the sensor microelectrodes in the bottom of the well leads to the generation of impedance signal which is displayed as an arbitrary unit called cell index (CI). (B) Addition of suspended effector cells are not detected by the sensor, since these cells do not adhere to the bottom of the well. (C) Effector-mediated cytolysis of target cells is detected by the sensor due to morphological changes of target cells and the loss of interaction of target cells with the microelectrodes in the bottom of the well upon cytolysis.

Label free assessment of NK cell cytolytic activity in a variety of target cell lines on the RT-CES system. Cytolytic activities of mNK and NK92 were tested using 9 cell lines, which include 8 different human cancer cell lines and the NIH 3T3 cell line. The susceptibility of different target cells lines to mNK or NK92-mediated cytolysis is summarized in Table 4 and 5. NK92 shows a broad spectrum of cytolytic activity on cancer cell lines. The cytolysis mediated by NK92 occurs fast and reaches the maximum killing activity prior to 8 hours after addition of NK92 cells. The comparison of susceptibility of 7 cancer cell lines to NK92 cells is shown in FIG. 27a. Among 7 cancer target lines, over 90% cytolysis of 4 target lines was achieved, including H460, HepG2, MCF7 and MDA-MB231. In contrast, mNK cell-mediated cytolysis appears to be more selective than NK92 (FIG. 27b). Among 9 target cell lines, 4 target cell lines showed cytolysis of over 30% after 12 hours of incubation with mNK cells, including NIH 3T3, A549, Hela, and MDA-MB231, while no cytolysis (0%) or weak cytolysis (10%) was found in 5 target lines, including OVCR4, HT1080, HepG2, H460 and MCF7. In addition, the cytolysis mediated by mNK was much slower than NK92, reaching the maximum after 12 hours of addition of mNK cells.

TABLE 4 mNK cell-mediated cytolysis of 9 cell lines

| Cell Name | Cell Type | Species | Maximum Cytolysis (%) at 12 h |
| --- | --- | --- | --- |
| NIH 3T3 | Fibroblast | Murine | 58.80 |
| HT1080 | Fibrosarcoma | Human | 0.10 |
| H460 | Nonsmall cell lung cancer | Human | 9.46 |
| HepG2 | Hepatoma | Human | 0.00 |
| MCF7 | Breast cancer | Human | 11.00 |
| A549 | Nonsmall cell lung cancer | Human | 64.00 |
| HELA | Cervix cancer | Human | 30.30 |
| OVCAR4 | Ovarian cancer | Human | 0.00 |
| MDA-MB-231 | Breast cancer | Human | 31.5 |

TABLE 5

NK92 cell-mediated cytolysis of 7 cell lines

| Cell Name | Cell Type | Species | Maximum Cytolysis (%) at 8 h |
|---|---|---|---|
| HT1080 | Fibrosarcoma | Human | 42.17 |
| H460 | Nonsmall cell lung cancer | Human | 95.40 |
| HepG2 | Hepatoma | Human | 94.10 |
| MCF7 | Breast cancer | Human | 96.50 |
| A549 | Nonsmall cell lung cancer | Human | 52.20 |
| HELA | Cervix cancer | Human | 51.00 |
| MDA-MB-231 | Breast cancer | Human | 97.00 |

Example 5

Dynamic and Label-Free Monitoring of Natural Killer Cell-Mediated Cytolysis of Target Cells Using Electronic Cell Sensor Arrays In this example, a microelectronic sensor-based platform, the RT-CES (real time electronic sensing) system, is introduced for label free assessment of natural killer (NK) cell-mediated cytolytic activity. The RT-CES system was used to dynamically and quantitatively monitor NK-mediated cytolysis of 9 different target cell lines, including cancer cell lines commonly used in laboratories. The cytolysis monitored by RT-CES system was compared with standard techniques such as MTT measurement and shows good correlation and better sensitivity. To test the specificity of the assay, pharmacological agents that inhibit NK cell degranulation and cytolysis were employed and was shown to selectively and dose-dependently inhibit NK-mediated cytolysis of target cells. In summary, the RT-CES system offers fully automated measurement of cytolysis in real time, which enables a large scale screening of chemical compounds or genes responsible for the regulation of NK-mediated cytolytic activity.

Cells. The NK 92, the NIH 3T3 cell line, and all the cancer cell lines used in these experiments were purchased from ATCC. The mouse NK cell line (mNK) was provided by Dr. Hui Shao of University of Louisville. All the cell lines were maintained at 37° C. incubator with 5% $CO_2$. The NK92 and mNK lines were maintained in Alpha MEM with 2 mM L-glutamine, 1.5 g/L Sodium bicarbonate, supplemented with 0.2 m inositol, 0.1 mM 2-mercaptoenthanol, 0.02 mM folic acid, 12.5% horse serum, 12.5% FBS, and 100-200 U/ml recombinant IL-2. Other cancer cell lines were maintained in RPMI media containing 5% FBS and 1% penicillin and streptomycin (GIBCO). The NIH 3T3 cells were maintained in DMEM media containing 10% FBS and 1% penicillin and streptomycin.

RT-CES system. The system includes three components: the analyzer and E-plate station, the integrated software, and 16-well or 96-well E-plate. The E-plate station is placed inside the incubator and connected to the analyzer outside the incubator through a thin cable. The E-plate containing the cells is placed onto the e-plate station inside the incubator and the experiment data are collected automatically by the analyzer under the control of an integrated software. The principles of RT-CES technology has been described previously (Abassi et al., 2004; Solly et al., 2004; Xing et al., 2005).

Cytolytic analysis. Target cells were seeded into the wells of either 16-well or 96-well E-plate in 100 µl of media. Cell growth was dynamically monitored using the RT-CES system for a period of 24-34 hours, depending on the experiment until they reached log growth phase and formed a monolayer. Effector cells at different concentrations were then directly added into individual wells containing the target cells. For background control, effector cells were added to a well without target cells. After addition of the effector cells, the E-plate was returned to the e-plate station and the measurements were automatically collected by the analyzer every 15 minutes for up to 20 hours.

Cell morphology analysis by microscopy. The effect of NK cell-mediated cytolysis on target cells was examined using a Nikon upright microscope. When Cell Index reached 50% of the control upon addition of effector cells, cells were fixed in 80% methanol for 5 minutes and stained with Giemsa blue. The morphology of the cells was examined by microscopy and photographed using an accompanying CCD camera.

Data analysis. The integrated software is able to display entire history of the experiment from seeding the cells to termination of cytolysis. The time- and effector to target ratio (E/T)-dependent curves can be displayed in real time allowing for dynamic monitoring of NK cell activity. The electronic readout, cell-electrode impedance is displayed as a dimensionless parameter called Cell Index. The cell index here is determined by calculating, for each measurement frequency $f$, the relative-change (Relative change$(f) = (R_{cell}(f) - R_{background}(f))/R_{background}(f)$ in resistance (a component of impedance) of a well when target cells are present in the well ($R_{cell}(f)$) with respect to background resistance ($R_{background}(f)$) of the well when no cell is present and only cell culture medium is in the well, and then finding the maximum relative-change in resistance for all frequencies measured (Cell Index=max {Relative change$(f)$} for all measurement frequencies). The maximum relative-change in resistance is used as cell index (see equation (4) in Section C. Methods for Calculating Cell Index (CI) and Cell Change Index (CCI) of the present invention). To quantify the lysis at specific time points, the cell index data was exported from RT-CES software to Microsoft Excel and percentage cytolysis at specific E/T ratio at a given time was determined by comparing the cell index for a well with specific E/T ratio to the cell index of a control well without adding NK cells and calculated using the following equation: Percentage of cytolysis=$(1 - CI_{at\ a\ given\ E/T\ ratio}/CI_{without\ NK\ cells}) \times 100$. Normalized cell index values were used in the calculation of percentage of cytolysis in FIGS. 29C, 31A, 31B, 31C and 31D.

Determination of cytolysis using MTT assay and crystal violet staining. Target cells growing on E-plates were incubated with different ratios of effector cells and incubated overnight. The cytolysis was dynamically monitored using the RT-CES system. At the end of the experiment, the wells were washed in PBS to remove unbound cells and the viable cells attached to the bottom of the E-plate were quantified using MTT reagents according to manufacturers protocols (Sigma) or by fixing the cells with 4% parafarmaldehyde followed by staining with 0.1% crystal violet solution in $H_2O$ for 20 minutes. The cells were washed five times to remove the non-specific stain and the stained cells were solublized in the presence of 0.5% TX-100 overnight. The solubilized stain was measured at wavelength of 590 nm using a plate reader.

Figure 29:
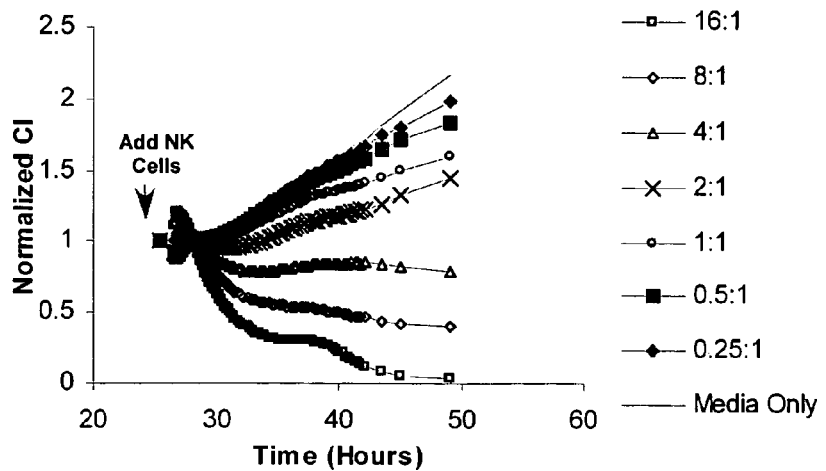
FIG. 29. RT-CES monitoring of NK-92 mediated cytotoxicity. (A) 10,000 A549 target cells were seeded in the wells of E-plates. At the indicated time point (arrow), NK-92 cells were added at different E/T ratios and the viability of A549 cells were dynamically monitored every 15 minutes using the RT-CES syste. (B) Comparison of RT-CES readout with MTT at 25 hours after addition of NK-92 cells. The A549 cells described in (A) were washed and cell viability was assessed using MTT. For each E/T ratio the normalized CI value obtained by RT-CES is plotted together with the absorbance value obtained using MTT assay. (C) For both the RT-CES readout and MTT assay the percent cytolytic activity of NK-92 cells at different E/T ratios was calculated using the formular as described in materials and methods section.
Figure 29:
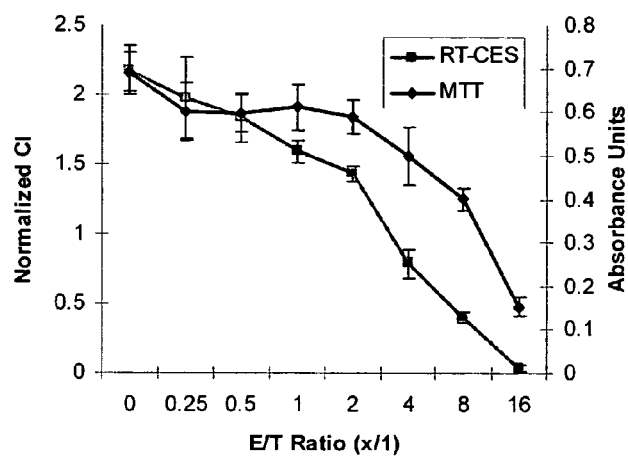
Figure 29:
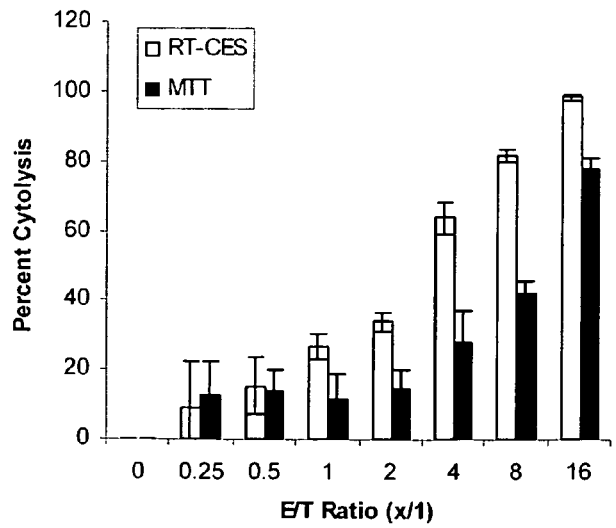

Dynamic monitoring of NK-mediated cytolysis using the RT-CES system. To assess Effector-mediated cytotoxic activity towards target cells we employed NK-92 cell line. NK-92 is a human IL-2 dependent cell line derived from a non-Hodgkin's lymphoma patient that can be easily maintained and propagated in culture and has a very robust cytotoxic activity towards different target cell lines (Gong et al., 1994). NK-92 cell line and some of its derivatives are currently in Phase I clinical trials for the treatment of various cancers (Tam et al., 2003). In order to assess NK-92 mediated cytotoxicity, A549 lung carcinoma cells were seeded in ACEA E-plates at a density of 10000 cells/well and cell growth and proliferation was dynamically monitored using the RT-CES system. Twenty four hours after seeding, NK-cells were added at the indicated effector to target (E/T) ratios (FIG. 29) and the extent of A549 cell viability was dynamically monitored. As shown in FIG. 29A, NK-92 cell addition to A549 cells leads to a density-dependent decrease in A549 cell index over time, indicating that NK-92 cells are eliciting a cytototxic effect upon the A549 cells. NK-92 addition to wells which do not contain any A549 cells did not have any appreciable change relative to background (data not shown). Also, A549 cells which were treated with the media alone continue to grow and proliferate (FIG. 29A). In order to compare the cell viability measured by the RT-CES system with a standard assay, at the end of the experiment, the wells of the E-plate were washed to remove the NK cells and any dead cells and the extent of target cell viability was determined by MTT assay. FIG. 29B shows a comparison of the cell index reading to MTT at 50 hours when the experiment was terminated. Overall, the MTT readout correlates very well with RT-CES measurement of cell impedance. In addition to MTT, crystal violet staining of the target cells was also conducted in parallel which confirmed the MTT results (data not shown). The relative cytolytic activity of NK-92 cells towards A549 target cells as measured by both RT-CES system and MTT at different E/T ratios is shown in FIG. 29C. According to FIG. 29C the RT-CES system is more sensitive than MTT in detecting cytolysis, especially at lower E/T ratios.

Figure 30:
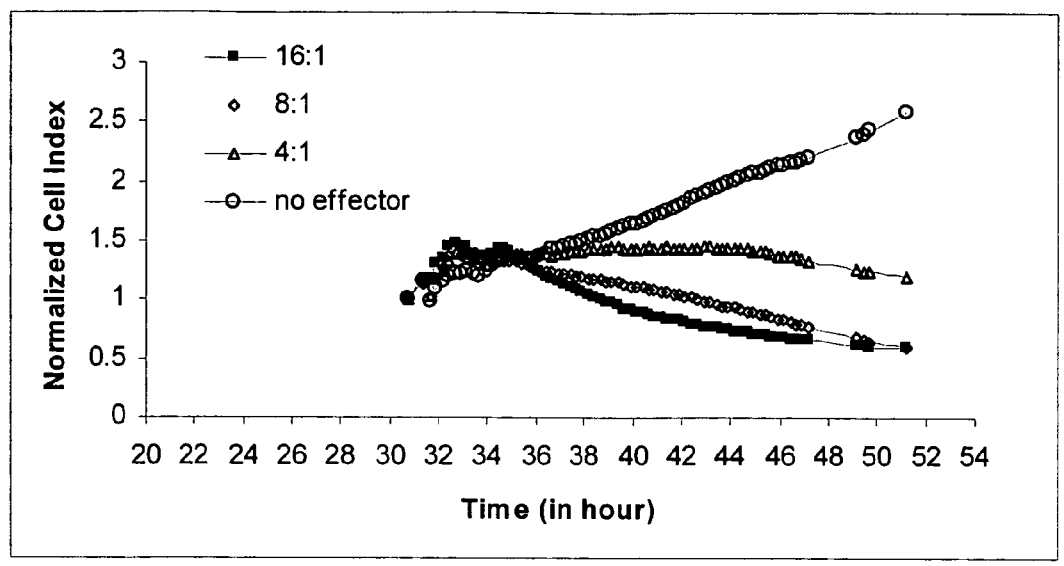
FIG. 30. Dynamic monitoring of mouse NK cell cytolysis of target cells using the RT-CES system. NIH3T3 cells were seeded in the wells of E-plate and mouse NK cells, YAC cells, or media alone were added at the indicated time point (arrow) at different E/T ratios. The viability of NIH3T3 cells were continually monitored using the RT-CES system.

In addition to NK-92 cells, the cytotoxic activity of a mouse NK cell line (mNK) was also assessed using the RT-CES system (FIG. 30A). NIH3T3 mouse fibroblast cell lines were seeded in E-plates and allowed to grow overnight. Twenty four hours after seeding, NK cells were added to the wells at different E/T ratio and the viability of NIH3T3 cells were continually monitored (FIG. 30A). As a control, YAC cells or media alone was added to NIH3T3 cell growing in the wells of the E-plate. The mNK cells induced a progressive decrease in cell index where as addition of YAC cells or media alone had very little effect on the Cell Index recording of NIH3T3 cells (FIG. 30A). To ascertain that the progressive decrease in cell index correlates with cytolysis, the cells in the bottom of the E-plate were washed, fixed, stained with Giemsa dye and photographed using a CCD camera attached to a microscope (data not shown). Addition of YAC cells to NIH3T3 cells growing on the bottom of the E-plates, had no detectable effect on the target cells, whereas addition of mNK cells leads to large gaps and areas on the sensors in the bottom of the well that are devoid of target cells, indicating that cytolysis has taken place. In summary, The RT-CES system allows for a non-invasive, label-free and dynamic way of monitoring effector-mediated cytotoxicity activity towards adherent target cells.

Dynamic Monitoring of NK-mediated cytolysis of different target cells using the RT-CES system. Cytolytic activities of mNK and NK92 were tested using 9 cell lines, which include 8 different human cancer cell lines and the NIH 3T3 cell line. The susceptibility of different target cells lines to mNK or NK92-mediated cytolysis is summarized in Table 4, and 5 in Example 4. NK92 shows a broad spectrum of cytolytic activity on cancer cell lines. The cytolysis mediated by NK92 occurs fast and reaches the maximum killing activity prior to 8 hours after addition of NK92 cells. Among 7 cancer target lines, over 90% cytolysis of 4 target lines was achieved, including H460, HepG2, MCF7 and MDA-MB231. In contrast, mNK cell-mediated cytolysis (Table 4) appears to be more selective than NK92 (Table 5). Among 9 target cell lines, 4 target cell lines showed cytolysis of over 30% after 12 hours of incubation with mNK cells, including NIH 3T3, A549, HeLa, and MDA-MB231, while no cytolysis (0%) or weak cytolysis (10%) was found in 5 target lines, including OVCR4, HT1080, HepG2, H460 and MCF7. In addition, the cytolysis mediated by mNK was much slower than NK92, reaching the maximum after 12 hours of addition of mNK cells.

Figure 31:
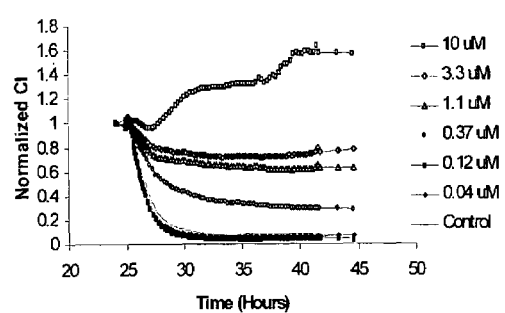
FIG. 31. Specificity of NK-92 mediated cytolysis of target cells. (A) A549 cells were seeded in the wells of E-plates. Twenty four hours after seeding NK-cells at a density of 16:1 (E/T ratio) were pre-incubated with the different concentrations of the MEK inhibitor PD 98059 for thirty minutes and then added to A549 cells at the indicated time point (arrow). The viability of A549 cells were continually monitored using the RT-CES system. (B) The extent of NK-92 mediated cytolystic activity in the presence of MEK inhibitor was calculated at the indicated times post-NK addition as described in materials and methods section. (C) The effect of P13 Kinase inhibitor Wortmannin on NK-92 mediated cytolysis of A549 cells. The cells were treated with the inhibitor as described in (A). (D) Percent cytolytic activity of NK-92 cells was calculated at the end of the experiment described in (C).
Figure 31:
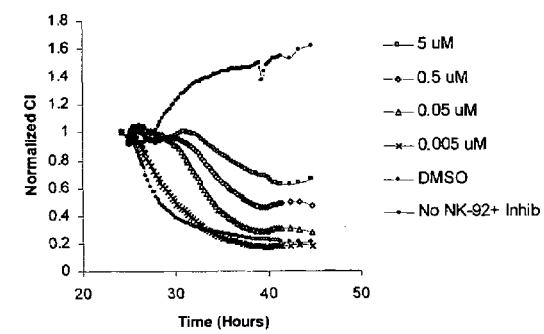
Figure 31:
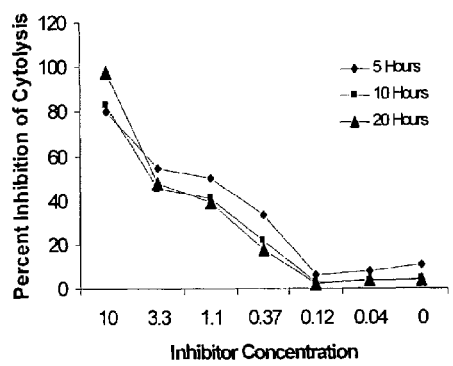
Figure 31:
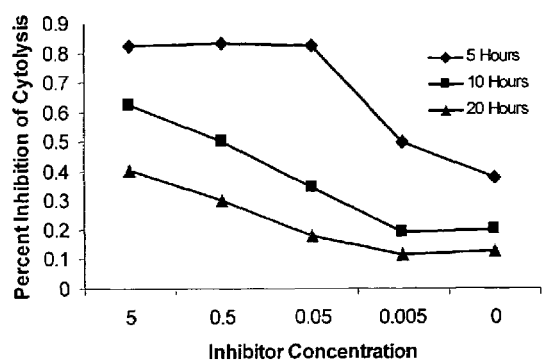

Inhibition of NK-mediated cytolysis of target cells by agents which block the signaling pathways leading to cytotoxicity. The interaction of NK receptors at the cell membrane by target cells leads to the activation of signal transduction machinery which results in cytolysis of target cells (Vivier et al., 2004). One of the key signaling cascades which regulate the fusion of perforin and grnazyme containing secretory granules at the NK/target cell synaptic junction is the phosphatidyl-inositol-3-kinase (PI3K), Rac and mitogen activated protein kinase 1 (Erk) pathway (Djeu et al., 2002; Vivier et al., 2004). In order to determine the specificity of the signaling pathways in regulating NK-mediated cytotoxicity, we therefore sought to utilize specific inhibitors of the PI3K and Erk pathways. NK-92 cells were incubated with both the PI3K inhibitor Wortmannin and the Erk pathway inhibitor PD98059 or DMSO as a control and then added to A549 target cells. As shown in FIG. 31, both Wortmannin and PD98059 dose-dependently inhibited NK-92-mediated cytolysis of A549 cells as monitored by the RT-CES system. As an additional control, A549 target cells were also incubated with both Wortmannin and PD 98059 alone which had minimal effect on the baseline. We calculated percent inhibition of cytolysis for both inhibitors at different time points after NK addition. While the Erk pathway inhibitor resulted in consistent inhibition of cytolysis at all the indicated time points (FIG. 31B), the PI3K inhibitor-mediated inhibition of cytolysis clearly depends on the time point at which the analysis is performed (FIG. 31D). In summary, the experiments shown here clearly establish that the RT-CES system can be used to monitor NK-mediated cytotoxic activity against a variety of different cell lines. Furthermore, interfering with the NK-mediated cytotoxicity response by using inhibitors of the signaling cascade regulating granule fusion significantly attenuates the cytotoxicity response as measured by the RT-CES system. The data also shows that the extent of inhibition can primarily depend on the length of NK incubation with target cells and provides a good rationale for dynamic monitoring of effector-mediated cytotoxicity.

Discussion. NK cells play a central role in innate immune response as well as an intermediary role in bridging the gap between innate immunity and adaptive immunity (Lanier, 2005). NK cells have specialized organelles or granules which house cytolytic enzymes and proteins that are responsible for its cytolytic activity upon encountering pathogen infected cells or tumors (Smyth et al., 2002; Smyth et al., 2005). Recently a number of receptors have been identified on the surface of NK-cells which regulate NK-mediated cytotoxicity in a positive or negative manner depending on the identity of the target cell (Lanier, 2005).

In this report we have described a novel label-free and real-time assay for monitoring NK-mediated cytotoxicity towards different adherent target cells. The assay is based on monitoring the viability of target cells growing on electronic cell sensor arrays fabricated in the bottom well of microtiter plates (E-plates) The interaction of the cells with sensors generates an impedance response which is indicative of the general health of the cell. We have used both human and mouse NK-cells to demonstrate that NK-mediated cytotoxicity activity can be monitored using the RT-CES system, composed of a monitoring system as well as E-plates which contains the microelectrodes for detection of target cells (Abassi et al., 2004; Solly et al., 2004; Xing et al., 2005). NK-mediated cytotoxicity as monitored on the RT-CES system correlates with standard assays such as MTT and crystal violet staining of target cells to assess effector-mediated cytotoxicity (FIG. 29). Both of these assays have been used to monitor effector-mediated cytolysis of target cells (Wahlberg et al., 2001; Peng et al., 2004). The release of granules containing the lytic proteins and proteases is regulated by receptor-mediated signal transduction cascade. Specifically, it has been shown that the PI3K and ERK pathways play a major role in granule exocytosis and cytotoxicity in addition to cytokine secretion (Djeu et al., 2002; Vivier et al., 2004). Using the RT-CES system and confirming earlier data we were able to demonstrate that interfering with the PI3K and Erk pathways by means of small molecular inhibitors blocks NK-mediated cytolysis of target cells (FIG. 31). The extent of the inhibition of cytolysis with different pathway blockers depends on the duration of incubation of NK cells with target cells (FIGS. 31B and 31D). Utilizing standard single point assays such as chromium release assay (CRA), it would've been easy to miss the time-dependent effect of the inhibitors upon cytolysis.

The standard assays monitoring NK-mediated cytotoxicity are label-based and end-point assays requiring significant investment in terms of labor and time. The standard assays can be subdivided into 6 different categories which include radioactive labeling method, enzymatic methods, fluorometric and spectrophotometric methods, ELISA-based methods and morphometric methods. CRA remains the most popular and widely used methods in most research settings for assessing NK and cytotoxic T lymphocyte (CTL) cytotoxicity activity towards target cells (Brunner et al., 1968). However, despite its popularity the CRA does pose certain problems the most formidable of which is the fact that it is a radioactive material with environmental and health hazards. Secondly, the CRA assay is only limited to a four hour window beyond which the natural tendency of chromium 51 to diffuse out of the cell significantly increases the background noise in the assay. Several enzymatic methods based on measuring the activity of enzymes such as lactate dehydrogenase (LDH) and Gmazyme B has been described (Korzeniewski and Callewaert, 1983; Shafer-Weaver et al., 2003). LDH is a common enzyme that is released from target cells upon cytolysis and its activity is quantified in a coupled enzymatic assay which results in the conversion of tetrazolium salt into a red formazan product (Korzeniewski and Callewaert, 1983). There are several major drawbacks to using the LDH assay for NK-mediated cytotoxicity studies. Primarily, serum in the media which is used to culture both the target and effector cells contains significant amounts of LDH which can contribute to the background. Also, the amount of LDH released from target cells target cells upon cytolysis can vary dramatically from cell type to cell type and therefore optimization studies need to be performed for each target cell used. In addition, LDH can be released from effector cells upon cytolysis and in combination with LDH activity in the media can greatly obscure the amount of LDH that is released from target cells upon cytolysis. A Granzyme activity assay in combination with a colorimetric peptide substrate has also been described as a specific measure of effector-mediated cytolysis of target cells (Ewen et al., 2003).

Flow cytometry is another way of assessing effector-mediated cytolysis of target cells (Zimmermann et al., 2005; Hatam et al., 1994). Typically, effector cells are incubated with the target cells and the target cells are labeled with fluorescent-labeled annexin V which recognizes cells that are undergoing cell death. The cells can also be labeled with propidium iodide to discriminate between cells undergoing early apoptotic or necrotic cell death. Alternatively, the effector cells may also be labeled with an antibody specific for membrane marker to discriminate between target cells and effector cells. Taken together, flow cytometry may be a more quantitative and specific way of assessing effector-mediated cytolysis of target cells. However, as described it entails numerous labeling and optimization procedures and combined with relatively limited throughput it may not warrant wide applicability. An ELISA method based on the detection and quantification of Granzyme B has been described in the literature as an alternative to CRA for measuring cytotoxic activity of effector cells (Shafer-Weaver et al., 2003; Shafer-Weaver et al., 2004). In summary, all the standard assays described here for assessing effector-mediated cytolysis of target cells involves extensive labeling of target cells. The assays are typically endpoint assays which only provide a "snapshot" of the effector-mediated cytotoxicity process.

Unlike traditional end-point assays the RT-CES readout of impedance is non-invasive and continuous providing a dynamic measure of effector-mediated cytolysis of target cells. The time resolution in the assay processes provides high content information regarding the extent of the cytotoxicity in addition to the exact time the cytotoxicity takes place at different effector to target ratio. In addition to effector-mediated cytotoxicity, cell sensor impedance technology can also be used to measure cytotoxicity due to other agents such as anti-mitotic and anti-cancer compounds (Solly et al., 2004; Xing et al., 2005). In fact Solly et al (2004) have compared data generated for cell proliferation, cytotoxicity, cytoprotection, cell growth inhibition and apoptosis on the RT-CES system and classical methods such as CellTiter-Glo. They have concluded that the data generated by the RT-CES system is comparable to traditional methods with the added advantage of being non-invasive and providing kinetic parameters (Solly et al., 2004).

REFERENCES

Abassi, Y. A., Jackson, J. A., Zhu, J., O'Connell, J., Wang, X. and Xu, X. (2004) Label-free, real-time monitoring of IgE-mediated mast cell activation on microelectronic cell sensor arrays. J Immunol Methods 292, 195-205.

Brunner, K. T., Mauel, J., Cerottini, J. C. and Chapuis, B. (1968) Quantitative assay of the lytic action of immune lymphoid cells on 51-Cr-labelled allogeneic target cells in vitro; inhibition by isoantibody and by drugs. Immunology 14, 181-96.

Brunner, et al, Quantitative assay for the lytic action of immune lymphoid cells on 51-Cr-labelled allogenetic target cells in vitro; inhibition by sioantibody and by drugs. Immunology 14,181-196, 1968

Cerwenka, A. and Lanier, L. L. (2001) Natural killer cells, viruses and cancer. Nat Rev Immunol 1, 41-9.

Djeu, J. Y., Jiang, K. and Wei, S. (2002) A view to a kill: signals triggering cytotoxicity. Clin Cancer Res 8, 636-40.

Ewen, C., Kane, K. P., Shostak, I., Griebel, P. J., Bertram, E. M., Watts, T. H., Bleackley, R. C. and McElhaney, J. E. (2003) A novel cytotoxicity assay to evaluate antigen-specific CTL responses using a calorimetric substrate for Granzyme B. J Immunol Methods 276, 89-101.

Geldhof et al, Expression of B7-1 by highly metastatic mouse T lymphomas induces optimal natural killer cell-mediated cytotoxicity. Cancer Res. 55, 2730-2733, 1995

Goldberg, J. E., Sherwood, S. W. and Clayberger, C. (1999) A novel method for measuring CTL and NK cell-mediated cytotoxicity using annexin V and two-color flow cytometry. J Immunol Methods 224, 1-9.

Gong, J. H., Maki, G. and Klingemann, H. G. (1994) Characterization of a human cell line (NK-92) with phenotypical and functional characteristics of activated natural killer cells. Leukemia 8, 652-8.

Hatam, L., Schuval, S. and Bonagura, V. R. (1994) Flow cytometric analysis of natural killer cell function as a clinical assay. Cytometry 16, 59-68.

Korzeniewski, C. and Callewaert, D. M. (1983) An enzyme-release assay for natural cytotoxicity. J Immunol Methods 64, 313-20.

Lanier, L. L. (2005) NK cell recognition. Annu Rev Immunol 23, 225-74.

Meyer, et al., Morphometric analysis of cytolysis in cultured cell monolyaers: a simple and versatile method for the evalustion of the lytic activity and the fate of LAK cells, J. Immuno. Meth. 277, 193-211, 2003

Peng, B. G., Liang, L. J., He, Q., Huang, J. F. and Lu, M. D. (2004) Expansion and activation of natural killer cells from PBMC for immunotherapy of hepatocellular carcinoma. World J Gastroenterol 10, 2119-23.

Shafer-Weaver, K., Sayers, T., Strobl, S., Derby, E., Ulderich, T., Baseler, M. and Malyguine, A. (2003) The Granzyme B ELISPOT assay: an alternative to the 51 Cr-release assay for monitoring cell-mediated cytotoxicity. J Transl Med 1, 14.

Shafer-Weaver, K. A., Sayers, T., Kuhns, D. B., Strobl, S. L., Burkett, M. W., Baseler, M. and Malyguine, A. (2004) Evaluating the cytotoxicity of innate immune effector cells using the GrB ELISPOT assay. J Transl Med 2, 31.

Smyth, M. J., Cretney, E., Kelly, J. M., Westwood, J. A., Street, S. E., Yagita, H., Takeda, K., van Dommelen, S. L., Degli-Esposti, M. A. and Hayakawa, Y. (2005) Activation of NK cell cytotoxicity. Mol Immunol 42, 501-10.

Smyth, M. J., Hayakawa, Y., Takeda, K. and Yagita, H. (2002) New aspects of natural-killer-cell surveillance and therapy of cancer. Nat Rev Cancer 2, 850-61.

Solly, K., Wang, X., Xu, X., Strulovici, B. and Zheng, W. (2004) Application of real-time cell electronic sensing (RT-CES) technology to cell-based assays. Assay Drug Dev Technol 2, 363-72.

Tam, Y. K., Martinson, J. A., Doligosa, K. and Klingemann, H. G. (2003) Ex vivo expansion of the highly cytotoxic human natural killer-92 cell-line under current good manufacturing practice conditions for clinical adoptive cellular immunotherapy. Cytotherapy 5, 259-72.

Trapani, J. A. and Smyth, M. J. (2002) Functional significance of the perforin/granzyme cell death pathway. Nat Rev Immunol 2, 735-47.

Vivier, E., Nunes, J. A. and Vely, F. (2004) Natural killer cell signaling pathways. Science 306, 1517-9.

Wahlberg, B. J., Burholt, D. R., Komblith, P., Richards, T. J., Bruffsky, A., Herberman, R. B. and Vujanovic, N. L. (2001) Measurement of NK activity by the microcytotoxicity assay (MCA): a new application for an old assay. J Immunol Methods 253, 69-81.

Xing, J. Z., Zhu, L., Jackson, J. A., Gabos, S., Sun, X. J., Wang, X. B. and Xu, X. (2005) Dynamic monitoring of cytotoxicity on microelectronic sensors. Chem Res Toxicol 18, 154-61.

Zimmermann, S. Y., Esser, R., Rohrbach, E., Klingebiel, T. and Koehl, U. (2005) A novel four-colour flow cytometric assay to determine natural killer cell or T-cell-mediated cellular cytotoxicity against leukaemic cells in peripheral or bone marrow specimens containing greater than 20% of normal cells. J Immunol Methods 296, 63-76.

All of the references cited herein, including patents, patent applications, and publications, and including references cited in the Bibliography, are incorporated by reference in their entireties.

Headings are for the convenience of the reader and do not limit the scope of the invention.

We claim:

1. A method of measuring cytolytic activity comprising:
   a) providing a device capable of monitoring cell-substrate impedance operably connected to an impedance analyzer, wherein said device comprises two or more wells for receiving cells;
   b) adding target cells to said two or more wells, wherein at least one of said two or more wells is a control well and at least one of said two or more wells is a test well;
   c) adding effector cells to said test well and control well;
   d) monitoring impedance of said test well and control well and optionally determining a cell index from said impedance, wherein said monitoring impedance comprises measuring impedance during at least one time point before and at least one time point after said adding effector cells; and
   e) determining viability of said target cells after said adding effector cells by comparing said impedance of said test well and control well or optionally said cell index of said test well and control well at said at least one time point after adding effector cells to said test well and control well or optionally said cell index of said test well or control well at said at least one time point before adding effector cells.

2. The method according to claim 1, wherein said device comprises:
   a) a nonconducting substrate;
   b) two or more electrode arrays fabricated on said substrate, wherein each of said two or more electrode arrays comprises two electrode structures;
   c) said two or more wells on said substrate, wherein each of said two or more arrays is associated with one of said two or more wells; and
   d) at least two connection pads, each of which is located on an edge of said substrate;

wherein for each of said two or more electrode arrays, each of said two electrode structures comprises multiple electrode elements and the first of said two electrode structures of each of said at least two electrode arrays is connected to one of said at least two connection pads, and the second of said two electrode structures of each of said at least two electrode arrays is connected to another of said at least two connection pads;

further wherein at least two of said two or more electrode arrays share one common connection pad;

further wherein each electrode array has an approximately uniform electrode resistance distribution across the entire array; and further wherein said substrate has a surface suitable for cell attachment or growth; wherein said cell attachment or growth on said substrate can result in a detectable change in impedance between or among said electrode structures within each electrode array.

3. The method according to claim 1, wherein said target cells are selected from the group consisting of cancer cells, cells isolated from cancerous tissue, primary cells, endothelial cells and cells from a cell line derived from a living organism.

4. The method according to claim 1, wherein said effector cells are selected from the group consisting of Natural Killer (NK) cells, Cytotoxic T-Lymphocytes (CTLs), neutrophils, easonophils, macrophages, Natural Killer T (NKT) cells, B-cells, T-cells, and any cell type having cytolytic activity.

5. The method according to claim 1, wherein said effector cells are added at a predetermined ratio to said target cells.

6. The method according to claim 1, wherein said monitoring impedance comprises monitoring impedance at regular or irregular time intervals during an assay period.

7. The method according to claim 1, wherein said cell index is a normalized cell index, and further wherein normalization is determined at a time point immediately preceding said adding effector cells.

8. The method according to claim 7, wherein said a time point immediately preceding said adding effector cells comprises a time point selected from the group consisting of less than 2 hours, less than 1 hour, less than 40 minutes, less than 20 minutes, less than 10 minutes, less than 5 minutes, less than 2 minutes, and less than 1 minute prior to adding effector cells.

9. A method of measuring cytolytic activity comprising:
a) providing a device capable of monitoring cell-substrate impedance operably connected to an impedance analyzer, wherein said device comprises two or more wells for receiving cells;
b) adding target cells to at least two wells, wherein at least one well is a control well and at least one well is a test well;
c) adding effector cells to said test well;
d) monitoring impedance of said control and said test wells before and after adding said effector cells and optionally determining a cell index from said impedance, wherein said monitoring said impedance comprises measuring said impedance during at least two time points; and
e) determining viability of said target cells in said test well at a given time point after said adding effector cells by comparing said impedance or optionally said cell index of said test well to said control well at said given time point.

10. The method according to claim 9, wherein said device comprises:
a) a nonconducting substrate;
b) two or more electrode arrays fabricated on said substrate, wherein each of said two or more electrode arrays comprises two electrode structures;
c) said two or more wells on said substrate, wherein each of said two or more arrays is associated with one of said two or more wells; and
d) at least two connection pads, each of which is located on an edge of said substrate;
wherein for each of said two or more electrode arrays, each of said two electrode structures comprises multiple electrode elements and the first of said two electrode structures of each of said at least two electrode arrays is connected to one of said at least two connection pads, and the second of said two electrode structures of each of said at least two electrode arrays is connected to another of said at least two connection pads;
further wherein at least two of said two or more electrode arrays share one common connection pad;
further wherein each electrode array has an approximately uniform electrode resistance distribution across the entire array; and
further wherein said substrate has a surface suitable for cell attachment or growth; wherein said cell attachment or growth on said substrate can result in a detectable change in impedance between or among said electrode structures within each electrode array.

11. The method according to claim 9, wherein said target cells are selected from the group consisting of cancer cells, cells isolated from cancerous tissue, primary cells, endothelial cells and cells from a cell line derived from a living organism.

12. The method according to claim 9, wherein said effector cells are selected from the group consisting of Natural Killer (NK) cells, Cytotoxic T-Lymphocytes (CTLs), neutrophils, easonophils, macrophages, Natural Killer T (NKT) cells, B-cells, T-cells, and a cell type comprising cytolytic activity.

13. The method according to claim 9, wherein said effector cells are added at a predetermined ratio to said target cells.

14. The method according to claim 13, wherein said effector cells are added at a series of predetermined ratio to target cells.

15. The method according to claim 9, wherein said impedance is monitored at least at one time point before adding effector cells and at least at two time points after adding effector cells.

16. The method according to claim 9, wherein said cell index is determined by calculating, for each measurement frequency, the relative-change in resistance of a well when target cells are present in the well with respect to that of the well when no cell is present, and then finding the maximum relative-change in resistance for all frequencies measured.

17. The method according to claim 9, wherein said cell index is a normalized cell index and normalization is at a time point immediately preceding said adding effector cells.

18. The method according to claim 9, wherein said viability decreases if said impedance or cell index decreases after said adding effector cells.

19. The method according to claim 9, wherein percent cytolysis at a given time point after adding effector cells is calculated by the formula of 1-(cell index of test well/cell index of control well).

20. The method according to claim 19, wherein said cell index is a normalized cell index and and normalization is at a time point immediately preceding said adding effector cells.

21. The method according to claim 9, further comprising adding a compound or a factor suspected of stimulating said effector cells.

22. The method according to claim 21, where the compound is selected from a compound library.

23. The method according to claim 21, wherein said factor is selected from the group consisting of a monoclonal antibody, a polyclonal antibody, a peptide, a protein, a lipid, and a biomolecule.

24. The method according to claim 21, wherein said factor is selected from the group consisting of IgG, IgM, IgE and IgA.

25. The method according to claim 9, further comprising determining the quantity of said target cells based on a pre-derived formula that correlates cell number with said cell index at a time point prior to or after said adding effector cells.

26. The method according to claim 9, further comprising adding accessory cells or accessory compounds.

27. The method according to claim 9, further comprising adding an accessory factor that facilitates the cytotoxic activity of said effector cells for said target cells.

28. The method according to claim 27, wherein said accessory factor is an antibody.

29. The method according to claim 28, wherein said antibody recognizes a specific protein or a non-protein epitope on target cells.

30. The method according to claim 28, wherein addition of said antibody results in antibody-dependent facilitation of cytotoxicity of target cells by effector cells or antibody-dependent cell cytotoxicity (ADCC).

31. The method according to claim 28, wherein said method is automated.

32. The method according to claim 28, wherein said impedance is monitored at least at one time point prior to said adding antibody, at least at one time point after said adding antibody and before said adding effector cells and at least at two time points after said adding effector cells.

33. The method according to claim 28, wherein said antibody is selected from a library of antibodies.

34. The method according to claim 28, wherein said antibody is selected from the group consisting of a mouse antibody, a rat antibody, a humanized mouse antibody, and a humanized rat antibody.

35. The method according to claim 28, wherein a percent cytolysis at a time point after said adding effector cells is calculated by the formula of 1-(cell index of test well/cell index of control well).

36. The method according to claim 34, wherein said cell index is a normalized cell index, and normalization is at a time point immediately preceding adding effector cells.

37. The method according to claim 27, wherein said accessory factor is complement.

38. The method according to claim 37, wherein said at least two time points are at least one time point before adding said complement and at least two time points after adding said complement.

39. The method according to claim 37, wherein a percent cytolysis at a time point after adding said complement is calculated by the formula (1-(cell index of test well/cell index of control well)).

* * * * *